US012385033B2

(12) United States Patent
Macosko et al.

(10) Patent No.: US 12,385,033 B2
(45) Date of Patent: Aug. 12, 2025

(54) HIGH-RESOLUTION SPATIAL MACROMOLECULE ABUNDANCE ASSESSMENT

(71) Applicants: THE GENERAL HOSPITAL CORPORATION, Boston, MA (US); THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Evan Macosko, Boston, MA (US); Fei Chen, Cambridge, MA (US); Sam Rodriques, Cambridge, MA (US); Robert Stickels, Cambridge, MA (US); Caroline Anne Martin, Cambridge, MA (US)

(73) Assignees: THE GENERAL HOSPITAL CORPORATION, Boston, MA (US); THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 1254 days.

(21) Appl. No.: 17/051,793

(22) PCT Filed: May 1, 2019

(86) PCT No.: PCT/US2019/030194
§ 371 (c)(1),
(2) Date: Oct. 30, 2020

(87) PCT Pub. No.: WO2019/213254
PCT Pub. Date: Nov. 7, 2019

(65) Prior Publication Data
US 2021/0123040 A1 Apr. 29, 2021

Related U.S. Application Data

(60) Provisional application No. 62/812,747, filed on Mar. 1, 2019, provisional application No. 62/757,753, filed
(Continued)

(51) Int. Cl.
C12N 15/10 (2006.01)
C12Q 1/6841 (2018.01)

(52) U.S. Cl.
CPC ..... *C12N 15/1006* (2013.01); *C12N 15/1065* (2013.01); *C12Q 1/6841* (2013.01)

(58) Field of Classification Search
CPC ............... C12N 15/10; C12N 15/1006; C12N 15/1065; C12Q 1/6841
(Continued)

(56) References Cited

U.S. PATENT DOCUMENTS 6,355,431 B1 * 3/2002 Chee .................... C12Q 1/6813
977/924
8,664,364 B2 3/2014 Schmidt et al.
(Continued)

FOREIGN PATENT DOCUMENTS

EP 2697391 B1 2/2014
WO WO-9004652 A1 * 5/1990
(Continued)

OTHER PUBLICATIONS

International Search Report dated Oct. 8, 2019 for related Application No. PCT/US2019/030194.
(Continued)

Primary Examiner — Aaron A Priest
Assistant Examiner — Randi Lynn Beil
(74) Attorney, Agent, or Firm — Day Pitney LLP; Christopher R. Cowles; Erica A. Fishel

(57) ABSTRACT

Compositions and methods for assessing relative macromolecule abundance (for example, RNA expression levels) in a spatially-defined manner across a tissue sample (for example, from brain, lung, liver, kidney, pancreas, and/or heart) are disclosed, specifically providing deep transcriptomic coverage at high-resolution (for example, at approxi-
(Continued)

mate 10 μm (single cell) resolution) across multiple locations assessed across the tissue sample.

17 Claims, 46 Drawing Sheets

Specification includes a Sequence Listing.

Related U.S. Application Data on Nov. 8, 2018, provisional application No. 62/665,740, filed on May 2, 2018.

(58) Field of Classification Search
USPC .......................................................... 506/3
See application file for complete search history.

(56) References Cited

U.S. PATENT DOCUMENTS

| | | | |
|---|---|---|---|
| 8,835,358 | B2 | 9/2014 | Fodor et al. |
| 9,727,810 | B2* | 8/2017 | Fodor ................ C12Q 1/6853 |
| 9,902,950 | B2 | 2/2018 | Church et al. |
| 10,480,022 | B2 | 11/2019 | Chee |
| 10,662,468 | B2 | 5/2020 | Chee |
| 11,001,879 | B1 | 5/2021 | Chee |
| 11,549,138 | B2 | 1/2023 | Chee |
| 11,761,030 | B2 | 9/2023 | Chee |
| 2003/0006143 | A1 | 1/2003 | Banerjee et al. |
| 2003/0162210 | A1 | 8/2003 | Chetverin et al. |
| 2010/0035763 | A1 | 2/2010 | Chen et al. |
| 2010/0056382 | A1 | 3/2010 | Sussman et al. |
| 2010/0267015 | A1 | 10/2010 | Szasz |
| 2014/0194324 | A1 | 7/2014 | Gormley et al. |
| 2014/0243224 | A1* | 8/2014 | Barnard .............. B01J 19/0046 506/26 |
| 2015/0344942 | A1 | 12/2015 | Frisen et al. |
| 2016/0362733 | A1 | 12/2016 | Chee et al. |
| 2019/0262831 | A1 | 8/2019 | West et al. |

FOREIGN PATENT DOCUMENTS

| | | |
|---|---|---|
| WO | 2008039998 A2 | 4/2008 |
| WO | 2012048341 A1 | 4/2012 |
| WO | 2016138496 A1 | 9/2016 |
| WO | 2016162309 A1 | 10/2016 |
| WO | 2017075293 A1 | 5/2017 |
| WO | 2018075436 A1 | 4/2018 |
| WO | 2019213254 A1 | 11/2019 |

OTHER PUBLICATIONS

Extended European Search Report in corresponding application No. 19796763.1 dated May 2, 2022.
International Search Report dated Nov. 12, 2020 for related Application No. PCT/US2019/030194.
Rodrigues, S. et al. Slide-seq: A scalable technology for measuring genome-wide expression at high spatial resolution. Mar. 28, 2019.
Extended European Search Report in corresponding European application No. 19796763.1 dated Jan. 24, 2022.
Gunderson, K. et al. Decoding Randomly Ordered DNA Arrays. Illumina, Inc. Genome Research. 14:870-877. 2004.
Khrapko, K.R. et al. A method for DNA sequencing by hybridization with oligonucleotide matrix DNA Sequence—J. DNA Sequencing and Mapping, vol. 1, pp. 375-388. 1991
Fodor, S.P. et al. Light-directed, spatially addressable parallel chemical synthesis Science 251, 767-773.
Kuhn, K. et al. A novel, high-performance random array platform for quantitative gene expression profiling. Illumina, Inc. Genome Research. 14:2347-2356. 2004.

* cited by examiner

Z =125 μm    Z =450 μm

Z =1125 μm   Z =1775 μm

SEQUENCE LISTING

```
<160> NUMBER OF SEQ ID NOS: 8

<210> SEQ ID NO 1
<211> LENGTH: 121
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (53)..(58)
<223> OTHER INFORMATION: n is a, c, g, or t
<220> FEATURE:
<221> NAME/KEY: misc_feature
<222> LOCATION: (77)..(91)
<223> OTHER INFORMATION: n is a, c, g, or t

<400> SEQUENCE: 1
tttttgccgg taatacgact cactataggg ctacacgacg ctcttccgat ctnnnnnntc      60
ttcagcgttc ccgagannnn nnnnnnnnn nttttttttt tttttttttt tttttttttt     120
t                                                                   121

<210> SEQ ID NO 2
<211> LENGTH: 108
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (38)..(45)
<223> OTHER INFORMATION: n is a, c, g, or t
<220> FEATURE:
<221> NAME/KEY: misc_feature
<222> LOCATION: (64)..(78)
<223> OTHER INFORMATION: n is a, c, g, or t

<400> SEQUENCE: 2
ttttttttgc cggggctaca cgacgctctt ccgatctnnn nnnntcttc agcgttcccg       60 agannnnnnn nnnnnnnntt tttttttttt tttttttttt tttttttt                 108

<210> SEQ ID NO 3
<211> LENGTH: 58
<212> TYPE: DNA
<213> ORGANISM: Artificial
<220> FEATURE:
<223> OTHER INFORMATION: Synthetic

<400> SEQUENCE: 3
aatgatacgg cgaccaccga gatctacact ctttccctac acgacgctct tccgatct       58

<210> SEQ ID NO 4
<211> LENGTH: 23
<212> TYPE: DNA
<213> ORGANISM: Artificial
<220> FEATURE:
```

```
<223> OTHER INFORMATION: Synthetic

<400> SEQUENCE: 4
aagcagtggt atcaacgcag agt                                          23

<210> SEQ ID NO 5
<211> LENGTH: 22
<212> TYPE: DNA
<213> ORGANISM: Artificial
<220> FEATURE:
<223> OTHER INFORMATION: Synthetic

<400> SEQUENCE: 5
ctacacgacg ctcttccgat ct                                           22

<210> SEQ ID NO 6
<211> LENGTH: 28
<212> TYPE: DNA
<213> ORGANISM: Artificial
<220> FEATURE:
<223> OTHER INFORMATION: Synthetic

<400> SEQUENCE: 6
aagctggtat caacgcagag tgaatggg                                     28

<210> SEQ ID NO 7
<211> LENGTH: 14
<212> TYPE: DNA
<213> ORGANISM: Artificial
<220> FEATURE:
<223> OTHER INFORMATION: Synthetic

<400> SEQUENCE: 7
agctaagcct atca                                                    14

<210> SEQ ID NO 8
<211> LENGTH: 14
<212> TYPE: DNA
<213> ORGANISM: Artificial
<220> FEATURE:
<223> OTHER INFORMATION: Synthetic

<400> SEQUENCE: 8
gcatttgacg atgc                                                    14
```

HIGH-RESOLUTION SPATIAL MACROMOLECULE ABUNDANCE ASSESSMENT

CROSS-REFERENCE TO RELATED APPLICATIONS

This application is a national stage application, filed under 35 U.S.C. § 371, of International Patent Application No. PCT/US19/30194, filed May 1, 2019, entitled "High-Resolution Spatial Macromolecule Abundance Assessment" and published Nov. 7, 2019 as WO 2019/213254, which claims the benefit of priority under 35 U.S.C. § 119(e) to U.S. Provisional Application No. 62/665,740, filed on May 2, 2018, entitled, "High-Resolution Spatial Macromolecule Abundance Assessment"; to U.S. Provisional Application No. 62/757,753, filed on Nov. 8, 2018, entitled, "High-Resolution Spatial Macromolecule Abundance Assessment"; and to U.S. Provisional Application No. 62/812,747, filed on Mar. 1, 2019, entitled, "High-Resolution Spatial Macromolecule Abundance Assessment." The entire contents of these patent applications are hereby incorporated by reference herein.

STATEMENT REGARDING FEDERALLY SPONSORED RESEARCH

This invention was made with government support under Grant Nos. 1DP5OD024583 and 1DP2AG058488-01, awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 27, 2024, is named BN00007_0244_SeqListing.txt and is 2,434 Bytes in size.

FIELD OF THE INVENTION

The invention relates generally to methods and compositions for spatial assessment of macromolecule abundance (e.g., RNA expression, DNA abundance, protein abundance) in a tissue sample.

BACKGROUND OF THE INVENTION

Approaches for spatial monitoring of RNA expression in a tissue sample include traditional histological approaches, in which sections of tissue are fixed, stained, and assessed, e.g., for the presence of individual transcripts across the viewable region of the fixed tissue section on a microscope slide, as well as certain more recent in situ techniques for transcriptome monitoring, which have thus far been afflicted by being laborious in application, offering a low degree of multiplexing with a high degree of technical difficulty and/or providing only low resolution of spatial capture across an array (i.e., providing only approximately 100-200 µm resolution). A need therefore exists for improved approaches that provide spatial transcriptome profiling at resolutions approaching single cell resolution. More generally, a need also exists for improved approaches that provide spatial macromolecule abundance data (e.g., RNA expression, DNA and/or protein abundance) at resolutions approaching single cell resolution.

BRIEF SUMMARY OF THE INVENTION

The current disclosure relates, at least in part, to compositions and methods for assessing macromolecule abundance (e.g., RNA expression levels) in a tissue sample, which provide deep macromolecule-identifying sequence coverage at high-resolution across multiple locations assessed within a tissue sample.

In one aspect, the instant disclosure provides a method for obtaining spatially-resolvable macromolecule abundance data from a tissue sample involving: (i) obtaining a tissue sample from a subject; (ii) preparing a cryosection of the tissue sample; (iii) obtaining a solid support; (iv) contacting the solid support with a capture material, thereby forming a capture material-coated solid support; (v) contacting the capture material-coated solid support with a population of 1-100 µm diameter beads, where each bead has at least 1000 attached oligonucleotides and where the at least 1000 attached oligonucleotides of each bead each includes: (a) a bead identification sequence that is common to all at least 1000 oligonucleotides on each bead and (b) a macromolecule-specific capture sequence, where the bead identification sequence that is common to all at least 1000 oligonucleotides on each bead is either unique to each bead within the population of 1-100 µm diameter beads or is a member of a population of bead identification sequences that is sufficiently degenerate to the population of 1-100 µm diameter beads that a majority of beads within the population of 1-100 µm diameter beads each possesses a unique bead identification sequence, thereby capturing a subpopulation of the population of 1-100 µm diameter beads on the solid support; (vi) identifying the bead identification sequence and associated two-dimensional position on the solid support of individual beads of the subpopulation of beads captured on the solid support; (vii) contacting the subpopulation of 1-100 µm diameter beads captured on the solid support with the cryosection of the tissue sample; and (viii) obtaining the sequences of a population of macromolecules bound to the bead oligonucleotides and an associated bead identification sequence for each macromolecule sequenced, thereby obtaining spatially-resolvable macromolecule abundance data from the tissue sample.

In one embodiment, the macromolecule is RNA, DNA or protein. Optionally, the RNA is a poly-A-tailed RNA.

In certain embodiments, the macromolecule-specific capture sequence includes a poly-dT tail of sufficient length to allow for capture of poly-A-tailed RNAs via hybridization.

In another embodiment, the macromolecule-specific capture sequence includes a gene-specific or transcript-specific sequence.

In an additional embodiment, the DNA is a genomic DNA or a barcode DNA.

In certain embodiments, the macromolecule-specific capture sequence is a component of a loaded transposase.

In some embodiments, a DNA barcode is used to capture an attached protein. Optionally, the barcode-attached protein is an antibody; optionally, the antibody is specifically bound to a target protein; optionally, the antibody-bound target protein possesses a label.

In some embodiments, the tissue sample is obtained from brain, lung, liver, kidney, pancreas and/or heart.

In certain embodiments, the subject is a mammal, optionally a human.

In some embodiments, the tissue sample is fixed. Optionally, the tissue sample is fixed with paraffin. Optionally the tissue sample is fixed using formalin-fixation and paraffin embedding (FFPE).

In one embodiment, the solid support is a slide. Optionally, the solid support is a glass slide.

In some embodiments, the capture material is an adhesive or an elastomer. Optionally, the capture material is applied as a liquid. Optionally, the capture material is applied using a brush or aerosol spray. Optionally, the capture material is a liquid electrical tape. Optionally, the capture material dries to form a vinyl polymer. Optionally, the vinyl polymer is polyvinyl hexane.

In certain embodiments, the 1-100 µm diameter beads include porous polystyrene, porous polymethacrylate and/or polyacrylamide and/or the 1-100 µm diameter beads are porous polystyrene, porous polymethacrylate and/or polyacrylamide.

In some embodiments, the beads are 5-50 µm diameter beads; optionally, the beads are 10-40 µm diameter beads. Optionally, the beads are 10 µm beads.

In one embodiment, the step of (vi) identifying the bead identification sequence and associated two-dimensional position on the solid support of individual beads of the subpopulation of beads attached to the solid support includes performance of a sequencing-by-ligation technique (e.g., SOLiD™).

In certain embodiments, the subpopulation of 1-100 µm diameter beads captured upon the solid support in step (vii) is maintained at a temperature between 4° C. and 30° C., optionally at about room temperature (about 25° C.).

In some embodiments, step (vii) further includes contacting the subpopulation of 1-100 µm diameter beads captured upon the solid support with a wash solution, optionally with a saline solution. Optionally, the solution has between about 1M and about 3M NaCl. Optionally, the solution is a saline-sodium citrate buffer having between about 1M and about 3M NaCl.

In an embodiment, step (viii) obtaining the sequences of a population of macromolecules bound to the bead oligonucleotides and an associated bead identification sequence for each macromolecule sequenced includes performance of a next-generation sequencing approach. Optionally, the next-generation sequencing approach is solid-phase, reversible dye-terminator sequencing; massively parallel signature sequencing; pyro-sequencing; sequencing-by-ligation; ion semiconductor sequencing; Nanopore sequencing and/or DNA nanoball sequencing. Optionally, the next-generation sequencing approach is solid-phase, reversible dye-terminator sequencing.

In one embodiment of the instant disclosure, the obtaining step involves performing reverse transcription upon captured poly-A-tailed RNAs immediately after hybridizing the poly-A-tailed RNAs to the beads and before a digestion step is performed.

In another embodiment, the obtaining step includes performance of long-read sequencing.

In certain embodiments, hybridization is performed in 6×SSC buffer, optionally where the 6×SSC buffer is supplemented with detergent.

In one embodiment, the beads are photocleavable or have a photolabile group. Optionally, cDNA is released from the beads using UV light.

In another embodiment of the instant disclosure, the solid support is cut into small pieces and placed into 1.5 mL tubes for processing.

In certain embodiments, the beads possess primers against specific transcripts.

In some embodiments, the barcoded array is reusable. Optionally, cDNA is generated and then the second strand (carrying the barcode location) is synthesized. Optionally, the second strand is capable of release from the array. Optionally, the cDNA can be cleaved using a restriction enzyme to reveal a poly(A) tail on the array, thereby allowing for the array to be reused.

In one embodiment, transcript-specific amplification is performed.

In one embodiment, the bead identification sequence and associated two-dimensional position on the solid support of individual beads of the subpopulation of beads attached to the solid support is registered in a computer.

In certain embodiments, the method further includes step (ix) generating an image of the tissue sample that depicts the location(s) and relative abundance of one or more captured macromolecles within the sample. Optionally, the image is a two-dimensional image. In some embodiments, the resolution of the image is less than 50 µm between discrete features. Optionally, the resolution of the image is less than 20 µm between discrete features. Optionally, the resolution of the image is less than 10 µm between discrete features.

In another aspect, the disclosure provides a method for extracting and capturing macromolecules from a tissue sample, the method involving: preparing a cryosection of the tissue sample; obtaining a solid support; contacting the solid support with a capture material, thereby forming a capture material-coated solid support; contacting the capture material-coated solid support with a population of beads, where each bead has at least 1000 attached oligonucleotides and where each of the at least 1000 attached oligonucleotides of each bead includes: (a) a bead identification sequence that is common to all at least 1000 oligonucleotides on each bead and (b) a macromolecule-specific capture sequence, where the bead identification sequence that is common to all at least 1000 oligonucleotides on each bead is either unique to each bead within the population of beads or is a member of a population of bead identification sequences that is sufficiently degenerate to the population of beads that a majority of beads within the population of beads each possesses a unique bead identification sequence, thereby capturing a subpopulation of the population of beads upon the solid support; and contacting the subpopulation of beads captured upon the solid support with the cryosection of the tissue sample, thereby extracting and capturing macromolecules from the tissue sample.

In one embodiment, the step of contacting the subpopulation of beads captured upon the solid support with the cryosection of the tissue sample further involves contacting the subpopulation of beads captured upon the solid support with a wash solution, optionally a saline wash solution. In a related embodiment, the saline wash solution includes between about 1M and about 3M NaCl. Optionally, the saline wash solution is a saline-sodium citrate buffer that includes between about 1M and about 3M NaCl.

Another aspect of the instant disclosure provides a composition that includes a glass slide associated with a layer of 1-50 µm diameter beads, where each bead in the layer of 1-50 µm diameter beads has at least 1000 attached oligonucleotides and where the at least 1000 attached oligonucleotides of each bead each includes: (a) a bead identification sequence that is common to all at least 1000 oligonucleotides on each bead and (b) a macromolecule-specific capture sequence, where the bead identification sequence common to all at least 1000 oligonucleotides on each bead is either unique to each bead within the population of 1-50 µm diameter beads or is a member of a population of bead identification sequences that is sufficiently degenerate to the population of 1-50 µm diameter beads that a majority of beads within the population of 1-50 µm diameter beads each possesses a unique bead identification sequence.

In one embodiment, the layer of 1-50 µm diameter beads is associated with the glass slide via a capture material, e.g., by an adhesive and/or via adsorption to an elastomeric surface. Optionally, the elastomeric surface is liquid electrical tape. Optionally, the capture material dries to form a vinyl polymer. Optionally, the vinyl polymer is polyvinyl hexane.

In a further aspect, the instant disclosure provides a method for obtaining spatially-resolvable bulk poly-A-tailed RNA expression data from a tissue sample involving: (i) obtaining a tissue sample from a subject; (ii) preparing a cryosection of the tissue sample; (iii) obtaining a solid support; (iv) contacting the solid support with a capture material, thereby forming a capture material-coated solid support; (v) contacting the capture material-coated solid support with a population of 1-100 µm diameter beads, where each bead has at least 1000 attached oligonucleotides and where the at least 1000 attached oligonucleotides of each bead each includes: (i) a bead identification sequence that is common to all at least 1000 oligonucleotides on each bead and (ii) a poly-dT tail of sufficient length to allow for capture of poly-A-tailed RNAs via hybridization, where the bead identification sequence that is common to all at least 1000 oligonucleotides on each bead is either unique to each bead within the population of 1-100 µm diameter beads or is a member of a population of bead identification sequences that is sufficiently degenerate to the population of 1-100 µm diameter beads that a majority of beads within the population of 1-100 µm diameter beads each possesses a unique bead identification sequence, thereby capturing a subpopulation of the population of 1-100 µm diameter beads on the solid support; (vi) identifying the bead identification sequence and associated two-dimensional position on the solid support of individual beads of the subpopulation of beads captured on the solid support; (vii) contacting the subpopulation of 1-100 µm diameter beads captured on the solid support with the cryosection of the tissue sample; and (viii) (ix) obtaining the sequence of a population of poly-A-tailed RNAs bound to each of the bead oligonucleotides, thereby obtaining spatially-resolvable bulk poly-A-tailed RNA expression data from the tissue sample.

An additional aspect of the instant disclosure provides a method for identifying genes that are significantly correlated or anticorrelated with other genes within a spatially defined array, the method involving selecting each gene in the genome; generating a "true" image in which each bead possessing at least one transcript of the selected gene is identified and representing the transcript by a square of side length 100 pixels; for each gene, generating 50 "random" images in which the same number of transcripts are redistributed across all beads with probability proportional to the number of reads per bead; calculating an elementwise inner product between the image of the selected gene and the 50 random images of every other gene; calculating the mean and standard deviation of the inner products; comparing the mean and standard deviation to the inner products of the image for the selected gene; and comparing the true image of the selected gene with the true image of every other gene, obtaining a Z score for each gene.

In one embodiment, all genes with Z scores greater than 3 are identified as correlated.

In another embodiment, all genes with Z scores less than 3 are identified as anticorrelated.

Another aspect of the instant disclosure provides a method for identifying a gene as spatially non-random, the method involving calculating a set of pairwise Euclidian distances between all beads of an array; for each cluster, identifying a gene as a candidate for statistical significance analysis if a gene exhibits an expression of at least 0.1 transcripts per bead within that cluster or if the variance within that cluster is at least 0.01 transcripts squared and the ratio of the variance to the squared expression is at least 7.5.

An additional aspect of the instant disclosure provides a method for obtaining spatially-resolvable macromolecule abundance data from a tissue sample, the method involving: (i) generating a well array, where each well of the array can hold exactly one bead; (ii) depositing beads into the wells of the well array, optionally by evaporation in a centrifuge; (iii) brushing the well array to remove all of the beads not present in wells; (iv) obtaining a tissue sample from a subject; (v) preparing a cryosection of the tissue sample; (vi) depositing the cryosection onto the well array and centrifuging, thereby forcing the cryosection into the wells of the well array; (vii) adding digestion buffer, thereby lysing the cryosection and causing the RNA of cells of the cryosection to transfer onto the beads in the wells; and (viii) obtaining the sequences of a population of macromolecules bound to the bead oligonucleotides and an associated bead identification sequence for each macromolecule sequenced, thereby obtaining spatially-resolvable macromolecule abundance data from the tissue sample.

In one embodiment, the method further includes performing reverse transcription upon the well contents, and removing beads from the wells by sonication or by photocleavage.

The instant disclosure also provides a method for obtaining spatially-resolvable macromolecule abundance data from a tissue sample involving: (i) obtaining a tissue sample from a subject; (ii) preparing a cryosection of the tissue sample; (iii) obtaining a solid support; (iv) adhering clusters of oligonucleotides in an array attached to the solid support; (v) identifying oligonucleotide cluster identification sequences and associated two-dimensional positions on the solid support of individual oligonucleotide clusters attached to the solid support; (vii) contacting the array with the cryosection of the tissue sample; and (viii) obtaining the sequences of a population of macromolecules bound to the oligonucleotide clusters and an associated oligonucleotide cluster identification sequence for each macromolecule sequenced, thereby obtaining spatially-resolvable macromolecule abundance data from the tissue sample.

In one embodiment, the array includes barcoded clusters of oligonucleotides on a surface.

The instant disclosure also provides a method for obtaining spatially-resolvable macromolecule abundance data from a tissue sample, the method involving: (i) obtaining a tissue sample from a subject; (ii) preparing a cryosection of the tissue sample and adhering the cryosection to a solid support; (iii) forming an array of barcoded oligonucleotide clusters and/or an array of beads attached to barcoded oligonucleotides and contacting the cryosection adhered to the solid support with the array; (iv) identifying oligonucleotide cluster and/or bead array identification sequences and associated two-dimensional positions on the array of the barcoded oligonucleotide clusters and/or the array of beads attached to barcoded oligonucleotides; and (v) obtaining the sequences of a population of macromolecules bound to the array(s) for each macromolecule sequenced, thereby obtaining spatially-resolvable macromolecule abundance data from the tissue sample.

In certain embodiments, an array (puck) is physically transferred from one surface to another. Optionally, a gel encasement is formed on top of the array (puck), thereby allowing beads to be picked up off the surface of the array (puck) without altering bead positions relative to each other.

In some embodiments, the beads and/or array are used for capture of oligo nucleotides.

In certain embodiments, the beads and/or array include or bind oligonucleotide-conjugated antibodies.

In some embodiments, the beads and/or array include or bind nucleic acid hybridization probes. Optionally, the hybridization probes are RNA hybridization probes. Optionally, the hybridization probes are DNA hybridization probes.

In related embodiments, the hybridization probes are capable of specific hybridization to transcriptome or genome sequence(s) of the tissue sample.

In certain embodiments, the hybridization probes include unique molecular identifiers (UMIs). Optionally, the UMIs of the hybridization probes can be counted via sequencing to assess the levels of hybridization probe-bound macromolecules. Optionally, the hybridization probe-bound macromolecules are proteins, exons, transcripts, nucleic acid sequences that include single nucleotide polymorphisms (SNPs) and/or genomic regions.

In some embodiments, the hybridization probes are released from the array or tissue. Optionally, the hybridization probes are released from the array or tissue via (a) cleavage and/or degradation of a photolabile and/or photocleavable group; (b) T7 RNA polymerase transcription; (c) enzymatic cleavage (optionally, RNAseH cleavage of bound RNA or RNAse cleavage of an RNA base in the hybridization probes); and/or (d) chemical cleavage (optionally, disulfide cleavage).

In certain embodiments, the beads or array possess primers capable of specific binding to a selection of one or more target transcripts. Optionally, the one or more target transcripts are T Cell receptor transcript sequences; transcripts of low-expressing proteins (optionally, the low-expressing proteins are transcription factors); and/or synthetic transcripts (optionally, the synthetic transcripts are guideRNAs).

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells, beads arranged upon a flat surface (e.g., a slide), optionally beads captured upon a flat surface (e.g., a layer of beads adhered to or otherwise stably associated with a slide (e.g., a layer of beads adsorbed to a slide-attached elastomeric surface)), etc.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "barcode sequence" is intended to mean a series of nucleotides in a nucleic acid that can be used to identify the nucleic acid, a characteristic of the nucleic acid (e.g., the identity and optionally the location of a bead to which the nucleic acid is attached), or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population (e.g., all nucleic acid species attached to a single bead might possess the same barcode sequence, while different beads present a different shared barcode sequence that serves to identify each such different bead). By way of further example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen (e.g., a tissue sample) are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, "beads", "microbeads", "microspheres" or "particles" or grammatical equivalents can include small discrete particles. The composition of the beads can vary, depending upon the class of capture probe, the method of synthesis, and other factors. In certain embodiments of the instant disclosure, the sizes of the beads of the instant disclosure tend to range from 1 µm to 100 µm in diameter (with all subranges within this range expressly contemplated), e.g., depending upon the extent of image resolution desired, nature of the solid support to be used for spatial bead array construction, sequencing processes (e.g., flow cell sequencing) to be employed, as well as other factors.

As used herein, the term "biological specimen" is intended to mean one or more cell, tissue, organism or portion thereof. A biological specimen can be obtained from any of a variety of organisms. Exemplary organisms include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii, Takifugu rubripes*, yeast, Saccharamoyces *cerevisiae* or *Schizosaccharomyces pombe*; or a *Plasmodium falciparum*. Target nucleic acids can also be derived from a prokaryote such as a bacterium, *Escherichia coli*, Staphylococci or *Mycoplasma pneumoniae*; an archae; a virus such as Hepatitis C virus or human immunodeficiency virus; or a viroid. Specimens can be derived from a homogeneous culture or population of the above organisms or alternatively from a collection of several different organisms, for example, in a community or ecosystem.

As used herein, the term "cleavage site" is intended to mean a location in a nucleic acid molecule that is susceptible to bond breakage. The location can be specific to a particular chemical, enzymatic or physical process that results in bond breakage. For example, the location can be a nucleotide that is abasic or a nucleotide that has a base that is susceptible to being removed to create an abasic site. Examples of nucleotides that are susceptible to being removed include uracil and 8-oxo-guanine as set forth in further detail herein below. The location can also be at or near a recognition sequence for a restriction endonuclease such as a nicking enzyme.

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "cryosection" refers to a piece of tissue, e.g. a biopsy, that has been obtained from a subject, snap frozen, embedded in optimal cutting temperature embedding material, frozen, and cut into thin sections. In certain embodiments, the thin sections can be directly applied to an array of beads captured upon a solid support (e.g., a slide), or the thin sections can be fixed (e.g. in methanol or paraformaldehyde) and applied to a bead-presenting planar surface, e.g., a slide upon which a layer of microbeads has been attached/arrayed.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Two beads can be different from each other by virtue of being attached to different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended.

As used herein, the term "feature" means a location in an array for a particular species of molecule. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful herein can have, for example, sites that are separated by less than 100 µm, 50 µm, 10 µm, 5 µm, 1 µm, or 0.5 µm. An apparatus or method of the present disclosure can be used to detect an array at a resolution sufficient to distinguish sites at the above densities or density ranges.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina™); SOLiD™ technology (Applied Biosystems); Ion semiconductor sequencing (Ion Torrent™); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence.

Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated. The terms "probe" and "target" can be similarly applied to other analytes such as proteins, small molecules, cells or the like.

As used herein, the term "poly T or poly A," when used in reference to a nucleic acid sequence, is intended to mean a series of two or more thiamine (T) or adenine (A) bases, respectively. A poly T or poly A can include at least about 2, 5, 8, 10, 12, 15, 18, 20 or more of the T or A bases, respectively. Alternatively or additionally, a poly T or poly A can include at most about, 30, 20, 18, 15, 12, 10, 8, 5 or 2 of the T or A bases, respectively.

As used herein, the term "random" can be used to refer to the spatial arrangement or composition of locations on a surface. For example, there are at least two types of order for an array described herein, the first relating to the spacing and relative location of features (also called "sites") and the second relating to identity or predetermined knowledge of the particular species of molecule that is present at a particular feature. Accordingly, features of an array can be randomly spaced such that nearest neighbor features have variable spacing between each other. Alternatively, the spacing between features can be ordered, for example, forming a regular pattern such as a rectilinear grid or hexagonal grid. In another respect, features of an array can be random with respect to the identity or predetermined knowledge of the species of analyte (e.g., nucleic acid of a particular sequence) that occupies each feature independent of whether spacing produces a random pattern or ordered pattern. An array set forth herein can be ordered in one respect and random in another. For example, in some embodiments set forth herein a surface is contacted with a population of nucleic acids under conditions where the nucleic acids attach at sites that are ordered with respect to their relative locations but 'randomly located' with respect to knowledge of the sequence for the nucleic acid species present at any particular site. Reference to "randomly distributing" nucleic acids at locations on a surface is intended to refer to the absence of knowledge or absence of predetermination regarding which nucleic acid will be captured at which location (regardless of whether the locations are arranged in an ordered pattern or not).

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are slides and beads capable of assorting/packing upon the surface of a slide (e.g., beads to which a large number of oligonucleotides are attached).

As used herein, the term "spatial tag" is intended to mean a nucleic acid having a sequence that is indicative of a location. Typically, the nucleic acid is a synthetic molecule having a sequence that is not found in one or more biological specimen that will be used with the nucleic acid. However, in some embodiments the nucleic acid molecule can be naturally derived or the sequence of the nucleic acid can be naturally occurring, for example, in a biological specimen that is used with the nucleic acid. The location indicated by a spatial tag can be a location in or on a biological specimen, in or on a solid support or a combination thereof. A barcode sequence can function as a spatial tag. In certain embodiments, the identification of the tag that serves as a spatial tag is only determined after a population of beads (each possessing a distinct barcode sequence) has been arrayed upon a solid support (optionally randomly arrayed upon a solid support) and sequencing of such a bead-associated barcode sequence has been determined in situ upon the solid support.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the term "tissue" is intended to mean an aggregation of cells, and, optionally, intercellular matter. Typically the cells in a tissue are not free floating in solution and instead are attached to each other to form a multicellular structure. Exemplary tissue types include muscle, nerve, epidermal and connective tissues.

As used herein, the term "universal sequence" refers to a series of nucleotides that is common to two or more nucleic acid molecules even if the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer includes a sequence that can hybridize specifically to a universal sequence. Target nucleic acid molecules may be modified to attach universal adapters, for example, at one or both ends of the different target sequences.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The embodiments set forth below and recited in the claims can be understood in view of the above definitions.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows a schematic of the instant method, where DNA barcoded beads were placed onto a rubber surface and barcodes were read out through in situ DNA sequencing. Tissue was then sliced onto the arrays (termed "pucks") and RNA was transferred in a spatially resolved manner. An RNA sequencing library was then prepared off of the puck and transcripts were linked to spatial locations using the bead barcodes. FIG. 1B at left shows an image of base-calls for one base of sequencing. Inset: blown-up image of base calls for one base of sequencing. Right: Binary image representing connected clusters of pixels all sharing the same barcode, which were then identified as beads. FIG. 1C shows an image of the number of transcripts per bead obtained for a hippocampal puck. FIG. 1D shows characterization of lateral diffusion of signal on the Slide-seq surface. Top Left: Image of a Slide-seq surface with shade intensity reflecting transcript counts. Top Right: Image of the adjacent tissue section, stained with DAPI. Boxes represent regions where profile was taken across CA1. (Scale bar: 500 μm). Bottom left: Profile of pixel intensity across CA1 in Slide-seq. Bottom right: Profile across DAPI stained tissue. Dots represent locations of half max of the distribution. FIG. 1E shows a graph of full width at half maximum of profiles across CA1, as in FIG. 1D, taken across 10 samples. FIG. 1F shows a graph of the number of UMIs captured in the method for the top 1%, 10%, and 20% of beads, for several different tissue types. Error bars indicate the standard deviation across samples.

FIG. 2A shows a schematic of the method used for assigning cell types to beads using NMF and NNLS regression (NMFreg). FIG. 2B shows spatial locations of beads called as various cerebellar cell types using NMFreg, for one coronal cerebellar puck. Top Left: Raw locations of beads prior to NMFreg. Top Middle: Forty percent of beads called as granular cells by NMFreg are plotted in dark gray. Top right and bottom: the locations of beads assigned to other cell types called by NMFreg, represented as density plots (7). FIG. 2C shows the fraction of beads that can be confidently assigned to different cell types in cerebellar pucks. Error bars represent standard deviation (N=7 cerebellar pucks). FIG. 2D shows the number of beads called as each atlas-defined cell type for cerebellar pucks. Error bars represent standard deviation (N=7 cerebellar pucks). FIG. 2E shows an alignment of serial sections from 66 Slide-seq experiments in the same mouse hippocampus. Cell type calls from NMFreg are projected onto each bead. Beads assigned to the CA1, CA2/3, and dentate gyrus neuron clusters from hippocampal single cell data are shown. The brightness of each sphere is proportional to the number of transcripts on that bead. Top left: View of stack along the medial-lateral axis. Top right: view of stack along the dorsal-ventral axis. Bottom left: individual pucks through the Z plane. The numbers inset indicate distance from the first section in the stack. FIG. 2F shows a density plot of hilum markers and CA2 markers plotted on all beads assigned to clusters 4, 5 and 6 on a cerebellar puck.

FIG. 3A shows a coronal cerebellar puck, with Purkinje-assigned beads, choroid-assigned beads, a random subset of other beads, and beads expressing Ogfrl1. Bead radius is proportional to the total number of transcripts on the bead or of Ogfrl1. Arrow indicates cluster of Ogfrl1-positive beads. FIG. 3B shows an Allen ISH atlas image of Ogfrl1, from a similar brain region, showing expression in the cochlear nucleus. Arrow indicates Ogfrl1 expression in the cochlear nucleus. FIG. 3C shows the same puck as in FIG. 3A, with beads expressing Rasgrf1 shown in dark gray, and a subset of other beads in light gray. FIG. 3D shows an Allen atlas image of Rasgrf1. FIG. 3E shows a heatmap illustrating the separation of Purkinje-expressed genes into two clusters on the basis of the other genes with which they correlate. The i,jth entry is the number of genes found to overlap with both gene i and j in the Purkinje cluster. See Example 1 (Materials and Methods) below. FIG. 3F shows the Aldoc metagene, and the Cck metagene, both restricted to beads that were called as Purkinje cells. Intensity is proportional to the number of transcripts per bead. FIG. 3G shows the Allen atlas image for Kctd12, in the Aldoc cluster. The top arrow indicates posterior side of lobule V. FIG. 3H shows the Allen atlas image for Cck. FIG. 3I shows the total expression level for each of the indicated metagenes in each of the indicated compartments. The compartments are as shown in FIG. 3G. FIG. 3J shows the correlation between the columns of FIG. 3I. FIGS. 3K and 3L show Allen atlas images of lobule VIII of the cerebellum for the indicated genes. Arrows indicate the ventral horn of lobule VIII.

FIG. 4A shows, at top, all mapped beads plotted for a coronal slice from a mouse sacrificed two hours after injection. Circle radius is proportional to the number of transcripts per bead up to a maximum of 500 transcripts. At bottom are shown three genes that mark the injection site. FIG. 4B shows mapped beads plotted as in FIG. 4A, but for a mouse sacrificed 3 days after injection. Top right shows a DAPI image of an adjacent slice, with injury indicated by an arrow. Plots of circles on a background show cell types as called by NMFReg using the hippocampal dataset. Cluster 13 marks hippocampal neurogenesis, and is interpreted here as marking mitotic cells. Circle radius is proportional to number of transcripts on the bead. FIG. 4C shows mapped beads plotted as in FIG. 4B, for a mouse sacrificed at two weeks following injection. FIG. 4D shows the spatial density profiles of microglia, mitotic cells, and astrocytes plotted for the 3-day puck in FIG. 4B (see Example 1, Materials and Methods, below). FIG. 4E shows the spatial density profiles of microglia, astrocytes, and neurons for the 2-week puck in FIG. 4C. FIG. 4F shows the average thickness of the features shown in FIGS. 4D and 4E, in microns. Error bars show standard error (N=6 for scar, N=6 for penetration, N=3 for mitosis layer). FIG. 4G shows the IEG metagene (see below) plotted for three two-week pucks. FIGS. 4H to 4K show gene ontology-derived metagenes plotted for the indicated transcriptional program, for two 3-day pucks (left) and two 2-week pucks (right). Scale bars: 500 μm. Arrows indicate injection site.

FIG. 5A at top shows an outline of the in situ sequencing and basecalling system established for generation of barcoded surfaces. At bottom is shown a schema for mapping of Illumina barcodes to SOLiD barcodes. FIG. 5B shows hamming distance of match between illumina colorspace converted barcodes and barcodes created through in situ sequencing using SOLiD chemistry. FIG. 5C shows barcode mapping across the puck, light gray shows a barcode had a bijective match between illumina and SOLiD chemistry. Dark gray indicated a barcode that received a SOLiD barcode but was not seen from illumina sequencing. FIG. 5D shows the distribution of packing efficiency of beads across the surface.

FIG. 6A shows an image where all beads were clumped into 20 μm-diameter features and the resulting features were run through NMFreg. Beads were shaded according to the cluster to which they were assigned, legend at right. G=Granule cells, Purk=Purkinje, PV+=Parvalbumin-positive interneuron, PV-=Parvalbumin-negative interneuron, Mg=Microglia, Olig=Oligodendrocytes, BG=Bergmann Glia, Ast=Astrocytes, CP=Choroid Plexus, End=Endothelium, Fib=Fibroblasts. FIG. 6B shows an image as in FIG. 6A, but in this case beads were clumped into features with 100 μm diameter. As this image makes clear, the structure of the tissue was largely lost. FIG. 6C shows the same image as FIG. 6A, but all features that failed to pass the confidence threshold have been shaded in light gray. FIG. 6D shows an image as in FIG. 6C, but for 100 μm features. Upon aggregating features into 100 μm diameter features, the ability to identify choroid plexus, white matter, and granule cells was retained, but no other cell types could be called with confidence. FIG. 6E shows the distributions of L1 norms between the factor loading distributions and the uniform distribution for atlas cells, the original Slide-Seq data (10 µm), 20 µm aggregated features, 40 µm aggregated features, and 100 µm aggregated features, showing the decrease in cell type purity as the feature size increased. FIG. 6F shows the number of UMIs (natural log) versus the confidence, defined as the L2 norm of the vector of factors mapping to the cell type as which the bead was called. There was no relationship observed between the number of UMIs and the bead confidence.

FIG. 7A shows an image where, for each gene of interest, the distribution of the Euclidean distances between all beads in the specified subset expressing at least one transcript of the gene was calculated, with results shown here for Rasgrf1. FIG. 7B shows an image where an equivalent number of beads from the subset with probability proportional to the number of reads per bead were randomly sampled, without replacement. This sampling was performed 1000 times, and for each sample, the distribution of pairwise Euclidean distances between the beads thus chosen was calculated. The elementwise mean of all 1000 samples was then taken to obtain the average distribution of pairwise distances across random samples. FIG. 7C shows an image where the elementwise difference between the distance distribution for the gene of interest and the average distribution was then taken, FIG. 7D shows an image where the elementwise difference between the distance distribution for each of the random samples and the average distribution was taken. FIG. 7E shows a histogram of the sum absolute values of the distributions shown in FIG. 7D, i.e., the L1 norm between distance distributions of the random samples and of the average sample. The L1 norm served as a test statistic: if the gene of interest was distributed proportionally to the number of transcripts per bead, the L1 norm would have been uniformly distributed. For Rasgrf1, the L1 norm of the true distribution was greater than the L1 norms of any of the random samples, so p<0.001. (Because there were only 1000 samples for reasons of computational complexity, the smallest observable p value was p<0.001).

FIGS. 11A to 10D display a plot showing the percentage of reads at each bead mapping to ribosomal RNA, prior to alignment, for the 180819_3 puck (same as in FIG. 4A). FIG. 10D shows plots for three cerebellar (non-injected) pucks, showing hemoglobin transcripts (left) and Lars2 transcripts (right). The correlation between hemoglobin and Lars2 in FIGS. 10B and 10C was in great excess over the correlations observed in FIG. 10D.

DETAILED DESCRIPTION OF THE INVENTION

Figure 1A:
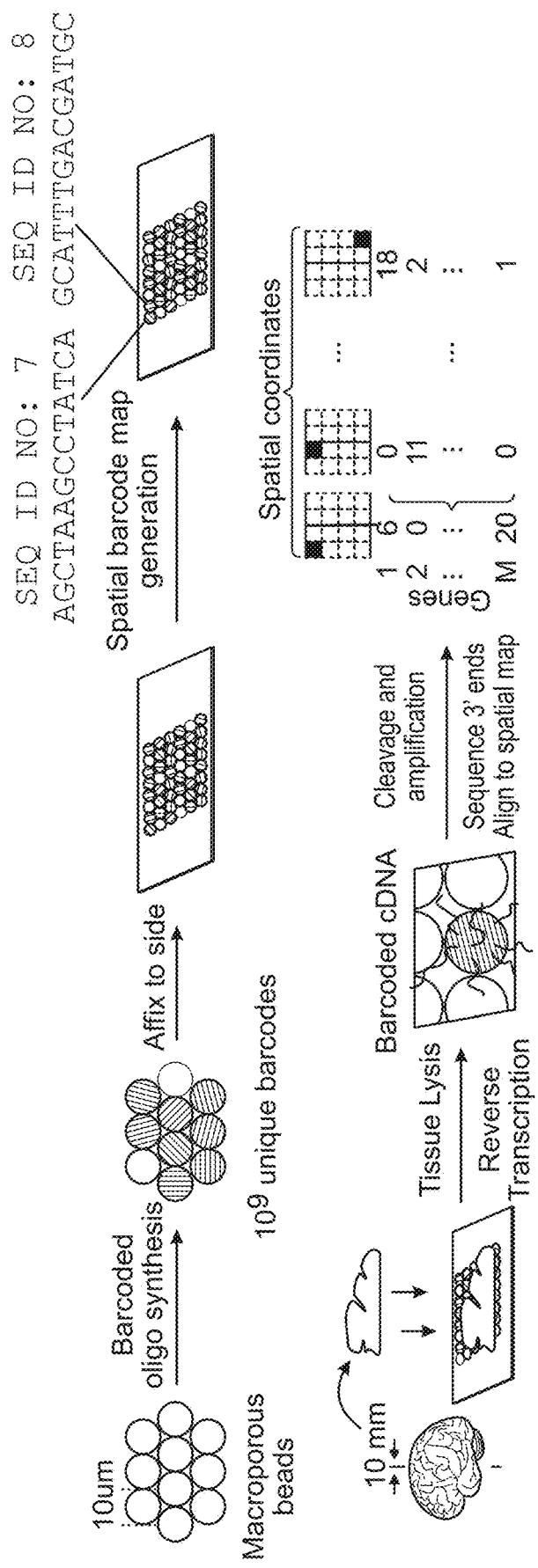
FIGS. 1A to 1F show that the "Slide-seq" approach of the instant disclosure enabled RNA capture from tissue with high resolution.

The present disclosure is directed, at least in part, to the discovery that a tightly packed spatially barcoded microbead array (e.g., an array of 10 µm diameter beads packed at an inter-bead spacing of 20 µm or less, where each bead possesses a bead-specific barcode within bead-attached capture oligonucleotides) created via application of a capture material to a solid support (e.g., application of a liquid electrical tape to a glass slide, followed by application of a layer of microbeads) can be used to capture cellular transcriptomes (or other macromolecules) of cryosectioned tissue, in a manner that is both spatially resolvable at high resolution (e.g., at resolutions of 20 µm between image features) and with deep coverage (i.e., high-resolution images of relative expression for individual transcripts can be generated using the methods and compositions of the instant disclosure, for a large number (i.e., tens, hundreds or even thousands) of transcripts, across an individual cryosectioned tissue sample).

The instant disclosure enables spatially resolved capture of nucleic acids for sequencing from cells and tissues with approximate 10 µm (single cell) resolution. Art-recognized spatial profiling technologies have relied upon either targeted in situ techniques, which were laborious and offered only a low degree of multiplexing with a high degree of technical difficulty, or have offered only very low resolution on spatial capture arrays (resolutions of approximately 100-200 prn). The instant disclosure provides a level of image resolution that is a full order of magnitude superior in lateral resolution, and two orders of magnitude superior in capture area. By using mRNA capture and subsequent high-throughput sequencing (Illumina™ bead-based sequencing as exemplified herein), the instant disclosure provides methods and compositions that are easily adoptable and allows for whole transcriptomic profiling of complex tissues.

One key concept of the compositions and methods described herein is use of a spatially barcoded array of oligonucleotide-laden beads to capture mRNA from tissue sections. Exemplified beads are synthesized with a unique or sufficiently unique bead barcode as previously described, e.g., in WO 2016/040476 (PCT/US2015/049178), wherein an exemplary sufficiently unique bead barcode is one that is a member of a population of barcode sequences that is sufficiently degenerate to a population (e.g., of beads) that a majority of individual components (e.g. beads) of the barcoded population each possesses a unique barcode sequence, where the remainder (minority) of the population may possess barcodes that are redundant with those of other members within the remainder population, yet such redundancy can either be eliminated or otherwise adjusted for (e.g., normalized, averaged across/between redundant members, etc.) with only minor impact upon, e.g., the image resolution obtained when employing such a barcoded population. Herein, discovery and development has occurred in at least the following areas: 1) tiling of beads into a monolayer surface; 2) interrogation of the sequence of each bead barcode of the surface via sequencing by ligation on an standard microscope; 3) capture of RNA from cells and tissues onto the bead array, particularly noting the instant use of cryosectioned tissue samples; 4) performing reverse transcription (RT) and generating barcoded sequencing libraries as previously described in WO 2016/040476; and 5) next-generation sequencing of the barcoded libraries (exemplified herein using an Illumina™ platform) followed by bead barcode matching to the spatial location of the read. Generation of high-resolution barcoded arrays via on-surface sequencing of capture probe beads (noting that exemplified beads have been prepared as previously described in WO 2016/040476) is a distinguishing feature of the instant disclosure, as well as techniques to capture RNA to the barcoded bead array.

The "Slide-seq" approach of the instant disclosure therefore enabled the localization of cell types and gene expression patterns in tissue with 10-micron resolution in an unbiased manner.

The spatial organization of cells in tissue has a profound influence on their physiology, yet a high-throughput, sequencing-based readout of gene expression with cellular resolution has been previously lacking. The Slide-seq approach of the instant disclosure provides a method that was demonstrated to enable facile generation of large volumes of unbiased spatial transcriptomes with 10 μm spatial resolution, comparable to the size of individual cells. To perform Slide-seq, RNA is transferred from freshly frozen tissue sections onto a surface covered in DNA-barcoded polystyrene beads with known positions. Subsequent sequencing of the bead-anchored RNA allows for the assignment of beads to known cell types derived from scRNAseq data, revealing the spatial organization of cell types in the tissue with 10 μm resolution. Slide-seq was initially applied herein to systematically characterize spatial gene expression patterns in the Purkinje layer of the mouse cerebellum, identifying several genes not previously associated with Purkinje cell compartments. Applying Slide-seq to a model of traumatic brain injury further allowed for the characterization of underlying genetic programs varying over time and space in response to injury. Slide-seq has thus provided a new methodology to identify novel molecular patterns within tissues at high resolution and can accommodate large volumes of tissue, thereby enabling the generation of high resolution transcriptome atlases at scale, among other applications.

The function of complex tissues is fundamentally tied to the organization of its resident cell types. However, unbiased methods for exploring genome-wide, spatial distributions of gene expression have heretofore been lacking. Recently developed multiplexed in situ hybridization and sequencing-based approaches have allowed for patterns of gene expression to be determined within cells and tissues with subcellular spatial resolution (1-3), but can be laborious, low-throughput, and require high up-front investment in specialized knowledge and equipment. In addition, most in situ approaches require the identification and selection of specific target genes for measurement, which has limited de novo discovery of spatially varying gene expression patterns. By contrast, recent technology has enabled routine high-throughput single-cell RNA-sequencing (sc-RNAseq) of complex tissues, but with a lack of information about the location of cells in the tissue due to dissociation (4, 5). Previous technologies for spatially encoded RNA-sequencing using barcoded oligonucleotide capture arrays have previously been limited to resolutions in the hundreds of microns (6), which is insufficient for detecting many of the spatial features of tissues.

The compositions and methods of the instant disclosure offer a number of advantages over other, art-recognized methods for spatial detection of analyte profiles (e.g., expression profiles). Without limitation, such advantages include:

- The currently disclosed methods have been extensively optimized for success. In particular, in certain aspects, it was identified as very important in the instantly disclosed methods that reverse transcription was performed immediately after the hybridization step, prior to a digestion step. When it was attempted, performing a digestion step first did not work. In addition, numerous different hybridization buffers were employed in different experiments, and several did not work. For example, using reverse transcriptase buffer during hybridization resulted in greatly reduced library sizes. The 6×SSC buffer employed in the below Examples was identified as effective, though use of 6×SSC supplemented with detergent (e.g., Triton-X) resulted in increased capture of RNA.
- The analysis methods of the instant disclosure, particularly those set forth in the Overlap Analysis and Significant Gene Calling sections of Example 1 below, provide improved methods for (a) identifying genes with correlated spatial distributions; (b) cell types with correlated spatial distributions; and (c) genes with significantly non-random spatial distributions.
- The methods for attachment of beads to a solid support resulted from a process of non-routine optimization. Several surface coverings were attempted, such as acrylamide and polydimethylsiloxane (PDMS), and the liquid electrical tape (vinyl polymer)-coated surface currently exemplified was identified as a preferred embodiment.
- The currently exemplified methods for collecting cDNA from beads were also the result of non-routine optimization. In the instant Examples, the beads were attached reversibly to the liquid tape surface. Optionally, it is specifically contemplated that photocleavable beads can also be used, where the cDNA can be released from the beads using UV light. Inclusion and use of photolabile beads and/or photolabile conjugates is also expressly contemplated.

Other advantages of the instant disclosure are also described throughout the instant document, including those that would be apparent to a skilled artisan.

Various expressly contemplated components of certain compositions and methods of the instant disclosure are considered in additional detail below.

Solid Supports

In certain aspects, the present disclosure provides a method for generating and using a spatially tagged array of microbeads to perform deep expression profiling upon cryosectioned tissue samples, with high image resolution. The method can include the steps of (a) attaching different nucleic acid probes to beads that are then captured upon a solid support to produce randomly located probe-possessing beads on the solid support, wherein the different nucleic acid probes each includes a barcode sequence (that is shared by all such nucleic acid probes of a single bead), and wherein each of the randomly located beads includes a different barcode sequence(s) from other randomly located beads on the solid support; (b) performing a nucleic acid detection reaction on the solid support to determine the barcode sequences of the randomly located beads on the solid support; (c) contacting a biological specimen with the solid support that has the randomly located beads; (d) hybridizing the probes presented by the randomly located beads to target nucleic acids from portions of the biological specimen that are proximal to the randomly located beads; and (e) extending the probes of the randomly located beads to produce extended probes that include the barcode sequences and sequences from the target nucleic acids, thereby spatially tagging the nucleic acids of the biological specimen.

Any of a variety of solid supports can be used in a method, composition or apparatus of the present disclosure. Particularly useful solid supports are those used for nucleic acid arrays. Examples include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a solid support can be within or part of a vessel such as a well, tube, channel, cuvette, Petri plate, bottle or the like. Optionally, the vessel is a flow-cell, for example, as described in WO 2014/142841 A1; U.S. Pat. App. Pub. No. 2010/0111768 A1 and U.S. Pat. No. 8,951,781 or Bentley et al., Nature 456:53-59 (2008), each of which is incorporated herein by reference. Exemplary flow-cells are those that are commercially available from Illumina, Inc. (San Diego, CA) for use with a sequencing platform such as a Genome Analyzer®, MiSeq®, NextSeq® or HiSeq® platform. Optionally, the vessel is a well in a multiwell plate or microtiter plate.

In certain embodiments, a solid support can include a gel coating. Attachment, e.g., of nucleic acids to a solid support via a gel is exemplified by flow cells available commercially from Illumina Inc. (San Diego, CA) or described in US Pat. App. Pub. Nos. 2011/0059865 A1, 2014/0079923 A1, or 2015/0005447 A1; or PCT Publ. No. WO 2008/093098, each of which is incorporated herein by reference. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Publ. Nos. 2014/0079923 A1, or 2015/0005447 A1, each of which is incorporated herein by reference).

In some embodiments, a solid support can be configured as an array of features to which beads can be attached. The features can be present in any of a variety of desired formats. For example, the features can be wells, pits, channels, ridges, raised regions, pegs, posts or the like. Exemplary features include wells that are present in substrates used for commercial sequencing platforms sold by 454 LifeSciences (a subsidiary of Roche, Basel Switzerland) or Ion Torrent (a subsidiary of Life Technologies, Carlsbad California). Other substrates having wells include, for example, etched fiber optics and other substrates described in U.S. Pat. Nos. 6,266,459; 6,355,431; 6,770,441; 6,859,570; 6,210,891; 6,258,568; 6,274,320; US Pat app. Publ. Nos. 2009/0026082 A1; 2009/0127589 A1; 2010/0137143 A1; 2010/0282617 A1 or PCT Publication No. WO 00/63437, each of which is incorporated herein by reference. In some embodiments, wells of a substrate can include gel material (with or without beads) as set forth in US Pat. App. Publ. No. 2014/0243224 A1, which is incorporated herein by reference.

Features can appear on a solid support as a grid of spots or patches. The features can be located in a repeating pattern or in an irregular, non-repeating pattern. Optionally, repeating patterns can include hexagonal patterns, rectilinear patterns, grid patterns, patterns having reflective symmetry, patterns having rotational symmetry, or the like. Asymmetric patterns can also be useful. The pitch of an array can be the same between different pairs of nearest neighbor features or the pitch can vary between different pairs of nearest neighbor features.

In particular embodiments, features on a solid support can each have an area that is larger than about 100 nm$^2$, 250 nm$^2$, 500 nm$^2$, 1 µm$^2$, 2.5 µm$^2$, 5 µm$^2$, 10 µm$^2$ or 50 µm$^2$. Alternatively or additionally, features can each have an area that is smaller than about 50 µm$^2$, 25 µm$^2$, 10 µm$^2$, 5 µm$^2$, 1 µm$^2$, 500 nm$^2$, or 100 nm$^2$. The preceding ranges can describe the apparent area of a bead or other particle on a solid support when viewed or imaged from above.

Beads

Certain aspects of the instant disclosure employ a collection of beads or other particles, to which oligonucleotides are attached. Suitable bead compositions include those used in peptide, nucleic acid and organic moiety synthesis, including, but not limited to, plastics, ceramics, glass, polystyrene, methylstyrene, acrylic polymers, paramagnetic materials, thoriasol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers IN is a helpful guide, which is incorporated herein by reference in its entirety. The beads need not be spherical; irregular particles may be used. In addition, the beads may be porous, thus increasing the surface area of the bead available for either capture probe attachment or tag attachment. The bead sizes can range from nanometers, for example, 100 nm, to millimeters, for example, 1 mm, with beads from about 0.2 µm to about 200 µm commonly employed, and from about 5 to about 20 µm being within the range currently exemplified, although in some embodiments smaller or larger beads may be used.

The particles can be suspended in a solution or they can be located on the surface of a substrate (e.g., arrayed upon the surface of a solid support, such as a glass slide). Art-recognized examples of arrays having beads located on a surface include those wherein beads are located in wells such as a BeadChip array (Illumina Inc., San Diego CA), substrates used in sequencing platforms from 454 LifeSciences (a subsidiary of Roche, Basel Switzerland) or substrates used in sequencing platforms from Ion Torrent (a subsidiary of Life Technologies, Carlsbad California). Other solid supports having beads located on a surface are described in U.S. Pat. Nos. 6,266,459; 6,355,431; 6,770,441; 6,859,570; 6,210,891; 6,258,568; or 6,274,320; US Pat. App. Publ. Nos. 2009/0026082 A1; 2009/0127589 A1; 2010/0137143 A1; or 2010/0282617 A1 or PCT Publication No. WO 00/63437, each of which is incorporated herein by reference. Several of the above references describe methods for attaching nucleic acid probes to beads prior to loading the beads in or on a solid support. As such, the collection of beads can include different beads each having a unique (or sufficiently unique and/or near-unique, as described elsewhere herein) probe attached. It will however, be understood that the beads can be made to include universal primers, and the beads can then be loaded onto an array, thereby forming universal arrays for use in a method set forth herein. The solid supports typically used for bead arrays can be used without beads. For example, nucleic acids, such as probes or primers can be attached directly to the wells or to gel material in wells. Thus, the above references are illustrative of materials, compositions or apparatus that can be modified for use in the methods and compositions set forth herein.

Accordingly, the instant methods can employ an array of beads, wherein different nucleic acid probes are attached to different beads in the array. In this embodiment, each bead can be attached to a different nucleic acid probe and the beads can be randomly distributed on the solid support in order to effectively attach the different nucleic acid probes to the solid support. Optionally, the solid support can include wells having dimensions that accommodate no more than a single bead. In such a configuration, the beads may be attached to the wells due to forces resulting from the fit of the beads in the wells. As described elsewhere herein, it is also possible to use attachment chemistries or capture materials (e.g., liquid electrical tape) to adhere or otherwise stably associate the beads with a solid support, optionally including holding the beads in wells that may or may not be present on a solid support.

Nucleic acid probes that are attached to beads can include barcode sequences. A population of the beads can be configured such that each bead is attached to only one type of barcode (e.g., a spatial barcode) and many different beads each with a different barcode are present in the population. In this embodiment, randomly distributing the beads to a solid support will result in randomly locating the nucleic acid probe-presenting beads (and their respective barcode sequences) on the solid support. In some cases, there can be multiple beads with the same barcode sequence such that there is redundancy in the population. However, randomly distributing a redundancy-comprising population of beads on a solid support—especially one that has a capacity that is greater than the number of unique barcodes in the bead population—will tend to result in redundancy of barcodes on the solid support, which will tend to reduce image resolution in the context of the instant disclosure (i.e., where the precise location of a barcoded bead cannot be resolved due to redundancy of barcode use within an arrayed population of beads, it is contemplated that such redundant locations will simply be eliminated from an ultimate image produced by methods of the instant disclosure, or other modes of adjustment (e.g., normalization and/or averaging of values) may also be employed to address such redundancies). Alternatively, in preferred embodiments, the number of different barcodes in a population of beads can exceed the capacity of the solid support in order to produce an array that is not redundant with respect to the population of barcodes on the solid support. The capacity of the solid support will be determined in some embodiments by the number of features (e.g. single-bead occupancy wells) that attach or otherwise accommodate a bead.

A bead or other nucleic acid-presenting solid support of the instant disclosure can include, or can be made by the methods set forth herein to attach, a plurality of different nucleic acid probes. For example, a bead or other nucleic acid-presenting solid support can include at least 10, 100, $1 \times 10^3$, $1 \times 10^4$, $1 \times 10^5$, $1 \times 10^6$, $1 \times 10^7$, $1 \times 10^8$, $1 \times 10^9$ or more different probes. Alternatively or additionally, a bead or other nucleic acid-presenting solid support can include at most $1 \times 10^9$, $1 \times 10^8$, $1 \times 10^7$, $1 \times 10^6$, $1 \times 10^5$, $1 \times 10^4$, $1 \times 10^3$, 100, or fewer different probes. It will be understood that each of the different probes can be present in several copies, for example, when the probes have been amplified to form a cluster. Thus, the above ranges can describe the number of different nucleic acid clusters on a bead or other nucleic acid-presenting solid support of the instant disclosure. It will also be understood that the above ranges can describe the number of different barcodes, target capture sequences, or other sequence elements set forth herein as being unique (or sufficiently unique) to particular nucleic acid probes. Alternatively or additionally, the ranges can describe the number of extended probes or modified probes created on a bead or other nucleic acid-presenting solid support of the instant disclosure using a method set forth herein.

Features may be present on a bead or other solid support of the instant disclosure prior to contacting the bead or other solid support with nucleic acid probes. For example, in embodiments where probes are attached to a bead or other solid support via hybridization to primers, the primers can be attached at the features, whereas interstitial areas outside of the features substantially lack any of the primers. Nucleic acid probes can be captured at preformed features on a bead or other solid support, and optionally amplified on the bead or other solid support, e.g., using methods set forth in U.S. Pat. Nos. 8,895,249 and 8,778,849 and/or U.S. Patent Publication No. 2014/0243224 A1, each of which is incorporated herein by reference. Alternatively, a bead or other solid support may have a lawn of primers or may otherwise lack features. In this case, a feature can be formed by virtue of attachment of a nucleic acid probe on the bead or other solid support. Optionally, the captured nucleic acid probe can be amplified on the bead or other solid support such that the resulting cluster becomes a feature. Although attachment is exemplified above as capture between a primer and a complementary portion of a probe, it will be understood that capture moieties other than primers can be present at pre-formed features or as a lawn. Other exemplary capture moieties include, but are not limited to, chemical moieties capable of reacting with a nucleic acid probe to create a covalent bond or receptors capable of binding non-covalently to a ligand on a nucleic acid probe.

A step of attaching nucleic acid probes to a bead or other solid support can be carried out by providing a fluid that contains a mixture of different nucleic acid probes and contacting this fluidic mixture with the bead or other solid support. The contact can result in the fluidic mixture being in contact with a surface to which many different nucleic acid probes from the fluidic mixture will attach. Thus, the probes have random access to the surface (whether the surface has pre-formed features configured to attach the probes or a uniform surface configured for attachment). Accordingly, the probes can be randomly located on the bead or other solid support.

The total number and variety of different probes that end up attached to a surface can be selected for a particular application or use. For example, in embodiments where a fluidic mixture of different nucleic acid probes is contacted with a bead or other solid support for purposes of attaching the probes to the support, the number of different probe species can exceed the occupancy of the bead or other solid support for probes. Thus, the number and variety of different probes that attach to the bead or other solid support can be equivalent to the probe occupancy of the bead or other solid support.

Alternatively, the number and variety of different probe species on the bead or other solid support can be less than the occupancy (i.e. there will be redundancy of probe species such that the bead or other solid support may contain multiple features having the same probe species). Such redundancy can be achieved, for example, by contacting the bead or other solid support with a fluidic mixture that contains a number and variety of probe species that is substantially lower than the probe occupancy of the bead or other solid support.

Attachment of the nucleic acid probes can be mediated by hybridization of the nucleic acid probes to complementary primers that are attached to the bead or other solid support, chemical bond formation between a reactive moiety on the nucleic acid probe and the bead or other solid support (examples are set forth in U.S. Pat. Nos. 8,895,249 and 8,778,849, and in U.S. Patent Publication No. 2014/0243224 A1, each of which is incorporated herein by reference), affinity interactions of a moiety on the nucleic acid probe with a bead- or other solid support-bound moiety (e.g. between known receptor-ligand pairs such as streptavidin-biotin, antibody-epitope, lectin-carbohydrate and the like), physical interactions of the nucleic acid probes with the bead or other solid support (e.g. hydrogen bonding, ionic forces, van der Waals forces and the like), or other interactions known in the art to attach nucleic acids to surfaces.

In some embodiments, attachment of a nucleic acid probe is non-specific with regard to any sequence differences between the nucleic acid probe and other nucleic acid probes that are or will be attached to the bead or other solid support. For example, different probes can have a universal sequence that complements surface-attached primers or the different probes can have a common moiety that mediates attachment to the surface. Alternatively, each of the different probes (or a subpopulation of different probes) can have a unique (or sufficiently unique) sequence that complements a unique (or sufficiently unique) primer on the bead or other solid support or they can have a unique (or sufficiently unique) moiety that interacts with one or more different reactive moiety on the bead or other solid support. In such cases, the unique (or sufficiently unique) primers or unique (or sufficiently unique) moieties can, optionally, be attached at predefined locations in order to selectively capture particular probes, or particular types of probes, at the respective predefined locations.

One or more features on a bead or other solid support can each include a single molecule of a particular probe. The features can be configured, in some embodiments, to accommodate no more than a single nucleic acid probe molecule. However, whether or not the feature can accommodate more than one nucleic acid probe molecule, the feature may nonetheless include no more than a single nucleic acid probe molecule. Alternatively, an individual feature can include a plurality of nucleic acid probe molecules, for example, an ensemble of nucleic acid probe molecules having the same sequence as each other. In particular embodiments, the ensemble can be produced by amplification from a single nucleic acid probe template to produce amplicons, for example, as a cluster attached to the surface.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution, for example, when features of an array are capable of containing amplicons in a volume having a desired capacity. In certain embodiments, an amplification technique used in a method of the present disclosure will be carried out on solid phase. For example, one or more primer species (e.g. universal primers for one or more universal primer binding site present in a nucleic acid probe) can be attached to a bead or other solid support. In PCR embodiments, one or both of the primers used for amplification can be attached to a bead or other solid support (e.g. via a gel). Formats that utilize two species of primers attached to a bead or other solid support are often referred to as bridge amplification because double stranded amplicons form a bridge-like structure between the two surface attached primers that flank the template sequence that has been copied. Exemplary reagents and conditions that can be used for bridge amplification are described, for example, in U.S. Pat. Nos. 5,641,658; 7,115,400; and 8,895,249; and/or U.S. Patent Publication Nos. 2002/0055100 A1, 2004/0096853 A1, 2004/0002090 A1, 2007/0128624 A1 and 2008/0009420 A1, each of which is incorporated herein by reference. Solid-phase PCR amplification can also be carried out with one of the amplification primers attached to a bead or other solid support and the second primer in solution. An exemplary format that uses a combination of a surface attached primer and soluble primer is the format used in emulsion PCR as described, for example, in Dressman et al., Proc. Natl. Acad. Sci. USA 100:8817-8822 (2003), WO 05/010145, or U.S. Patent Publication Nos. 2005/0130173 A1 or 2005/0064460 A1, each of which is incorporated herein by reference. Emulsion PCR is illustrative of the format and it will be understood that for purposes of the methods set forth herein the use of an emulsion is optional and indeed for several embodiments an emulsion is not used.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and U.S. Patent Publication No. 2007/0099208 A1, each of which is incorporated herein by reference. Primers used for RCA can be in solution or attached to a bead or other solid support. The primers can be one or more of the universal primers described herein.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a bead or other solid support at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a bead or other solid support (e.g. universal primers). In this example, amplicons produced after the combined RCA and MDA steps will be attached to the bead or other solid support.

Nucleic acid probes that are used in a method set forth herein or present in an apparatus or composition of the present disclosure can include barcode sequences, and for embodiments that include a plurality of different nucleic acid probes, each of the probes can include a different barcode sequence from other probes in the plurality. Barcode sequences can be any of a variety of lengths.

Longer sequences can generally accommodate a larger number and variety of barcodes for a population. Generally, all probes in a plurality will have the same length barcode (albeit with different sequences), but it is also possible to use different length barcodes for different probes. A barcode sequence can be at least 2, 4, 6, 8, 10, 12, 15, 20 or more nucleotides in length. Alternatively or additionally, the length of the barcode sequence can be at most 20, 15, 12, 10, 8, 6, 4 or fewer nucleotides. Examples of barcode sequences that can be used are set forth, for example in, U.S. Patent Publication No. 2014/0342921 A1 and U.S. Pat. No. 8,460,865, each of which is incorporated herein by reference.

A method of the present disclosure can include a step of performing a nucleic acid detection reaction on a bead or other solid support to determine barcode sequences of nucleic acid probes that are located on the bead or other solid support. In many embodiments the probes are randomly located on the bead or other solid support and the nucleic acid detection reaction provides information to locate each of the different probes. Exemplary nucleic acid detection methods include, but are not limited to nucleic acid sequencing of a probe, hybridization of nucleic acids to a probe, ligation of nucleic acids that are hybridized to a probe, extension of nucleic acids that are hybridized to a probe, extension of a first nucleic acid that is hybridized to a probe followed by ligation of the extended nucleic acid to a second nucleic acid that is hybridized to the probe, or other methods known in the art such as those set forth in U.S. Pat. No. 8,288,103 or 8,486,625, each of which is incorporated herein by reference.

Sequencing techniques, such as sequencing-by-synthesis (SBS) techniques, are a useful method for determining barcode sequences. SBS can be carried out as follows. To initiate a first SBS cycle, one or more labeled nucleotides, DNA polymerase, SBS primers etc., can be contacted with one or more features on a bead or other solid support (e.g. feature(s) where nucleic acid probes are attached to the bead or other solid support). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the bead or other solid support (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., Nature 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and U.S. Patent Publication No. 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 1 1 (1), 3-1 1 (2001); Ronaghi et al. Science 281 (5375), 363 (1998); or U.S. Pat. Nos. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system.

Excitation radiation sources used for fluorescence based detection systems are not necessary for pyrosequencing procedures. Useful fluidic systems, detectors and procedures that can be used for application of pyrosequencing to apparatus, compositions or methods of the present disclosure are described, for example, in PCT Patent Publication No. WO2012/058096, US Patent Publication No. 2005/0191698 A1, or U.S. Pat. No. 7,595,883 or 7,244,559, each of which is incorporated herein by reference.

Sequencing-by-ligation reactions are also useful including, for example, those described in Shendure et al. Science 309:1728-1732 (2005); or U.S. Pat. No. 5,599,675 or 5,750,341, each of which is incorporated herein by reference. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251 (4995), 767-773 (1995); or PCT Publication No. WO 1989/10977, each of which is incorporated herein by reference. In both sequencing-by-ligation and sequencing-by-hybridization procedures, target nucleic acids (or amplicons thereof) that are present at sites of an array are subjected to repeated cycles of oligonucleotide delivery and detection. Compositions, apparatus or methods set forth herein or in references cited herein can be readily adapted for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some sequencing embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero-mode waveguides (ZMWs). Techniques and reagents for FRET-based sequencing are described, for example, in Levene et al. Science 299, 682-686 (2003); Lundquist et al. Opt. Lett. 33, 1026-1028 (2008); and Korlach et al. Proc. Natl. Acad. Sci. USA 105, 1 176-1 181 (2008), each of which is incorporated herein by reference.

Some sequencing embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies and Thermo Fisher subsidiary) or sequencing methods and systems described in U.S. Patent Publication Nos. 2009/0026082 A1; 2009/0127589 A1; 2010/0137143 A1; or U.S. Publication No. 2010/0282617 A1, each of which is incorporated herein by reference.

Nucleic acid hybridization techniques are also useful method for determining barcode sequences. In some cases combinatorial hybridization methods can be used such as those used for decoding of multiplex bead arrays (see, e.g., U.S. Pat. No. 8,460,865, which is incorporated herein by reference). Such methods utilize labelled nucleic acid decoder probes that are complementary to at least a portion of a barcode sequence. A hybridization reaction can be carried out using decoder probes having known labels such that the location where the labels end up on the bead or other solid support identifies the nucleic acid probes according to rules of nucleic acid complementarity. In some cases, pools of many different probes with distinguishable labels are used, thereby allowing a multiplex decoding operation. The number of different barcodes determined in a decoding operation can exceed the number of labels used for the decoding operation. For example, decoding can be carried out in several stages where each stage constitutes hybridization with a different pool of decoder probes. The same decoder probes can be present in different pools but the label that is present on each decoder probe can differ from pool to pool (i.e. each decoder probe is in a different "state" when in different pools).

Various combinations of these states and stages can be used to expand the number of barcodes that can be decoded well beyond the number of distinct labels available for decoding. Such combinatorial methods are set forth in further detail in U.S. Pat. No. 8,460,865 or Gunderson et al., Genome Research 14:870-877 (2004), each of which is incorporated herein by reference.

A method of the present disclosure can include a step of contacting a biological specimen (i.e., a cryosectioned tissue sample) with a bead or other solid support that has nucleic acid probes attached thereto. In some embodiments, the nucleic acid probes are randomly located on the bead or other solid support. The identity and location of the nucleic acid probes may have been decoded prior to contacting the biological specimen with the bead or other solid support.

Alternatively, the identity and location of the nucleic acid probes can be determined after contacting the bead or other solid support with the biological specimen.

Bead-Attached Oligonucleotides

Certain aspects of the instant disclosure employ a nucleotide- or oligonucleotide-adorned bead, where the bead-attached oligonucleotide includes one or more of the following: a linker; an identical sequence for use as a sequencing priming site; a uniform or near-uniform nucleotide or oligonucleotide sequence; a Unique Molecular Identifier which differs for each priming site; an oligonucleotide redundant sequence for capturing polyadenylated mRNAs and priming reverse transcription (i.e., a poly-T sequence); and at least one oligonucleotide barcode which provides an substrate for spatial identification of an individual bead's position within a bead array. Exemplified bead-attached oligonucleotides of the instant disclosure include an oligonucleotide spatial barcode designed to be unique to each bead within a bead array (or at least wherein the majority of such barcodes are unique to a bead within a bead array— e.g., it is expressly contemplated here and elsewhere herein that a bead array possessing only a small fraction of beads (e.g., even up to 10%, 20%, 30% or 40% or more of total beads) having non-unique spatial barcodes (e.g., attributable to a relative lack of degeneracy within the bead population, e.g., due to a probabilistically determinable lack of sequence degeneracy calculated as possible within the bead population, as then compared to the number of sites across which the bead population is ultimately distributed and/or due to an artifact such as non-randomness of bead association occurring during pool-and-split rounds of oligonucleotide synthesis, etc.) could still yield high resolution transcriptome expression images, even while removing (or otherwise adjusting for) any beads that turn out to be redundant in barcode within the array). This spatial barcode provides a substrate for identification. Exemplified bead-attached oligonucleotides of the instant disclosure also include a linker (optionally a cleavable linker); a poly-dT sequence (herein, as a 3' tail); a Unique Molecular Identifier (UMI) which differs for each priming site (as described below and as known in the art, e.g., see WO 2016/040476); a spatial barcode as described above and elsewhere herein; and a common sequence ("PCR handle") to enable PCR amplification after "single-cell transcriptomes attached to microparticles" (STAMP) formation. As set forth in WO 2016/040476, mRNAs bind to poly-dT-presenting primers on their companion microparticle. At steps where mRNA sequence is to be identified, the mRNAs are reverse-transcribed into cDNAs, generating a set of beads called STAMPs. The barcoded STAMPs can then be amplified in pools for high-throughput mRNA-seq to analyze any desired number of beads (where each bead roughly corresponds to an approximately bead-sized area of cellular transcriptomes derived from the cryosectioned tissue sample (in the instant disclosure, 10 μm beads were used to produce resolutions approximating single cell feature sizes, as exemplified herein).

It is expressly contemplated that, instead of or in addition to the above-referenced poly-dT-presenting primers, oligonucleotide sequences designed for capture of a broader range of macromolecules as described here and elsewhere herein, can be used. In particular, oligonucleotide-directed capture of other types of macromolecules is also contemplated for the bead-attached oligonucleotides of the instant disclosure; for instance, a gene-specific capture sequence can be incorporated into oligonucleotide sequences (e.g., for purpose of capturing a full range of cell/tissue-associated RNAs including non-poly-A-tailed RNAs, such as tRNAs, miRNAs, etc., or for purpose of specifically capturing DNAs) and/or a loaded transposase can be used to capture, for example, DNA, and/or a specific sequence can be included to allow for specific capture of a DNA-barcoded antibody signal (not only allowing for assessment of protein distribution across a test sample using the compositions and methods of the instant disclosure, but also thereby, e.g., allowing for linkage of the spatial distributions of proteins to RNA expression).

Exemplary split-and-pool synthesis of the bead barcode: To generate the cell barcode, the pool of microparticles (here, microbeads) is repeatedly split into four equally sized oligonucleotide synthesis reactions, to which one of the four DNA bases is added, and then pooled together after each cycle, in a total of 12 split-pool cycles. The barcode synthesized on any individual bead reflects that bead's unique (or sufficiently unique) path through the series of synthesis reactions. The result is a pool of microparticles, each possessing one of $4^{12}$ (16,777,216) possible sequences on its entire complement of primers. Extension of the split-pool process can provide for, e.g., production of an even greater number of possible spatial barcode sequences for use in the compositions and methods of the instant disclosure. However, as noted above, functional use of spatial barcodes does not require complete non-redundancy of spatial barcodes among all beads of a bead array. Rather, provided that the majority of such barcodes are unique to a bead within a bead array, it is expressly contemplated that a bead array possessing only a small fraction of beads (e.g., even up to 10%, 20%, 30% or 40% or more of total beads) having non-unique spatial barcodes (e.g., attributable to an artifact such as non-randomness of bead association having occurred during pool-and-split rounds of oligonucleotide synthesis, or simply to the likelihood that an array of a million beads derived from a ten million-fold complex library would still be expected to include a number of beads having redundant spatial barcodes in pairwise comparisons) could still yield high resolution transcriptome expression images, where removal or other adjustment (averaging or other such adjustment) of any beads that turn out to be redundant in barcode within the array could be simply performed, e.g., during in silico spatial location assignment and/or image generation.

Exemplary synthesis of a unique molecular identifier (UMI). Following the completion of the "split-and-pool" synthesis cycles described above for generation of spatial barcodes, all microparticles are together subjected to eight rounds of degenerate synthesis with all four DNA bases available during each cycle, such that each individual primer receives one of $4^8$ (65,536) possible sequences (UMIs). A UMI is thereby provided that allows distinguishing between, e.g., individual bead-attached oligonucleotides upon the same bead which otherwise share a common spatial barcode (being that such oligonucleotides are attached to the same bead and therefore receive the same spatial barcode).

In some embodiments of the instant disclosure, the linker of a bead-attached oligonucleotide is a chemically-cleavable, straight-chain polymer. Optionally, the linker is a photolabile optionally substituted hydrocarbon polymer. In certain embodiments, the linker of a bead-attached oligonucleotide is a non-cleavable, straight-chain polymer. Optionally, the linker is a non-cleavable, optionally substituted hydrocarbon polymer. In certain embodiments, the linker is a polyethylene glycol. In one embodiment, the linker is a PEG-C3 to PEG-24.

A nucleic acid probe used in a composition or method set forth herein can include a target capture moiety. In particular embodiments, the target capture moiety is a target capture sequence. The target capture sequence is generally complementary to a target sequence such that target capture occurs by formation of a probe-target hybrid complex. A target capture sequence can be any of a variety of lengths including, for example, lengths exemplified above in the context of barcode sequences.

In certain embodiments, a plurality of different nucleic acid probes can include different target capture sequences that hybridize to different target nucleic acid sequences from a biological specimen. Different target capture sequences can be used to selectively bind to one or more desired target nucleic acids from a biological specimen. In some cases, the different nucleic acid probes can include a target capture sequence that is common to all or a subset of the probes on a solid support. For example, the nucleic acid probes on a solid support can have a poly A or poly T sequence. Such probes or amplicons thereof can hybridize to mRNA molecules, cDNA molecules or amplicons thereof that have poly A or poly T tails. Although the mRNA or cDNA species will have different target sequences, capture will be mediated by the common poly A or poly T sequence regions.

Any of a variety of target nucleic acids can be captured and analyzed in a method set forth herein including, but not limited to, messenger RNA (mRNA), copy DNA (cDNA), genomic DNA (gDNA), ribosomal RNA (rRNA) or transfer RNA (tRNA). Particular target sequences can be selected from databases and appropriate capture sequences designed using techniques and databases known in the art.

A method set forth herein can include a step of hybridizing nucleic acid probes, that are on a supported bead array, to target nucleic acids that are from portions of the biological specimen that are proximal to the probes. Generally, a target nucleic acid will flow or diffuse from a region of the biological specimen to an area of the probe-presenting bead array that is in proximity with that region of the specimen. Here the target nucleic acid will interact with nucleic acid probes that are proximal to the region of the specimen from which the target nucleic acid was released. A target-probe hybrid complex can form where the target nucleic acid encounters a complementary target capture sequence on a nucleic acid probe. The location of the target-probe hybrid complex will generally correlate with the region of the biological specimen from where the target nucleic acid was derived. In certain embodiments, the beads will include a plurality of nucleic acid probes, the biological specimen will release a plurality of target nucleic acids and a plurality of target-probe hybrids will be formed on the beads. The sequences of the target nucleic acids and their locations on the bead array will provide spatial information about the nucleic acid content of the biological specimen. Although the example above is described in the context of target nucleic acids that are released from a biological specimen, it will be understood that the target nucleic acids need not be released. Rather, the target nucleic acids may remain in contact with the biological specimen, for example, when they are attached to an exposed surface of the biological specimen in a way that the target nucleic acids can also bind to appropriate nucleic acid probes on the beads.

A method of the present disclosure can include a step of extending bead-attached probes to which target nucleic acids are hybridized. In embodiments where the probes include barcode sequences, the resulting extended probes will include the barcode sequences and sequences from the target nucleic acids (albeit in complementary form). The extended probes are thus spatially tagged versions of the target nucleic acids from the biological specimen. The sequences of the extended probes identify what nucleic acids are in the biological specimen and where in the biological specimen the target nucleic acids are located. It will be understood that other sequence elements that are present in the nucleic acid probes can also be included in the extended probes (see, e.g., description as provided elsewhere herein). Such elements include, for example, primer binding sites, cleavage sites, other tag sequences (e.g. sample identification tags), capture sequences, recognition sites for nucleic acid binding proteins or nucleic acid enzymes, or the like.

Extension of probes can be carried out using methods exemplified herein or otherwise known in the art for amplification of nucleic acids or sequencing of nucleic acids. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended. In some embodiments, a DNA primer is extended by a reverse transcriptase using an RNA template, thereby producing a cDNA. Thus, an extended probe made in a method set forth herein can be a reverse transcribed DNA molecule. Exemplary methods for extending nucleic acids are set forth in US Pat. App. Publ. No. US 2005/0037393 A1 or U.S. Pat. No. 8,288,103 or 8,486,625, each of which is incorporated herein by reference.

All or part of a target nucleic acid that is hybridized to a nucleic acid probe can be copied by extension. For example, an extended probe can include at least, 1, 2, 5, 10, 25, 50, 100, 200, 500, 1000 or more nucleotides that are copied from a target nucleic acid. The length of the extension product can be controlled, for example, using reversibly terminated nucleotides in the extension reaction and running a limited number of extension cycles. The cycles can be run as exemplified for SBS techniques and the use of labeled nucleotides is not necessary.

Accordingly, an extended probe produced in a method set forth herein can include no more than 1000, 500, 200, 100, 50, 25, 10, 5, 2 or 1 nucleotides that are copied from a target nucleic acid. Of course extended probes can be any length within or outside of the ranges set forth above.

It will be understood that probes used in a method, composition or apparatus set forth herein need not be nucleic acids. Other molecules can be used such as proteins, carbohydrates, small molecules, particles or the like. Probes can be a combination of a nucleic acid component (e.g. having a barcode, primer binding site, cleavage site and/or other sequence element set forth herein) and another moiety (e.g. a moiety that captures or modifies a target nucleic acid).

A method set forth herein can further include a step of acquiring an image of a biological specimen that is in contact with a bead array. The solid support can be in any of a variety of states set forth herein. For example, the bead array can include attached nucleic acid probes or clusters derived from attached nucleic acid probes.

A method of the present disclosure can further include a step of removing one or more extended probes from a bead. In particular embodiments, the probes will have included a cleavage site such that the product of extending the probes will also include the cleavage site. Alternatively, a cleavage site can be introduced into a probe during a modification step. For example a cleavage site can be introduced into an extended probe during the extension step.

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g. from New England Biolabs, Beverley MA; ThermoFisher, Waltham, MA or Sigma Aldrich, St. Louis MO). A particularly useful endonuclease will break a bond in a nucleic acid strand at a site that is 3-remote to its binding site in the nucleic acid, examples of which include Type II or Type I is restriction endonucleases. In some embodiments an endonuclease will cut only one strand in a duplex nucleic acid (e.g. a nicking enzyme). Examples of endonucleases that cleave only one strand include Nt.BstNBI and Nt.Alwl.

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. Abasic sites can be created by hydrolysis of nucleotide residues using chemical or enzymatic reagents. Once formed, abasic sites may be cleaved (e.g. by treatment with an endonuclease or other single-stranded cleaving enzyme, exposure to heat or alkali), providing a means for site-specific cleavage of a nucleic acid. An abasic site may be created at a uracil nucleotide on one strand of a nucleic acid. The enzyme uracil DNA glycosylase (UDG) may be used to remove the uracil base, generating an abasic site on the strand. The nucleic acid strand that has the abasic site may then be cleaved at the abasic site by treatment with endonuclease (e.g. EndoIV endonuclease, AP lyase, FPG glycosylase/AP lyase, EndoVIII glycosylase/AP lyase), heat or alkali. In a particular embodiment, the USER™ reagent available from New England Biolabs is used for the creation of a single nucleotide gap at a uracil base in a nucleic acid.

Abasic sites may also be generated at non-natural/modified deoxyribonucleotides other than uracil and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV or AP lyase).

Other examples of cleavage sites and methods that can be used to cleave nucleic acids are set forth, for example, in U.S. Pat. No. 7,960,120, which is incorporated herein by reference.

Modified nucleic acid probes (e.g. extended nucleic acid probes) that are released from a solid support can be pooled to form a fluidic mixture. The mixture can include, for example, at least 10, 100, $1\times10^3$, $1\times10^4$, $1\times10^5$, $1\times10^6$, $1\times10^7$, $1\times10^8$, $1\times10^9$ or more different modified probes. Alternatively or additionally, a fluidic mixture can include at most $1\times10^9$, $1\times10^8$, $1\times10^7$, $1\times10^6$, $1\times10^5$, $1\times10^4$, $1\times10^3$, 100, 10 or fewer different modified probes. The fluidic mixture can be manipulated to allow detection of the modified nucleic acid probes. For example, the modified nucleic acid probes can be separated spatially on a second solid support (i.e. different from the bead array and/or adhered solid support from which the nucleic acid probes were released after having been contacted with a biological specimen and modified), or the probes can be separated temporally in a fluid stream.

Modified nucleic acid probes (e.g. extended nucleic acid probes) can be separated on a bead or other solid support in a capture or detection method commonly employed for microarray-based techniques or nucleic acid sequencing techniques such as those set forth previously and/or otherwise described herein. For example, modified probes can be attached to a microarray by hybridization to complementary nucleic acids. The modified probes can be attached to beads or to a flow cell surface and optionally amplified as is carried out in many nucleic acid sequencing platforms. Modified probes can be separated in a fluid stream using a microfluidic device, droplet manipulation device, or flow cytometer. Typically, detection is carried out on these separation devices, but detection is not necessary in all embodiments.

The number of bead-attached oligonucleotides present upon an individual bead can vary across a wide range, e.g., from tens to thousands, or millions, or more. Due to the transcriptome profiling nature of the instant disclosure, it is generally preferred to pack as many capture oligonucleotides as spatially and sterically (as well as economically) possible onto an individual bead (i.e., thousands, tens of thousands, or more, of oligonucleotides per individual bead), provided that mRNA capture from a contacted tissue is optimized. It is contemplated that optimization of the oligonucleotide-per-bead metric can be readily performed by one of ordinary skill in the art.

It is further expressly contemplated that in addition to the above-described sequence features, oligonucleotides of the instant disclosure can possess any number of other art-recognized features while remaining within the scope of the instant disclosure.

Capture Material

In certain aspects of the instant disclosure, a capture material is employed to associate a bead array with a solid support (e.g., a glass slide). In some embodiments, the capture material is a liquid electrical tape. An exemplary liquid electrical tape of the instant disclosure is Permatex™ liquid electrical tape, which is a weatherproof protectant for wiring and electrical connections. Liquid capture material such as liquid tape can be applied as a liquid, which then dries to a vinyl polymer that resists dirt, dust, chemicals, and moisture, ensuring that applied beads are attached to a capture material-coated slide in a dry condition. Without wishing to be bound by theory, it is believed that one advantage of the instant methods is that the oligonucleotide-coated beads used in certain embodiments of the invention, which are attached to a solid support (e.g., a slide surface via use, e.g., of electrical tape as a capture material) are maintained in a dry state that optimizes transfer of RNA (or other macromolecule) from a cryosection of a tissue to a bead-coated surface (again without wishing to be bound by theory, such transfer is currently believed to occur via capillary action at the scale of the microbead-cryosection interface surface). It is believed that this highly efficient and direct transfer of cellular RNAs (i.e., the transcriptome of cells found within cryosectioned tissues) or other macromolecules to microbeads (where each microbead respectively possesses thousands of oligonucleotides capable of capturing oligoribonucleotides, e.g., transcripts) arrayed upon a solid support—where the transfer occurs upon an otherwise dry surface, therefore limiting and/or eliminating diffusive properties—is what imparts the instant methods and compositions with extremely high resolution (i.e., resolution at 10-50 μm spacing across a two-dimensional image of a section) of assessment of the cellular transcriptomes (or other macromolecules) of assayed tissue sections.

It is contemplated that beads of the instant disclosure can be applied to a capture material-coated solid support, either immediately upon deposit of capture material to the solid support, or following an initial drying period for the capture material. Capture materials of the instant disclosure can be applied by any of a number of methods, including brushed onto the solid support, sprayed onto the solid support, or the like, or via submersion of the solid support in the capture material. For certain forms of liquid capture material, use of a brush top applicator can allow coverage without gaps and can enable access to tight spaces, which offers advantages in certain embodiments over forms of capture material (i.e., tape) that are applied in a non-liquid state.

While liquid electrical tape has been exemplified as a capture material for use in the methods and compositions of the instant disclosure, other capture materials are also contemplated for such use, including any art-recognized glue or other reagent that is (a) spreadable and/or depositable upon a solid surface (e.g., upon a slide, optionally a slide that allows for light transmission through the slide, e.g., a microscope slide) and (b) capable of binding or otherwise capturing a population of beads of 1-100 μm size. Exemplary other capture materials that are expressly contemplated include latex such as cis-1,4-polyisoprene and other rubbers, as well as elastomers (which are generally defined as polymers that possess viscoelasticity (i.e., both viscosity and elasticity), very weak inter-molecular forces, and generally low Young's modulus and high failure strain compared with other materials), including artificial elastomers (e.g., neoprene) and/or silicone elastomers. Acrylate polymers (e.g., scotch tape) are also expressly contemplated, e.g., for use as a capture material of the instant disclosure.

In Situ Sequencing

In certain aspects of the disclosure, in situ sequencing is performed upon a bead array affixed to a surface, which can be performed by any art-recognized mode of parallel (optionally massively parallel) in situ sequencing, examples of which particularly include the previously described SOLiD™ method, which is a sequencing-by-ligation technique that can be performed in situ upon a solid support (refer, e.g., to Voelkerding et al, Clinical Chem., 55-641-658, 2009; U.S. Pat. Nos. 5,912,148; and 6,130,073, which are incorporated herein by reference in their entireties). In certain embodiments of the instant disclosure, such sequencing can be performed upon a bead array present on a standard microscope slide, optionally using a standard microscope fitted with sufficient computing power to track and associate individual sequences during progressive rounds of detection, with their spatial position(s). The instant disclosure also employed custom fluidics, incubation times, enzymatic mixes and imaging setup in performing in situ sequencing.

Tissue Samples and Cryosectioning

In some embodiments, a tissue section is employed. The tissue can be derived from a multicellular organism. Exemplary multicellular organisms include, but are not limited to a mammal, plant, algae, nematode, insect, fish, reptile, amphibian, fungi or *Plasmodium falciparum*. Exemplary species are set forth previously herein or known in the art. The tissue can be freshly excised from an organism or it may have been previously preserved for example by freezing, embedding in a material such as paraffin (e.g. formalin fixed paraffin embedded samples), formalin fixation, infiltration, dehydration or the like. Optionally, a tissue section can be cryosectioned, using techniques and compositions as described herein and as known in the art. As a further option, a tissue can be permeabilized and the cells of the tissue lysed. Any of a variety of art-recognized lysis treatments can be used. Target nucleic acids that are released from a tissue that is permeabilized can be captured by nucleic acid probes, as described herein and as known in the art.

A tissue can be prepared in any convenient or desired way for its use in a method, composition or apparatus herein. Fresh, frozen, fixed or unfixed tissues can be used. A tissue can be fixed or embedded using methods described herein or known in the art.

A tissue sample for use herein, can be fixed by deep freezing at temperature suitable to maintain or preserve the integrity of the tissue structure, e.g. less than −20° C. In another example, a tissue can be prepared using formalin-fixation and paraffin embedding (FFPE) methods which are known in the art. Other fixatives and/or embedding materials can be used as desired. A fixed or embedded tissue sample can be sectioned, i.e. thinly sliced, using known methods. For example, a tissue sample can be sectioned using a chilled microtome or cryostat, set at a temperature suitable to maintain both the structural integrity of the tissue sample and the chemical properties of the nucleic acids in the sample. Exemplary additional fixatives that are expressly contemplated include alcohol fixation (e.g., methanol fixation, ethanol fixation), glutaraldehyde fixation and paraformaldehyde fixation.

In some embodiments, a tissue sample will be treated to remove embedding material (e.g. to remove paraffin or formalin) from the sample prior to release, capture or modification of nucleic acids. This can be achieved by contacting the sample with an appropriate solvent (e.g. xylene and ethanol washes). Treatment can occur prior to contacting the tissue sample with a solid support-captured bead array as set forth herein or the treatment can occur while the tissue sample is on the solid support-captured bead array.

Exemplary methods for manipulating tissues for use with solid supports to which nucleic acids are attached are set forth in US Pat. App. Publ. No. 2014/0066318 A1, which is incorporated herein by reference.

The thickness of a tissue sample or other biological specimen that is contacted with a bead array in a method, composition or apparatus set forth herein can be any suitable thickness desired.

In representative embodiments, the thickness will be at least 0.1 µm, 0.25 µm, 0.5 µm, 0.75 µm, 1 µm, 5 µm, 10 µm, 50 µm, 100 µm or thicker. Alternatively or additionally, the thickness of a tissue sample that is contacted with bead array will be no more than 100 µm, 50 µm, 10 µm, 5 µm, 1 µm, 0.5 µm, 0.25 µm, 0.1 µm or thinner.

A particularly relevant source for a tissue sample is a human being. The sample can be derived from an organ, including for example, an organ of the central nervous system such as brain, brainstem, cerebellum, spinal cord, cranial nerve, or spinal nerve; an organ of the musculoskeletal system such as muscle, bone, tendon or ligament; an organ of the digestive system such as salivary gland, pharynx, esophagus, stomach, small intestine, large intestine, liver, gallbladder or pancreas; an organ of the respiratory system such as larynx, trachea, bronchi, lungs or diaphragm; an organ of the urinary system such as kidney, ureter, bladder or urethra; a reproductive organ such as ovary, fallopian tube, uterus, vagina, placenta, testicle, epididymis, vas deferens, seminal vesicle, prostate, penis or scrotum; an organ of the endocrine system such as pituitary gland, pineal gland, thyroid gland, parathyroid gland, or adrenal gland; an organ of the circulatory system such as heart, artery, vein or capillary; an organ of the lymphatic system such as lymphatic vessel, lymph node, bone marrow, thymus or spleen; a sensory organ such as eye, ear, nose, or tongue; or an organ of the integument such as skin, subcutaneous tissue or mammary gland. In some embodiments, a tissue sample is obtained from a bodily fluid or excreta such as blood, lymph, tears, sweat, saliva, semen, vaginal secretion, ear wax, fecal matter or urine.

A sample from a human can be considered (or suspected) healthy or diseased when used. In some cases, two samples can be used: a first being considered diseased and a second being considered as healthy (e.g. for use as a healthy control). Any of a variety of conditions can be evaluated, including but not limited to, an autoimmune disease, cancer, cystic fibrosis, aneuploidy, pathogenic infection, psychological condition, hepatitis, diabetes, sexually transmitted disease, heart disease, stroke, cardiovascular disease, multiple sclerosis or muscular dystrophy. Certain contemplated conditions include genetic conditions or conditions associated with pathogens having identifiable genetic signatures.

Macromolecules

In addition to the poly-A-tailed RNAs captured by poly-dT sequences in certain exemplified embodiments of the instant disclosure, it is expressly contemplated that the instant compositions and methods can be applied to obtain spatially-resolvable abundance data for a wide range of macromolecules, including not only poly-A-tailed RNAs/transcripts, but also, e.g., non-poly-A-tailed RNAs (e.g., tRNAs, miRNAs, etc.; optionally specifically captured using sequence-specific oligonucleotide sequences), DNAs (including, e.g., capture via gene-specific oligonucleotides, loaded transposases, etc.), and proteins (including, e.g., DNA-barcoded antibodies, optionally where a DNA barcode effectively tags a capture antibody for detection, allowing for direct comparison of spatial distribution(s) of antibodies and/or antibody-captured proteins with spatially-resolvable expression profiling that also can be performed upon the test sample via use of the compositions and methods of the instant disclosure. Accordingly, the range of macromolecules expressly contemplated for capture using the compositions and methods of the instant disclosure includes all forms of RNA (including, e.g., transcripts, tRNAs, rRNAs, miRNAs, etc.), DNAs (including, e.g., genomic DNAs, barcode DNAs, etc.) and proteins (including, e.g., antibodies that are tagged for binding and detection and/or other forms of protein, optionally including proteins captured by antibodies). In one embodiment, proteins can be profiled using a library of DNA-barcoded antibodies to stain a tissue, before capturing proteins on the spatial array (refer to Cellular Indexing of Transcriptome and Epitopes by sequencing (CITE-seq), which combines unbiased genome-wide expression profiling with the measurement of specific protein markers in thousands of single cells using droplet microfluidics. In brief, monoclonal antibodies are conjugated to oligonucleotides containing unique antibody identifier sequences; a cell suspension is then labeled with the oligo-tagged antibodies and single cells are subsequently encapsulated into nanoliter-sized aqueous droplets in a microfluidic apparatus. In each droplet, antibody and cDNA molecules are indexed with the same unique (or sufficiently unique) barcode and are converted into libraries that are amplified independently and mixed in appropriate proportions for sequencing in the same lane. Stoeckius and Smibert. Protocol Exchange (2017) doi: 10.1038/protex.2017.068). Additionally, proteins may be adsorbed onto the beads nonspecifically, or through chemical capture (such as amine reactive chemistry or crosslinkers), the beads may be sorted into wells and the proteins quantitated by standard measures (antibodies, ELISA, etc), and then followed by sequencing of the paired bead sequences and the spatial locations reconstructed.

Application of Wash Solution to Bead Array (Optional)

In certain embodiments, a solid support-captured bead array is washed after exposure of the bead array to a cryosectioned tissue (optionally, the cryosectioned tissue is removed prior to or during application of a wash solution). For example, a solid support-captured bead array of the instant disclosure can be submerged in a buffered salt solution (or other stabilizing solution) after contacting the bead array with a cryosectioned tissue sample. Exemplified buffered salt solutions include saline-sodium citrate (SSC), for example at a NaCl concentration of about 0.2 M to 5 M NaCl, optionally at about 0.5 to 3 M NaCl, optionally at about 1 M NaCl. Without wishing to be bound by theory, as exemplified, exposure of a transcriptome-bound bead array to a saline solution (or other stabilizing solution) is believed to stabilize bead-attached capture probe-sample RNA (i.e., transcript) interactions, likely by blocking RNA degradation and/or other degradative processes. While SSC has been exemplified in the processes of the instant disclosure, use of other types of buffered solutions is expressly contemplated, including, e.g. PBS, Tris buffered saline and/or Tris buffer, as well as, more broadly, any aqueous buffer possessing a pH between 4 and 10 and salt between 0-1 osmolarity.

Wash solutions can contain various additives, such as surfactants (e.g. detergents), enzymes (e.g. proteases and collagenases), cleavage reagents, or the like, to facilitate removal of the specimen. In some embodiments, the solid support is treated with a solution comprising a proteinase enzyme. Alternatively or additionally, the solution can include cellulase, hemicelluase or chitinase enzymes (e.g. if desiring to remove a tissue sample from a plant or fungal source). In some cases, the temperature of a wash solution will be at least 30° C., 35° C., 50° C., 60° C. or 90° C. Conditions can be selected for removal of a biological specimen while not denaturing hybrid complexes formed between target nucleic acids and solid support-attached nucleic acid probes.

Sequencing Methods

Some of the methods and compositions provided herein employ methods of sequencing nucleic acids. A number of DNA sequencing techniques are known in the art, including fluorescence-based sequencing methodologies (See, e.g., Birren et al, Genome Analysis Analyzing DNA, 1, Cold Spring Harbor, N.Y., which is incorporated herein by reference in its entirety). In some embodiments, automated sequencing techniques understood in that art are utilized. In some embodiments, parallel sequencing of partitioned amplicons can be utilized (PCT Publication No WO2006084132, which is incorporated herein by reference in its entirety). In some embodiments, DNA sequencing is achieved by parallel oligonucleotide extension (See, e.g., U.S. Pat. Nos. 5,750,341; 6,306,597, which are incorporated herein by reference in their entireties). Additional examples of sequencing techniques include the Church polony technology (Mitra et al, 2003, Analytical Biochemistry 320, 55-65; Shendure et al, 2005 Science 309, 1728-1732; U.S. Pat. Nos. 6,432,360, 6,485,944, 6,511,803, which are incorporated by reference), the 454 picotiter pyrosequencing technology (Margulies et al, 2005 Nature 437, 376-380; US 20050130173, which are incorporated herein by reference in their entireties), the Solexa single base addition technology (Bennett et al, 2005, Pharmacogenomics, 6, 373-382; U.S. Pat. Nos. 6,787,308; 6,833,246, which are incorporated herein by reference in their entireties), the Lynx massively parallel signature sequencing technology (Brenner et al. (2000). Nat. Biotechnol. 18:630-634; U.S. Pat. Nos. 5,695,934; 5,714,330, which are incorporated herein by reference in their entireties), and the Adessi PCR colony technology (Adessi et al. (2000). Nucleic Acid Res. 28, E87; WO 00018957, which are incorporated herein by reference in their entireties).

Next-generation sequencing (NGS) methods can be employed in certain aspects of the instant disclosure to obtain a high volume of sequence information (such as are particularly required to perform deep sequencing of bead-associated RNAs following capture of RNAs from cryosections) in a highly efficient and cost effective manner. NGS methods share the common feature of massively parallel, high-throughput strategies, with the goal of lower costs in comparison to older sequencing methods (see, e.g., Voelkerding et al, Clinical Chem., 55: 641-658, 2009; MacLean et al, Nature Rev. Microbiol, 7-287-296; which are incorporated herein by reference in their entireties). NGS methods can be broadly divided into those that typically use template amplification and those that do not. Amplification-utilizing methods include pyrosequencing commercialized by Roche as the 454 technology platforms (e.g., GS 20 and GS FLX), the Solexa platform commercialized by Illumina, and the Supported Oligonucleotide Ligation and Detection (SOLiD™) platform commercialized by Applied Biosystems. Non-amplification approaches, also known as single-molecule sequencing, are exemplified by the HeliScope platform commercialized by Helicos Biosciences, SMRT sequencing commercialized by Pacific Biosciences, and emerging platforms marketed by VisiGen and Oxford Nanopore Technologies Ltd.

In pyrosequencing (U.S. Pat. Nos. 6,210,891; 6,258,568, which are incorporated herein by reference in their entireties), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al, Clinical Chem., 55-641-658, 2009; MacLean et al, Nature Rev. Microbiol, 7:287-296; U.S. Pat. Nos. 6,833,246; 7,115,400; 6,969,488, which are incorporated herein by reference in their entireties), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55: 641-658, 2009; U.S. Pat. Nos. 5,912,148; and 6,130,073, which are incorporated herein by reference in their entireties) can initially involve fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al, J. Am. Chem. Soc. 2006 Feb. 8; 128(5): 1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, which are incorporated herein by reference in their entireties). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is approximately 99.6% for 50 base reads, with approximately 100 Mb generated per run. The read-length is 100 base pairs. The accuracy for homopolymer repeats of 5 repeats in length is approximately 98%. The benefits of ion semiconductor sequencing are rapid sequencing speed and low upfront and operating costs.

Imaging/Image Assembly

With spatial barcodes of individual beads identified, and with sequences of those RNAs captured by individual bead-attached oligonucleotides (capture probes) also identified, high-resolution images that localize sites of RNA expression can be readily constructed in silico. In certain embodiments, the spatial locations of a large number of beads within an array can first be assigned to an image location, with all associated RNA sequence (expression) data also assigned to that position (optionally, effectively de-coupling the spatial barcode from the array/matrix of RNA sequence information associated with a given site/bead, once the spatial barcode has been used to assign the RNA sequence information to an array position). High resolution images representing the extent of capture of individual or grouped RNAs/transcripts across the various spatial positions of the arrays can then be generated using the underlying RNA sequence information (which was at least originally bead-associated). Images (i.e., pixel coloring and/or intensities) can be adjusted and/or normalized using any (or any number of) art-recognized technique(s) deemed appropriate by one of ordinary skill in the art.

In certain embodiments, a high-resolution image of the instant disclosure is an image in which discrete features (e.g., pixels) of the image are spaced at 50 µm or less. In some embodiments, the spacing of discrete features within the image is at 40 µm or less, optionally 30 µm or less, optionally 20 µm or less, optionally 15 µm or less, optionally 10 µm or less, optionally 9 µm or less, optionally 8 µm or less, optionally 7 µm or less, optionally 6 µm or less, optionally 5 µm or less, optionally 4 µm or less, optionally 3 µm or less, optionally 2 µm or less, or optionally 1 µm or less.

Images can be obtained using detection devices known in the art. Examples include microscopes configured for light, bright field, dark field, phase contrast, fluorescence, reflection, interference, or confocal imaging. A biological specimen can be stained prior to imaging to provide contrast between different regions or cells. In some embodiments, more than one stain can be used to image different aspects of the specimen (e.g. different regions of a tissue, different cells, specific subcellular components or the like). In other embodiments, a biological specimen can be imaged without staining.

In particular embodiments, a fluorescence microscope (e.g. a confocal fluorescent microscope) can be used to detect a biological specimen that is fluorescent, for example, by virtue of a fluorescent label. Fluorescent specimens can also be imaged using a nucleic acid sequencing device having optics for fluorescent detection such as a Genome Analyzer®, MiSeq®, NextSeq® or HiSeq® platform device commercialized by Illumina, Inc. (San Diego, CA); or a SOLiD™ sequencing platform commercialized by Life Technologies (Carlsbad, CA). Other imaging optics that can be used include those that are found in the detection devices described in Bentley et al., Nature 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and US Pat. App. Publ. No. 2008/0108082, each of which is incorporated herein by reference.

An image of a biological specimen can be obtained at a desired resolution, for example, to distinguish tissues, cells or subcellular components. Accordingly, the resolution can be sufficient to distinguish components of a biological specimen that are separated by at least 0.5 µm, 1 µm, 5 µm, 10 µm, 50 µm, 100 µm, 500 µm, 1 mm or more. Alternatively or additionally, the resolution can be set to distinguish components of a biological specimen that are separated by at least 1 mm, 500 µm, 100 µm, 50 µm, 10 µm, 5 µm, 1 µm, 0.5 µm or less.

A method set forth herein can include a step of correlating locations in an image of a biological specimen with barcode sequences of nucleic acid probes that are attached to individual beads to which the biological specimen is, was or will be contacted. Accordingly, characteristics of the biological specimen that are identifiable in the image can be correlated with the nucleic acids that are found to be present in their proximity. Any of a variety of morphological characteristics can be used in such a correlation, including for example, cell shape, cell size, tissue shape, staining patterns, presence of particular proteins (e.g. as detected by immunohistochemical stains) or other characteristics that are routinely evaluated in pathology or research applications. Accordingly, the biological state of a tissue or its components as determined by visual observation can be correlated with molecular biological characteristics as determined by spatially resolved nucleic acid analysis.

A solid support upon which a biological specimen is imaged can include fiducial markers to facilitate determination of the orientation of the specimen or the image thereof in relation to probes that are attached to the solid support. Exemplary fiducials include, but are not limited to beads (with or without fluorescent moieties or moieties such as nucleic acids to which labeled probes can be bound), fluorescent molecules attached at known or determinable features, or structures that combine morphological shapes with fluorescent moieties. Exemplary fiducials are set forth in US Pat. App. Publ. No. 2002/0150909 A1 or U.S. patent application Ser. No. 14/530,299, each of which is incorporated herein by reference. One or more fiducials are preferably visible while obtaining an image of a biological specimen. Preferably, the solid support includes at least 2, 3, 4, 5, 10, 25, 50, 100 or more fiducial markers. The fiducials can be provided in a pattern, for example, along an outer edge of a solid support or perimeter of a location where a biological specimen resides. In one embodiment, one or more fiducials are detected using the same imaging conditions used to visualize a biological specimen. However if desired separate images can be obtained (e.g. one image of the biological specimen and another image of the fiducials) and the images can be aligned to each other.

Kits

The instant disclosure also provides kits containing agents of this disclosure for use in the methods of the present disclosure. Kits of the instant disclosure may include one or more containers comprising an agent (e.g., a capture material, such as liquid electrical tape) and/or composition (e.g., a slide-captured bead array) of this disclosure. In some embodiments, the kits further include instructions for use in accordance with the methods of this disclosure. In some embodiments, these instructions comprise a description of administration of the agent to diagnose, e.g., a disease and/or malignancy. In some embodiments, the instructions comprise a description of how to create a tissue cryosection, form a spatially-defined (or simply spatially definable, pending performance of a step that defines the spatial resolution of the bead array) bead array, contact a tissue cryosection with a spatially-defined bead array and/or obtain captured, tissue cryosection-derived transcript sequence from the spatially-defined bead array. The kit may further comprise a description of selecting an individual suitable for treatment based on identifying whether that subject has a certain pattern of expression of one or more transcripts in a cryosection sample.

The instructions generally include information as to dosage, dosing schedule, and route of administration for the intended use/treatment. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for staging a cryosection and/or diagnosing a specific expression pattern in a cryosection. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. The container may further comprise a pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Beads:

Beads were produced by the ChemGenes Corporation on one of two polystyrene supports (Agilent and Custom Polystyrene supports from AM Biotech). Beads were used with one of the two following sequences:

```
Sequence 1:
                                            (SEQ ID NO: 1)
5'-PEG Linker-TTTT-PCT-
GCCGGTAATACGACTCACTATAGGGCTACACGACGCTCTTCCGATCTJJJ
JJJTCTTCAGCGTTCCCGAGAJJJJJJJNNNNNNNNT30

Sequence 2:
                                            (SEQ ID NO: 2)
5'-Linker-
TTTTTTTTGCCGGGGCTACACGACGCTCTTCCGATCTJJJJJJJJTCTTC
AGCGTTCCCGAGAJJJJJJJNNNNNNNNT30
```

Here, PCT represents a photocleavable thymidine; J bases represent bases generated by split-pool barcoding, such that every oligo on a given bead has the same J bases; Ns represent bases generated by mixing, so every oligo on a given bead has different N bases; and T30 represents a string of 30 thymidines. The two sequences corresponded to different bead batches, which were not found to differ significantly in terms of the number of transcripts per bead.

Puck Preparation:

Pucks were prepared as follows. Glass coverslips (Bioptechs, 40-1313-0319) were attached to a miniature centrifuge (USA Scientific 2621-0016) using double sided tape. Subsequently, the coverslip was cleaned by spraying with 70% ethanol and wiping with lens paper (VWR 52846-007) A spray-on silicone formulation was then sprayed onto the coverslip, the cover to the minifuge was closed, and the minifuge was turned on for 10 seconds. The minifuge was then turned off and the cover opened, and liquid tape (Performix 24122000) was sprayed onto the coverslip. The minifuge was again closed and turned on for 10 seconds. The coverslip was then carefully removed from the minifuge, and a gasket (Grace Biolabs, CW-50R-1.0) was placed on top of the coverslip and pressed down. Beads were then diluted to a concentration of approximately 100,000 beads/µL in ultrapure water (Thermofisher, 10977015). Beads were pelleted and resuspended twice in ultrapure water, and 10 uL of the resulting solution was pipetted into each position on the gasket. The coverslip-gasket filled with beads was then put into a spinning bucket centrifuge, preheated to 40° C., and centrifuged at 850 g for at least 30 minutes until the surface was dry.

Subsequently, the coverslip was removed from the centrifuge and the gasket was carefully removed. Gentle pipetting of water directly onto the pelleted bead pucks removed all beads except for those directly in contact with the liquid tape layer. Beads removed in this way could be stored at 4° C. for later use. As much water as possible was removed from the resulting pucks, and the pucks were left to dry.

Puck Sequencing:

Puck sequencing was performed using SOLiD™ chemistry in a Bioptechs FCS2 flowcell using a RP-1 peristaltic pump (Rainin), and a modular valve positioner (Hamilton). Flow rates between 1 mL/min and 3 mL/min were typical. Imaging was performed using a Nikon Eclipse Ti microscope with a Yokogawa CSU-W1 confocal scanner unit and an Andor Zyla 4.2 Plus camera. Images were acquired using a Nikon Plan Apo 10×/0.45 objective. After each ligation, four images were acquired: one using a 488 nm laser and a 525/36 emission filter (MVI, 77074803); one using a 561 nm laser and a 582/15 emission filter (MVI, FF01-582/15-25); one using a 561 nm laser and a 624/40 emission filter (MVI, FF01-624/40-25); and one using a 647 nm laser and a 705/72 emission filter (MVI, 77074329). The final stitched images were 6030 pixels by 6030 pixels.

Sequencing consisted of three steps: primer hybridization, ligation, and stripping. During primer hybridization, a primer was flowed into the flowcell at 5 µM concentration in 4×SSC, and was allowed to sit for 20 minutes. Subsequently, the flowcell was washed in 3 mL of SOLiD buffer F. Following instrument buffer wash, ligation mix was flowed into the chamber and allowed to sit for 20 minutes, before being flowed back into its original reservoir. Ligation mix was reused for ~10 ligations, before being replenished. Following ligation, the flowcell was washed again in instrument buffer, and 1.5 mL of SOLiD buffer C was then flowed in, followed by 1.5 mL of SOLiD buffer B, and this step was repeated once again, to cleave the SOLiD sequencing oligo. The flowcell was then washed in instrument buffer and the ligation step was repeated. After the second ligation step, 10 mL of 80% formamide in water was flowed into the flowcell and left for 10 minutes. The flowcell was then washed in instrument buffer, and the process was repeated with the next primer.

Ligation Mix:

1× T4 DNA Ligase Buffer (Enzymatics)
6 U/uL T4 DNA Ligase (Rapid) (Enzymatics)
40× dilution of SOLiD SR-75 sequencing oligo.

Image Processing and Basecalling:

All image processing was performed using a custom-built processing suite in Matlab. Briefly, one image was acquired for puck after each ligation, and each image contained four color channels. First, color channels were co-registered to each other by thresholding the images and maximizing the cross-correlation between the thresholded images. Subsequently, for each puck, the images of each ligation were registered to the image of the first ligation using a SIFT-RANSAC image registration algorithm based on the VLFeat SIFT package in Matlab. Registered images were then basecalled on a pixel-wise basis, as follows. First, the intensities in the Cy3 channel were multiplied by a factor of 0.5 and subtracted from the intensities in the TxR channel, which accounts for cross-talk between the channels which resulted from the excitation of TxR using the 561 nm laser. Furthermore, for even-numbered ligations, the image of the previous ligation was multiplied by a factor of 0.4 and then subtracted on a channel-by-channel basis from the image of the even ligation. Each pixel was then called by intensity. For pucks made using the 180402 bead batch, the expected base balance was further enforced by including an additional step in which the intensities of the dimmest channels were progressively increased until each channel accounted for between 20% and 30% of the pixels in the center of the image.

Beads were subsequently identified from the basecalled images as follows. Each pixel was assigned a number, the base 5 representation of which corresponds to the bases that were called at that pixel on each ligation. Every such number that occurred on at least 50 connected pixels in the image was determined to be a bead, represented by the centroid of the connected cluster.

SOLiD barcodes were then mapped to Illumina barcodes using a custom-built Matlab application that identified the pairwise distance between all members of the two sets of barcodes. Pairs of SOLiD barcodes and Illumina barcodes were saved for further analysis if the two barcodes were separated by at most two edits, and if the mapping between the barcodes was unique, i.e. if there were no other barcodes at equal or lower edit distance to either barcode.

Cell Type Deconvolution:

A probability distribution across cell types was computed per bead using a custom method, implemented in Python, termed NMFreg (Non-Negative Matrix Factorization Regression). The method consisted of two main steps: first, single cell atlas data previously annotated with cell type identities was used to derive a basis in reduced gene space (via NMF), and second, non-negative least squares (NNLS) regression was used to compute the loadings for each bead in this basis. The details of the method are as follows.

As a preprocessing step, highly variable genes from single cell data were selected as in certain prior gene atlas studies. Only these genes were considered for future analysis. Beads were subsequently retained for analysis by NMFreg only if they had 5 transcripts in the set of variable genes. An interpretable low-dimensional basis for the space of highly variable genes was obtained as the set of K factors from performing NMF on the single cell atlas data. Each of the K factors/basis vector was mapped to a unique atlas cell type, yielding interpretability of the basis. The cell type identity of a factor was established as the most frequent cell type of atlas cells with highest loading in this factor.

With the aim of deriving a probability distribution over the atlas cell types for each Slide-seq bead, the beads loadings in the basis were first computed. This was achieved through NNLS regression of the Slide-seq bead by gene expression matrix onto the basis. The resulting bead by K matrix of loadings suffered from the well-known non-identifiability native to NMF, and a scaling of these loadings was customary before further utilizing them. Therefore, each of the K columns of the matrix of loadings was scaled to have L2 norm equal to 1. Afterwards, per bead, a cell type loading was computed as the L2 length of the loadings of all factors mapped to this atlas cell type. This yielded a bead by number of cell types matrix, in which each row was normalized to sum up to one. The result contained the desired probability distribution across cell types for each bead.

For the computation in FIGS. 6A to 6F, rather than requiring that beads had at least 5 transcripts of variable genes, instead beads were required to have at least 100 transcripts. This decreased the number of beads called by 72.6%+/−13.7% (mean+/−std over 7 cerebellar pucks). With this threshold, 56.3%+/−6.3% of beads passed the confidence threshold, a reduction compared to the number of beads that passed the confidence threshold without the 100 transcript filter (see below).

Confidence Thresholding:

The bead factor loadings returned by NMFreg were in general less pure than the factor loadings obtained for single-cell sequencing data, likely reflecting both the sparsity of the Slide-Seq data and RNA contributions of other adjacent cell types. To determine whether a given bead could be confidently assigned to a single cell type, as in FIGS. 6A to 6F and 2C, the L2 length of the vector of factor loadings was first calculated for factors representing the cell type to which the bead was assigned. For each cell-type, the minimum such L2 length appearing among Dropseq beads assigned to that cell type in the atlas data was also identified. The Slide-Seq bead was then said to be assigned confidently to the cell type if the L2 length of cell-type-specific factors for the Slide-Seq bead was at least as large as the smallest L2 length of cell-type-specific factors appearing among Dropseq beads assigned to the same cell type.

Figure 6A:
FIGS. 6A to 6F show features of the beads produced.
Figure 6B:
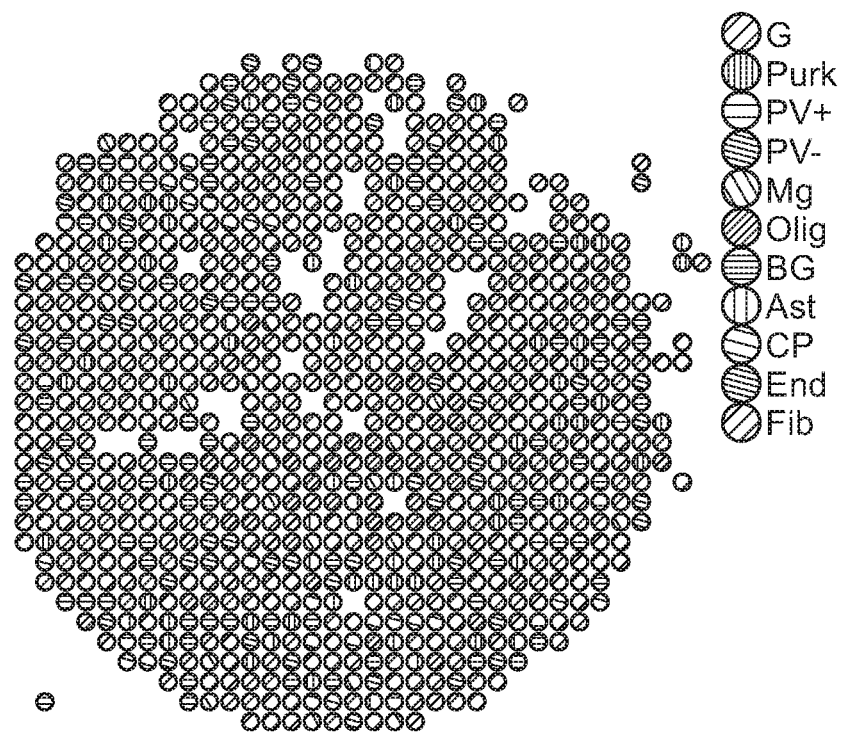
Figure 6C:
Figure 6D:
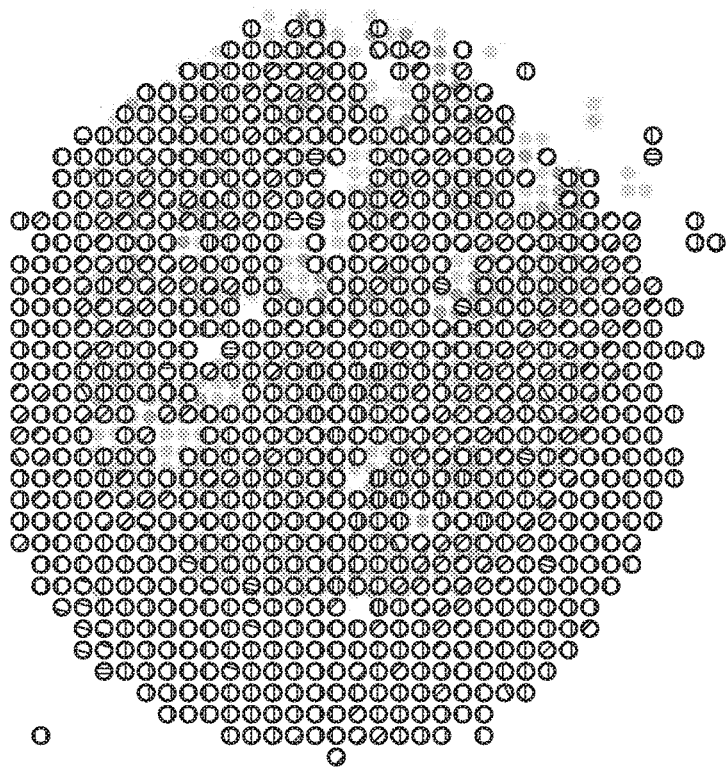
Figure 6E:
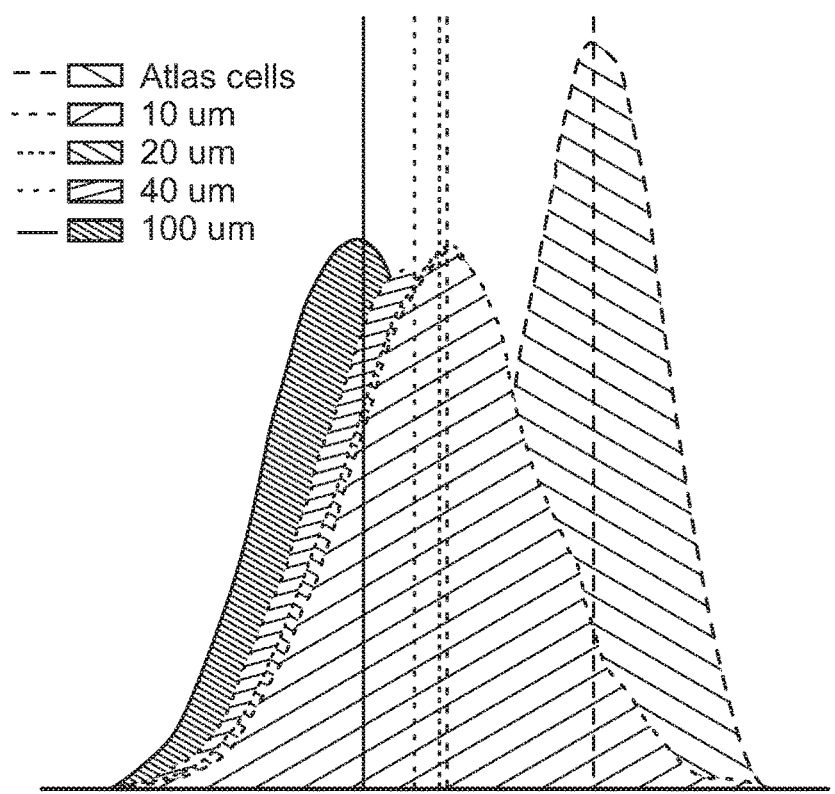
Figure 6F:
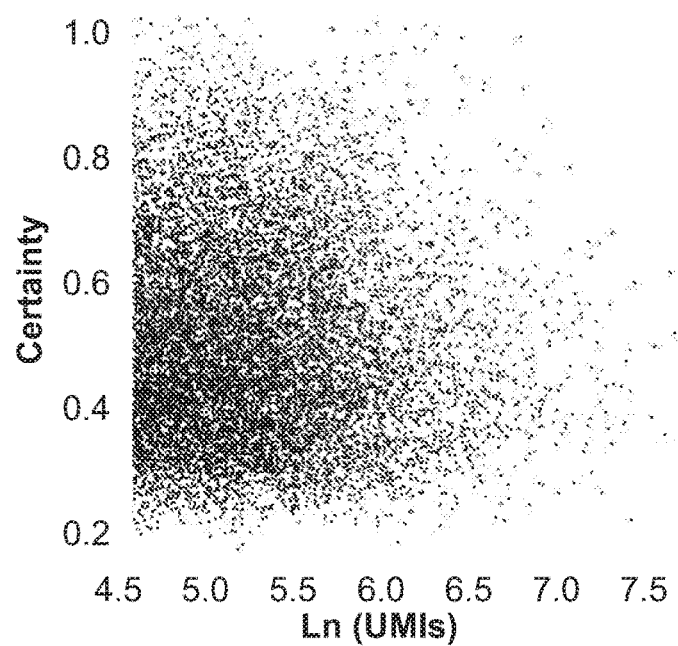
Figure 7A:
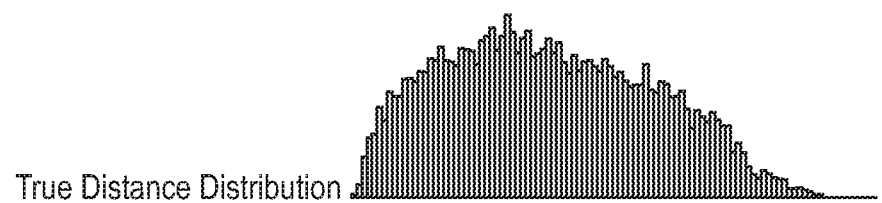
FIGS. 7A to 7E show a schematic of the significant gene calling algorithm employed. The algorithm can be run on any specified subset of beads to identify genes with significant nonrandom distribution within that subset. All images here have been calculated on the subset of granule cells on a coronal cerebellar puck (same puck as in FIG. 3A).
Figure 7B:
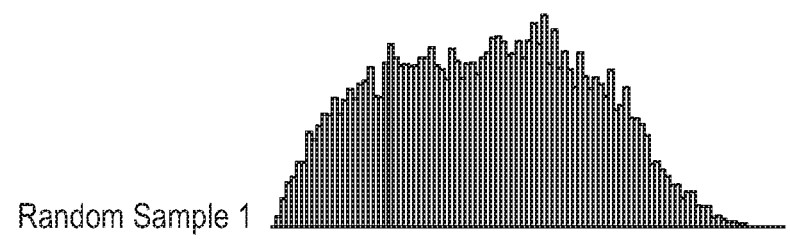
Figure 7B:
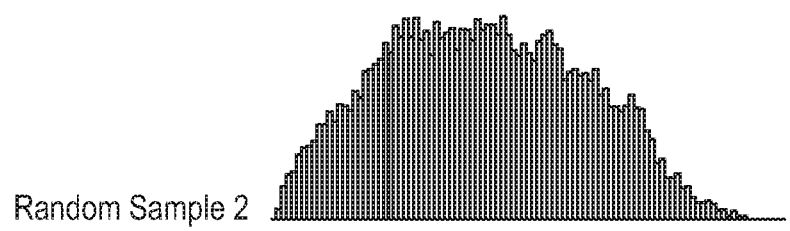
Figure 7B:
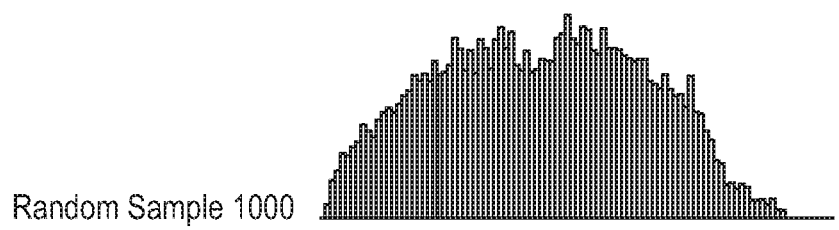
Figure 7B:
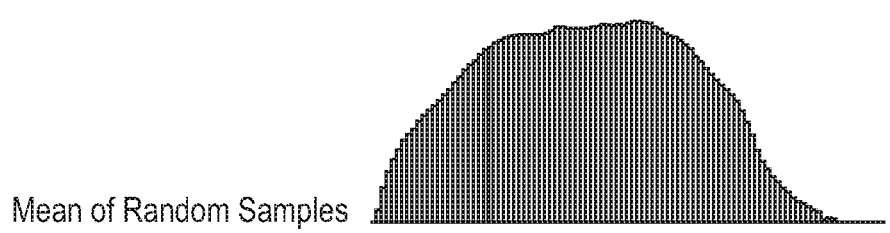
Figure 7C:
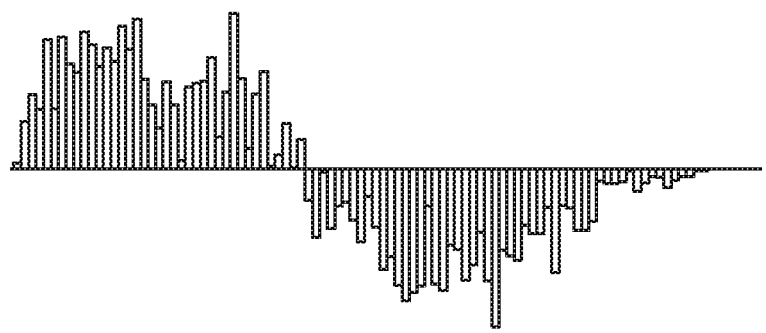
Figure 7D:
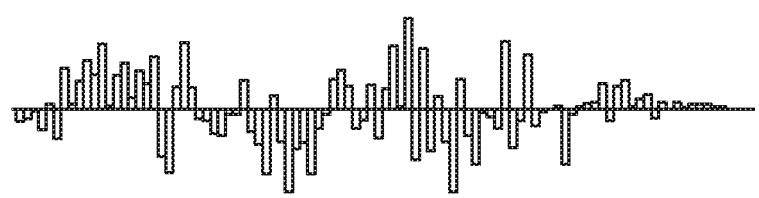
Figure 7D:
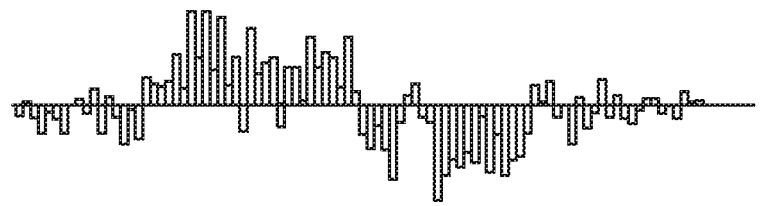
Figure 7D:
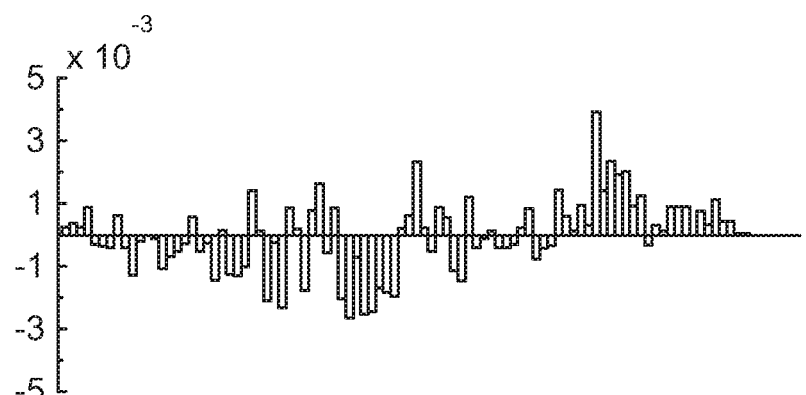
Figure 7E:
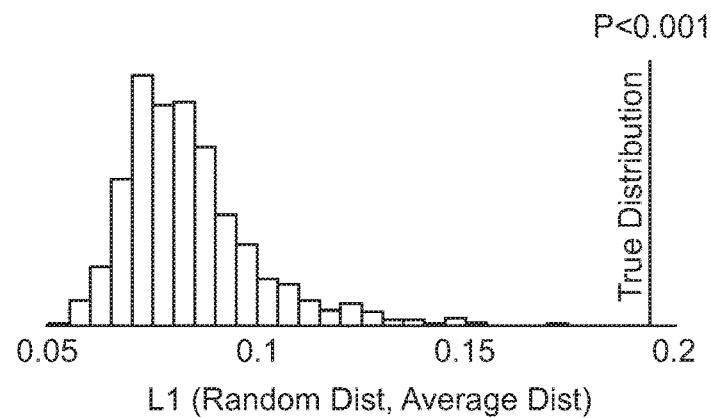

Interestingly, there was no relationship between the number of UMIs per bead and the confidence score of the bead, likely because beads with more UMIs were more likely to have multiple cells on them (FIG. 6F).

Aggregate Cell Type Analysis:

Recall that the diameter of Slide-seq beads is 10 μm (original feature size). In an attempt to investigate the importance of the size of the features, larger beads were generated in silico, hypothesizing what the collected expression signature might be at lower resolutions, i.e. larger feature sizes. The choice of artificial feature sizes (20, 40, 100 μm) reflected the resolution capabilities of alternative technologies for measuring spatial expression signal. Aggregate array features were performed by taking bead centroid locations obtained through SOLiD sequencing and forming a grid of defined size over the locations of the beads. Aggregate features were then treated as beads.

Significant Gene Calling:

Genes were identified as spatially non-random using a custom Matlab application, as follows (see FIGS. 7A to 7E). The set of pairwise Euclidean distances between all beads was calculated. For each cluster, genes were identified as candidates for the statistical significance analysis if they had an expression of at least 0.1 transcripts per bead within that cluster in the atlas reference dataset, or if the variance within that cluster in the atlas reference dataset was at least 0.01 transcripts squared and the ratio of the variance to the squared expression was at least 7.5 (an empirically determined value). Moreover, candidate genes for the statistical significance analysis were required to have at least one transcript on at least 15 beads.

To determine whether a transcript had a significantly non-random spatial distribution within a particular set of beads (for example, within the set of beads called as Purkinje neurons by NMFreg), the distribution of pairwise distances was compared between the beads expressing at least one count of that transcript to the distribution of pairwise distances between an identical number of beads, sampled randomly from all mapped beads on the puck with probability proportional to the total number of transcripts on the bead. (Rigorously, therefore, the spatial significance gene algorithm determined whether the spatial distribution of a particular transcript differed significantly from the spatial distribution of all transcripts.) Specifically, 1000 such random samples were generated, and for each sample the distribution of pairwise distances was calculated. The average distribution of pairwise distances was then calculated, and averages pairwise across all 1000 samples were calculated. Finally, the L1 norm between the distribution of pairwise distances was calculated for each of the 1000 random samples and the average distribution, and the L1 norm between the distribution of pairwise distances was calculated for the true sample of beads and the average distribution. p was defined to be the fraction of random samples having distributions closer to the average distribution (under the L1 norm) than the true sample, and any genes with values p<=0.005 were considered. Due to the very high false-positive rate implied by this p value (often as many as 4000 genes would pass the filters described above, implying ~20 false positives), statistically significant genes were identified as those that showed up consistently across biological replicates.

Overlap Analysis:

To identify genes that were significantly correlated or anticorrelated with other genes, a custom Matlab algorithm was applied, as follows. For simplicity of description, the case of determining the genes that were correlated or anti-correlated with a particular gene, gene A was considered. For each gene in the genome, a "true" image was generated in which each bead with at least one transcript of the gene was represented by a square of side length 100 pixels (~64 microns). Then, for each gene, 50 "random" images were additionally generated in which the same number of transcripts were redistributed across all beads with probability proportional to the number of reads per bead. The element-wise inner product was then calculated between the image of gene A and the 50 random images every other gene, and the mean and standard deviation of the inner products were calculated. The mean and standard deviation to the inner products of the image for gene A were then compared with the true image of every other gene, obtaining a Z score for each gene. All genes with Z scores greater than 3 were deemed correlated, while those with Z scores less than 3 were deemed anticorrelated. Due to the high false discovery rate, the algorithm was typically run with several test genes (equivalent to gene A), and across several pucks. Genes were then considered only if they were correlated by the z=3 threshold with at least (for example) 2 genes on at least (for example) 2 pucks.

Cerebellar Pattern Analysis:

To identify an initial set of spatially variable genes, the significant gene calling algorithm was run on four sagittal cerebellar pucks, and only those genes that had significantly non-random spatial distribution on at least 3 pucks were kept. Aldoc, Cck, Nefh, Plcb4, Rgs8, and Rgs7 bp were thus identified.

Overlap analysis was then run on those 6 genes. For each of the six genes, only those genes that correlated on at least 3 or more pucks were kept. In this way, Prkcd, Car7, Kctd12, Kitl, Rabgap1, Sema7a, Stk17b, Sv2c, Ldhb, Nedd8, Cox5a, Creg1, Icmt, and 1190002N15Rik, Ilk, and Prkg1 were identified.

In addition, the Significant Gene Calling algorithm was run on three coronal cerebellar pucks, identifying Gnai1, Mapt, Ppm1l, Stmn4, H2-D1, Itgb1bp1, Cyth3, Pcdh17, Olfm1.

Overlap analysis was then run for all 31 of these genes on all 31 pucks. For each gene, the list of genes that correlated with that gene on at least 2 of the seven pucks was taken. Taking the intersection of these lists for all pairs of genes generated FIG. 3E.

For each of the 31 genes, all genes with at least 0.3 correlation with that gene in the Purkinje cells of the atlas dataset were then identified. The resulting 31 sets of genes were then used as metagenes.

Figure 9:
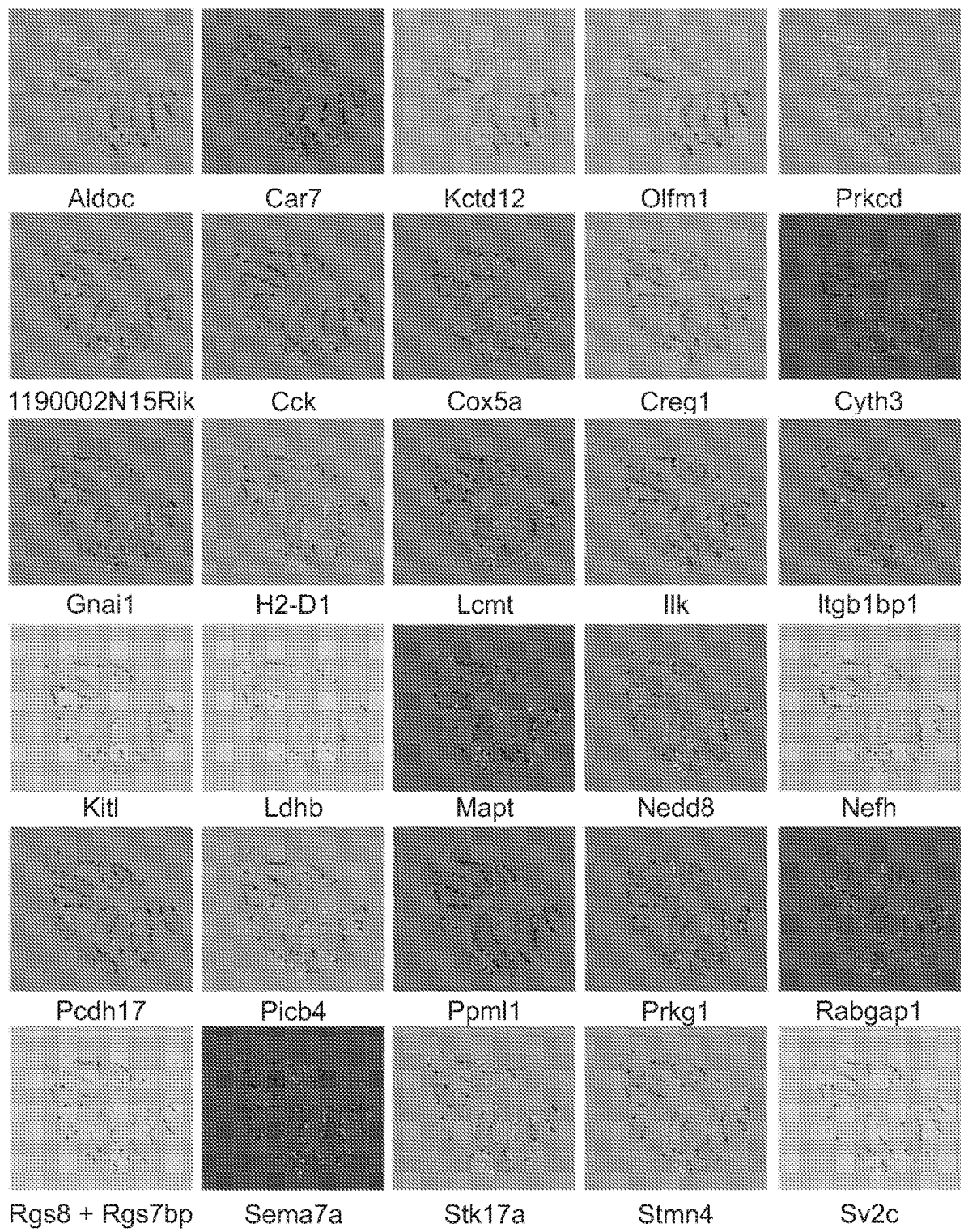
FIG. 9 displays images for all 31 metagenes for genes identified by Slide-seq as spatially varying in the cerebellum. White values indicate more normalized counts in that region than the Pcp4 image obtained, while black values indicate fewer counts. The top row consists of genes found to correlate with Aldoc, while the other rows consist of genes in the Cck cluster. The Rgs8 and Rgs7bp metagenes have been plotted together, because they were highly correlated with each other and only lowly correlated with other genes in the Dropseq dataset.
Figure 10A:
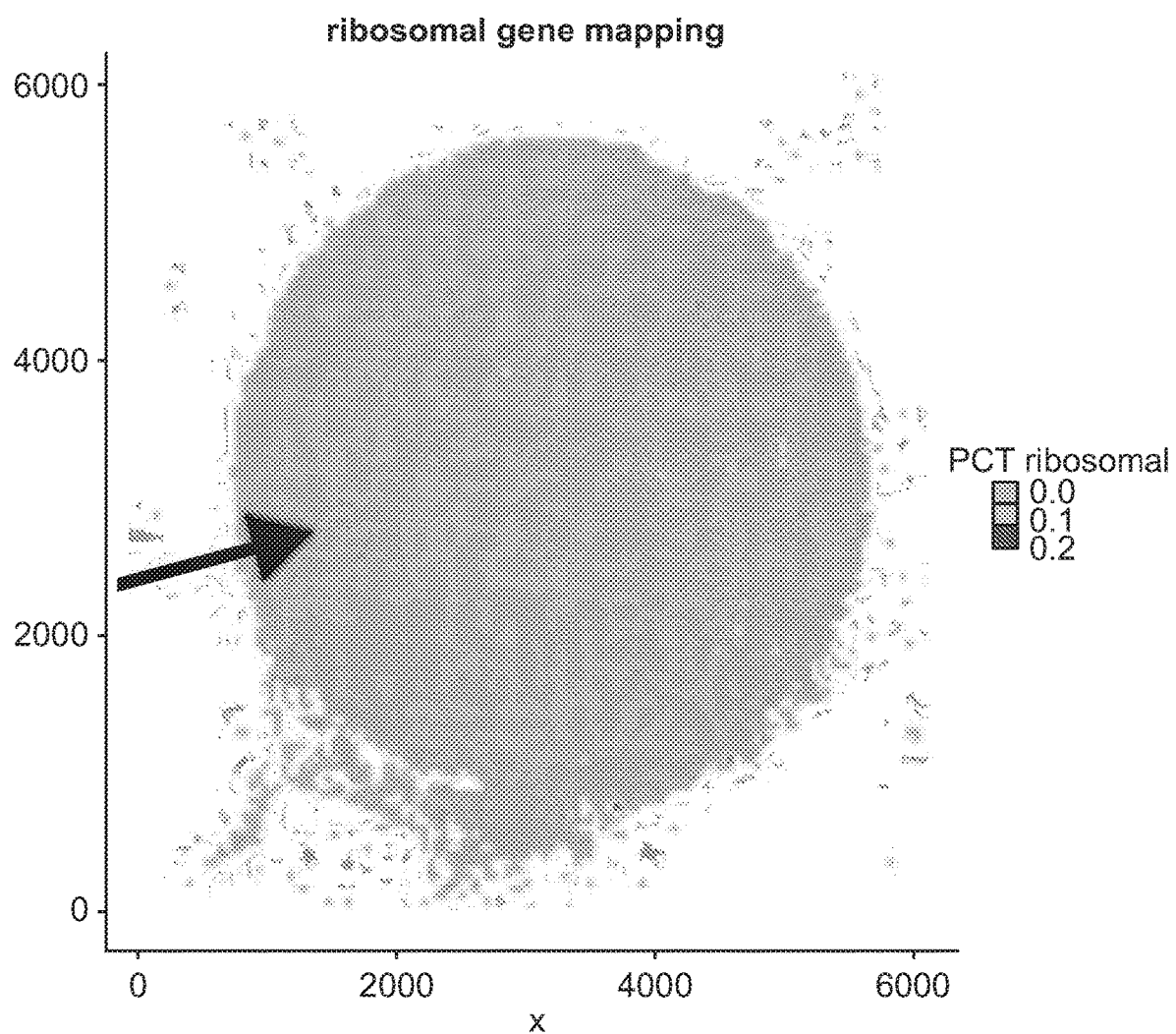
Figure 10B:
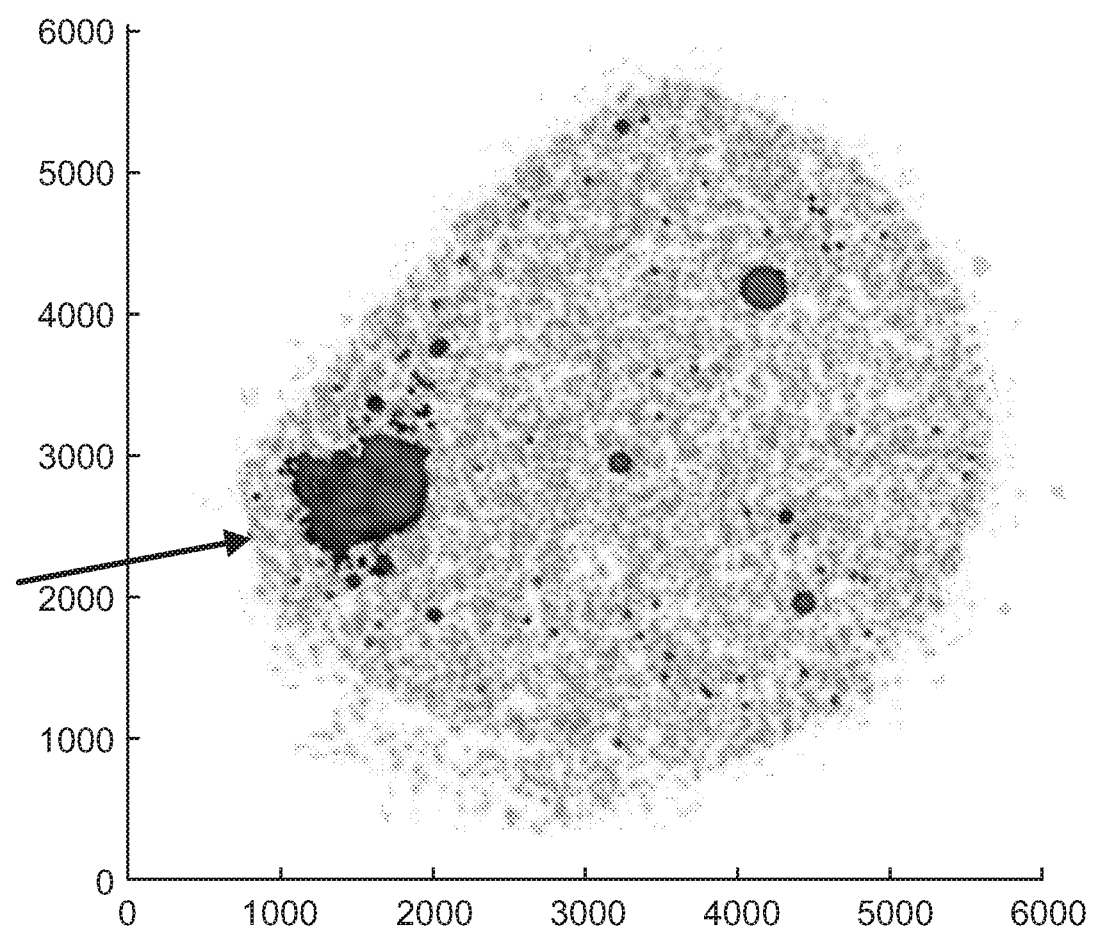
FIG. 10B displays a plot showing beads expressing hemoglobins. All beads expressing at least one transcript of Hba-a1, Hba-a2, Hbb-bs, or Hbb-bt have been shown in dark gray, with radius proportional to the total number of hemoglobin transcripts. All other genes have been shown in light gray.
Figure 10C:
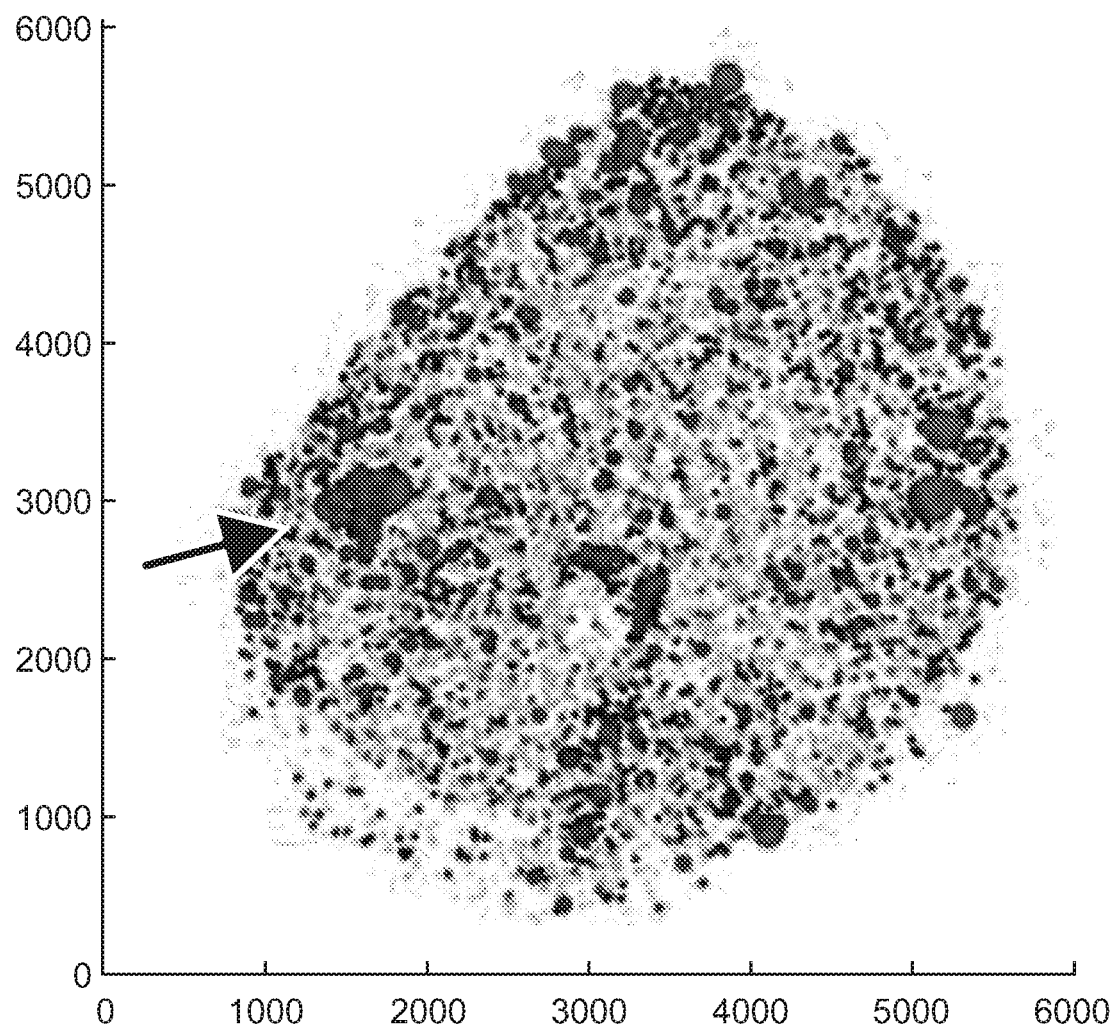
FIG. 10C shows a plot as in FIG. 10B, but for Lars2 transcripts.
Figure 10D:
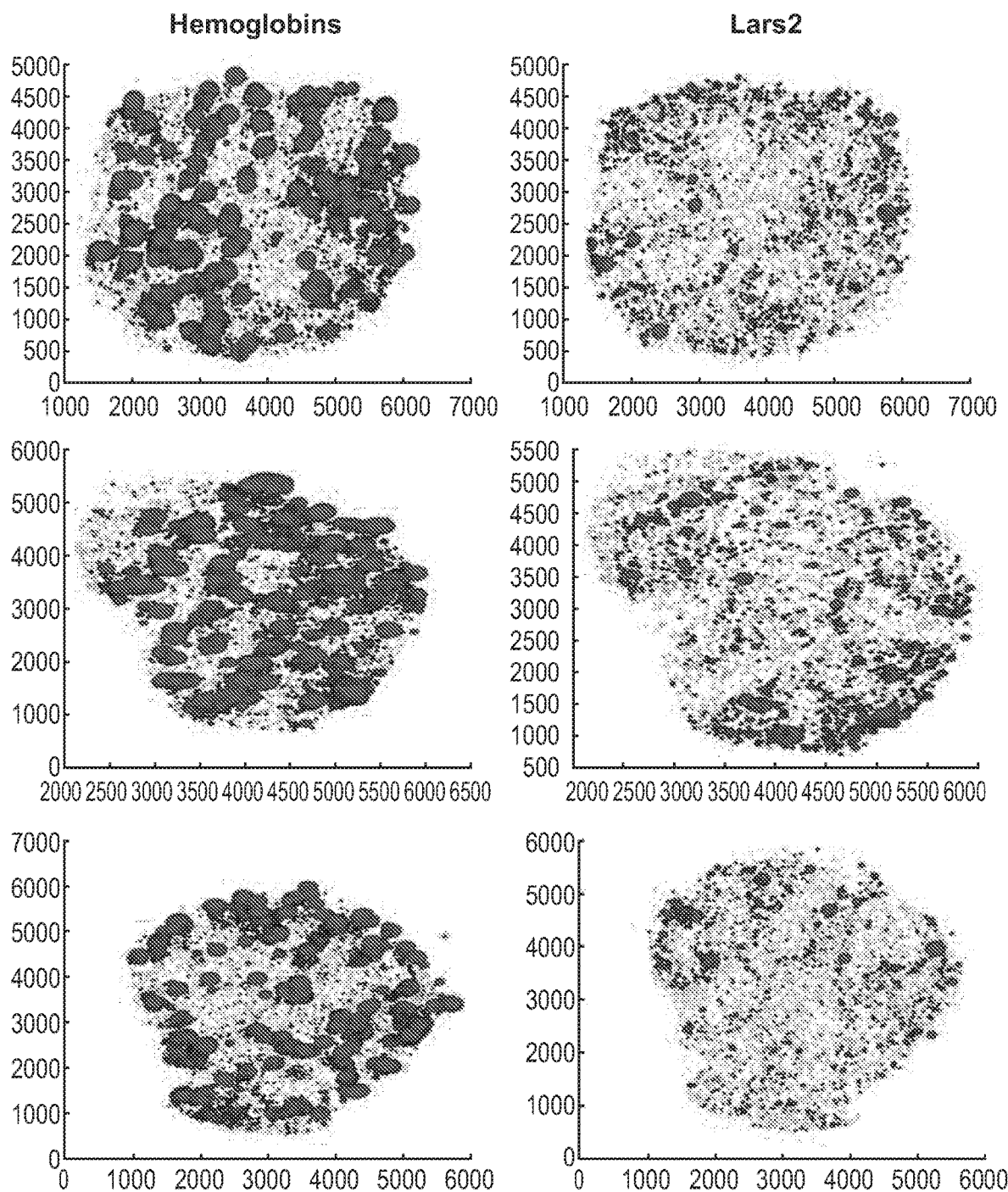

To generate the plots of FIG. 9, an image was first produced in which each bead is represented by a square of side length 70 pixels with intensity equal to the total number of counts of genes in the metagenes. (Overlapping squares summed their intensities in the region of the overlap.) For purposes of display, a similar image was then calculated for the metagene consisting of Pcp2 and Pcp4, which are uniformly expressed in the Purkinje layer. The plots in FIG. 9 are the pointwise difference between plots for each metagene, normalized so the maximum value in each plot is equal to 1, and the plot for the Pcp2/4 metagene, normalized in the same way.

Figure 3A:
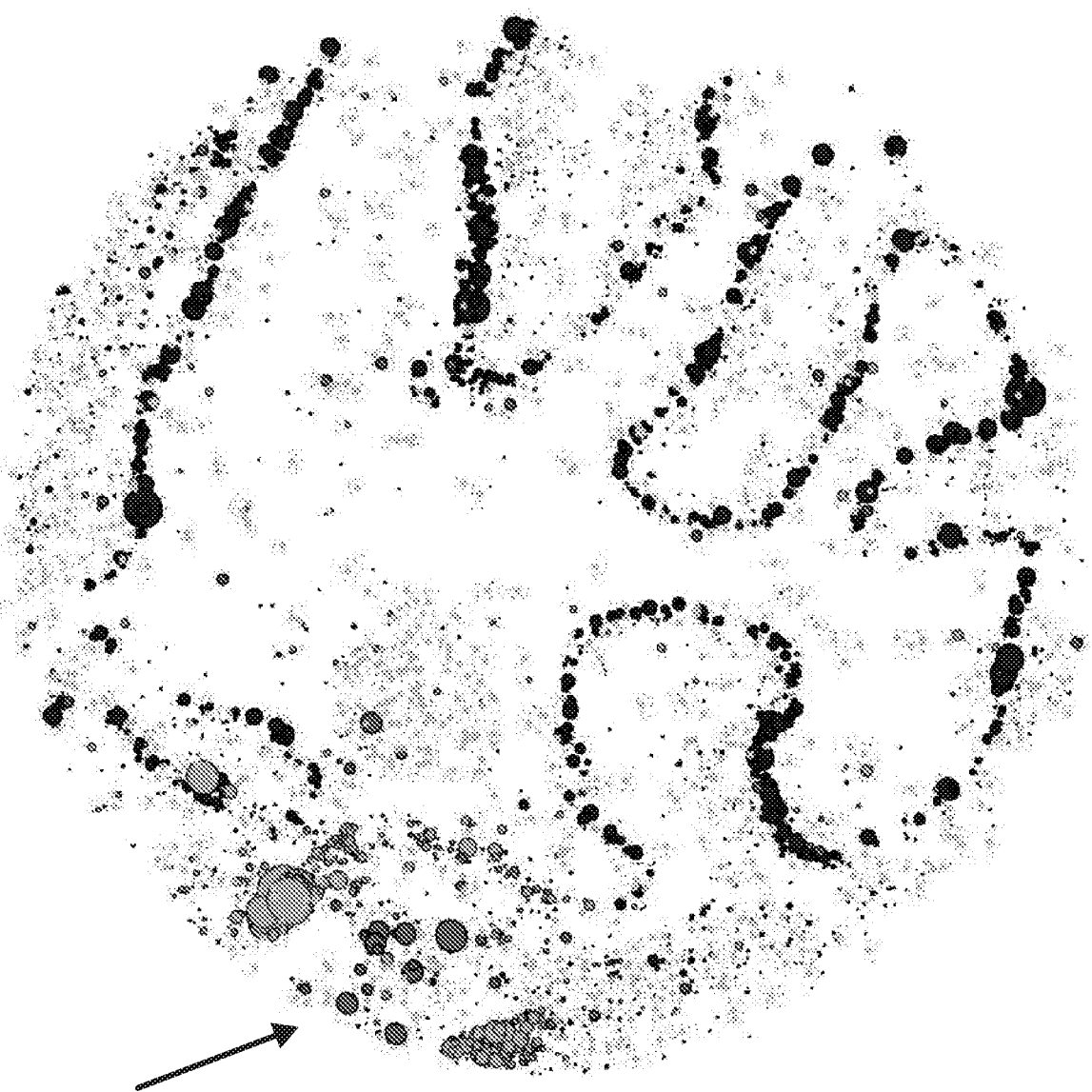
FIGS. 3A to 3L show that Slide-seq identified patterns of spatial gene expression.
Figure 3B:
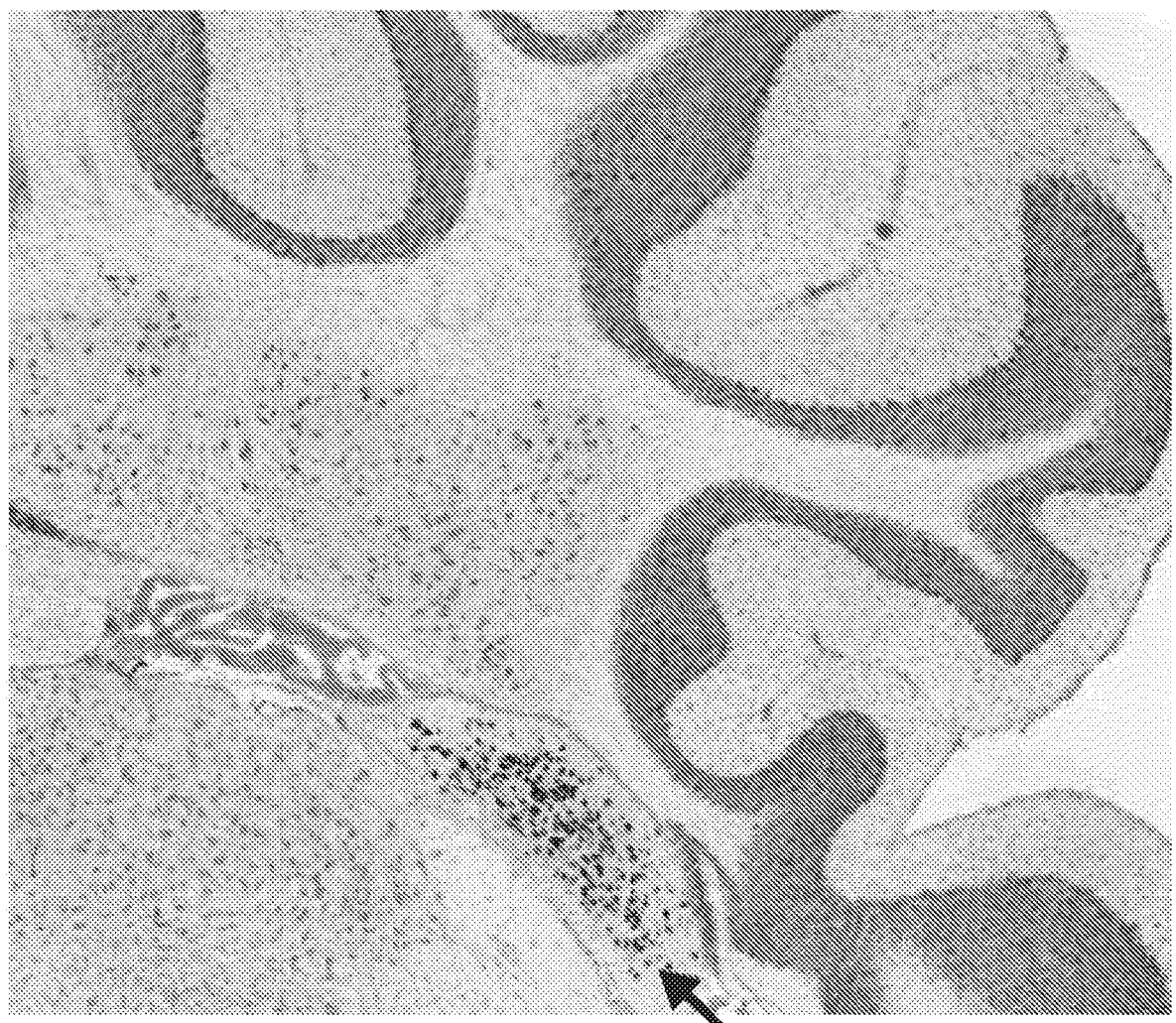
Figure 3C:
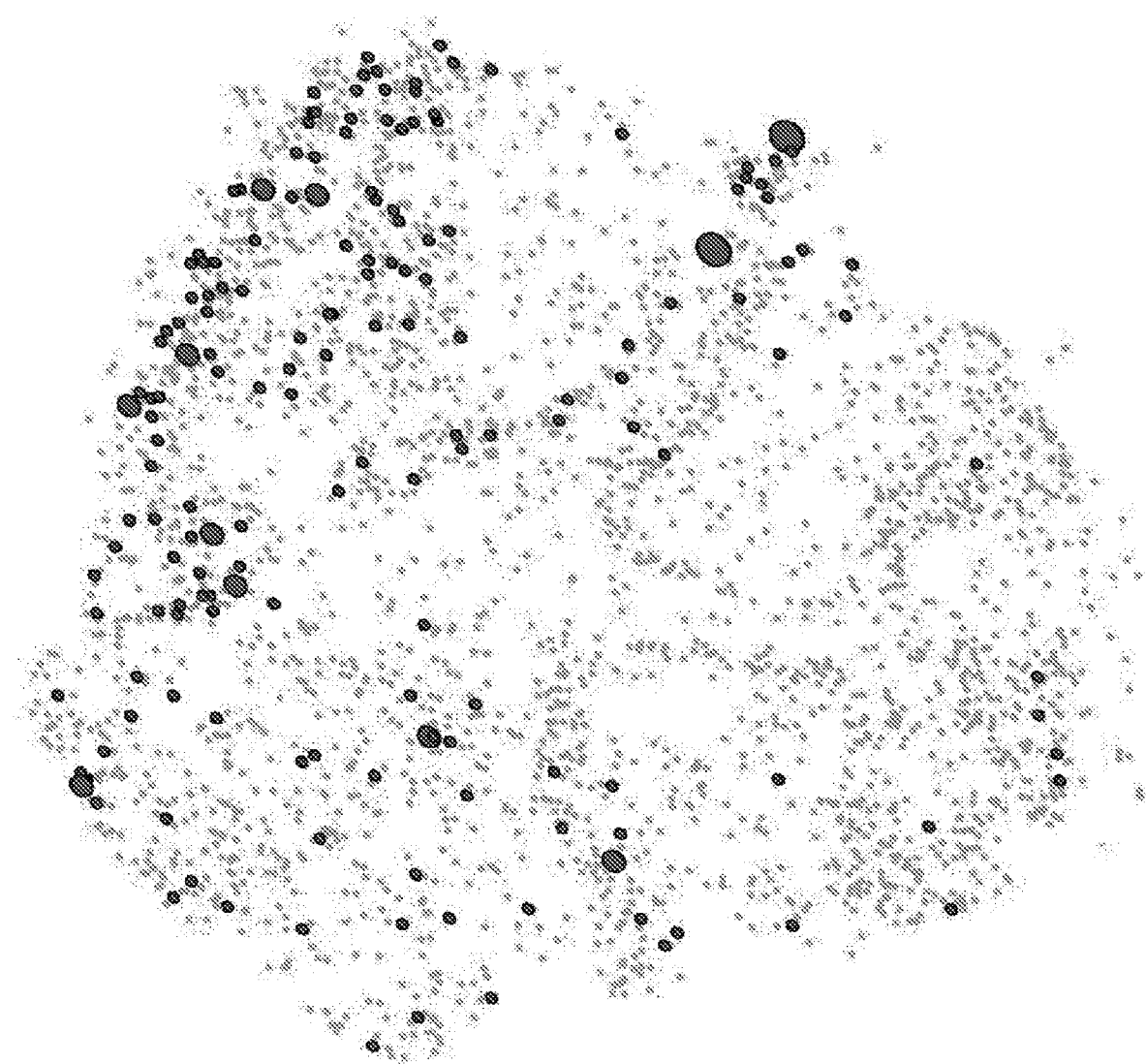
Figure 3D:
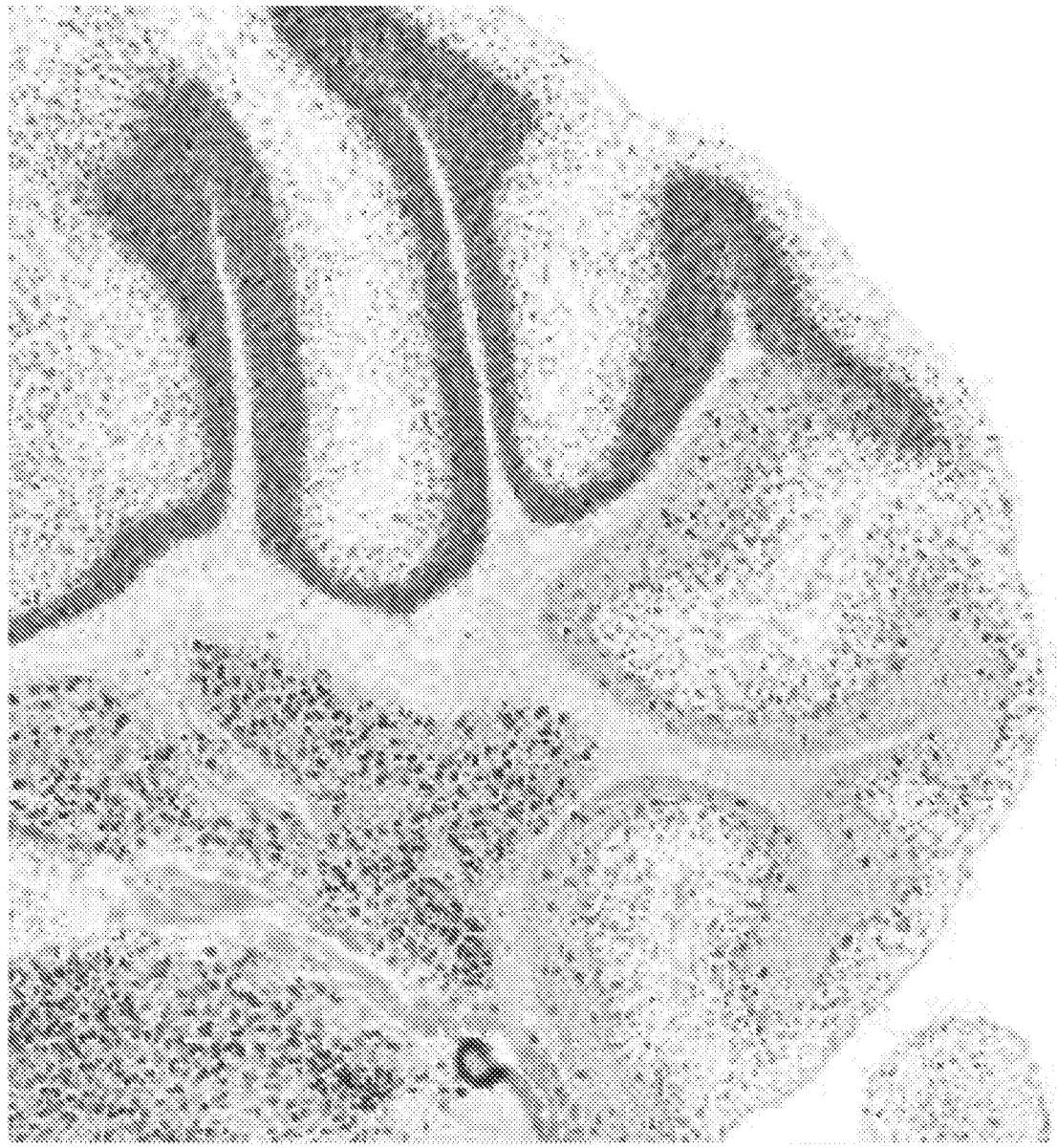
Figure 3E:
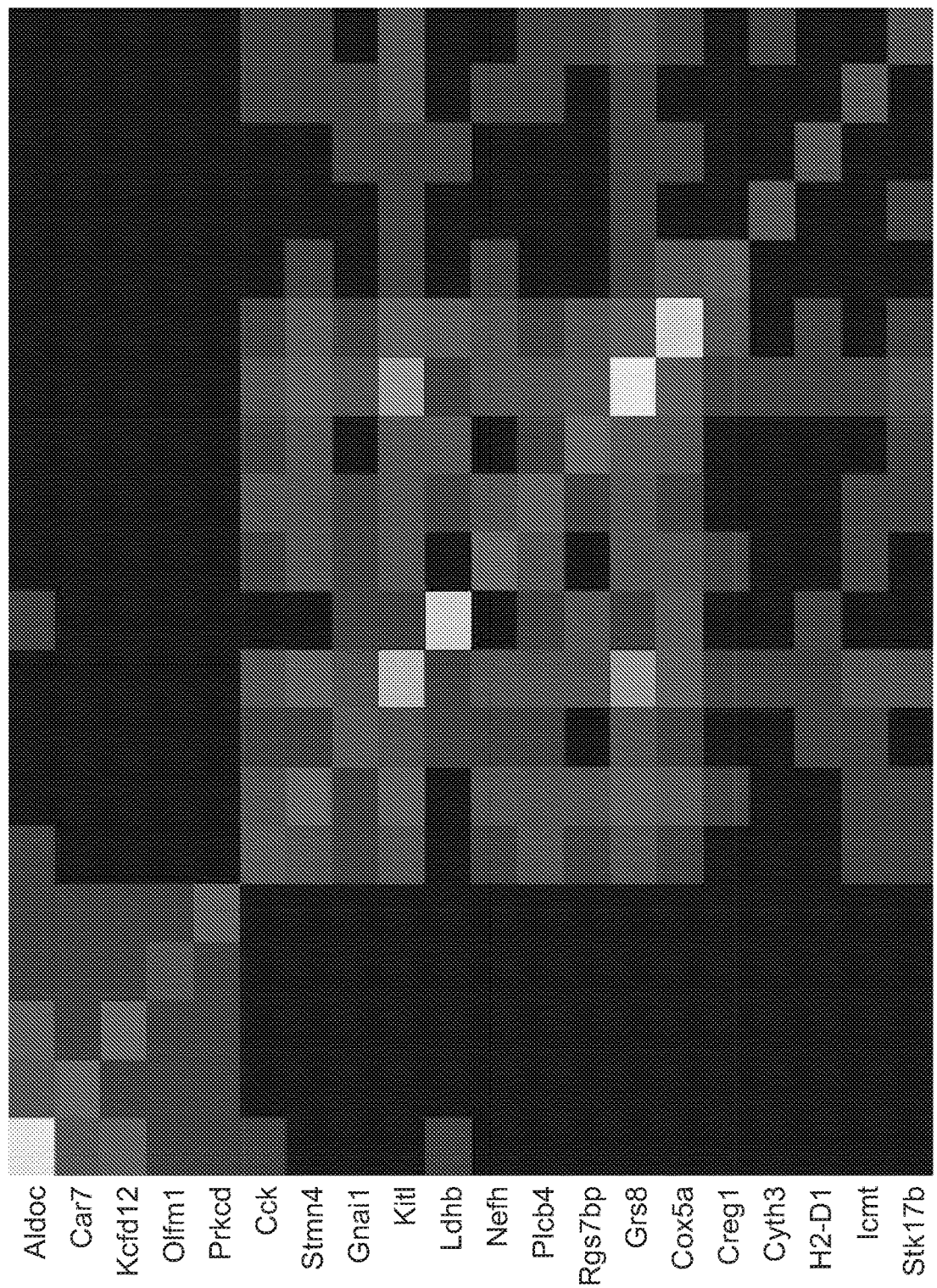
Figure 3F:
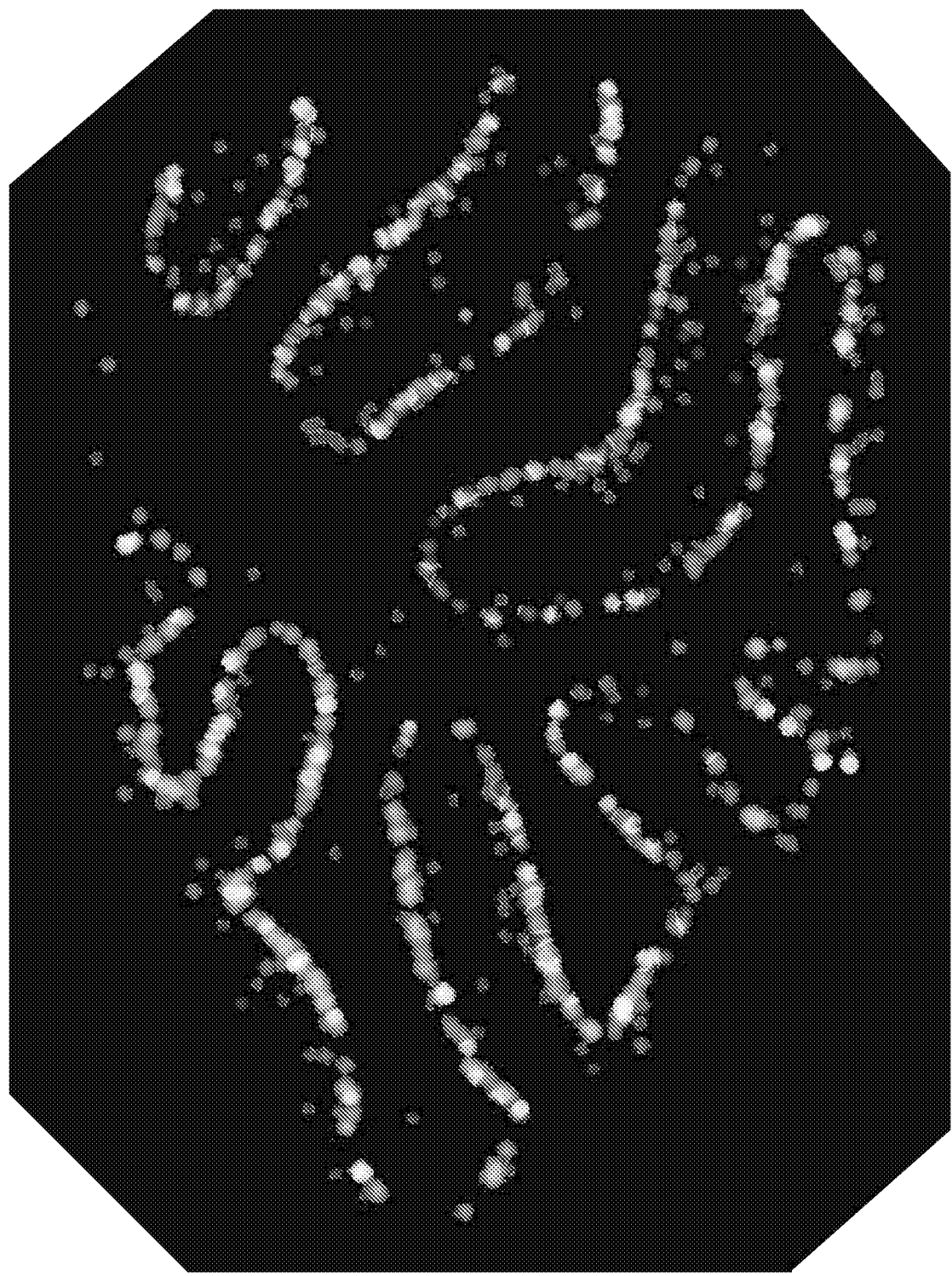
Figure 3G:
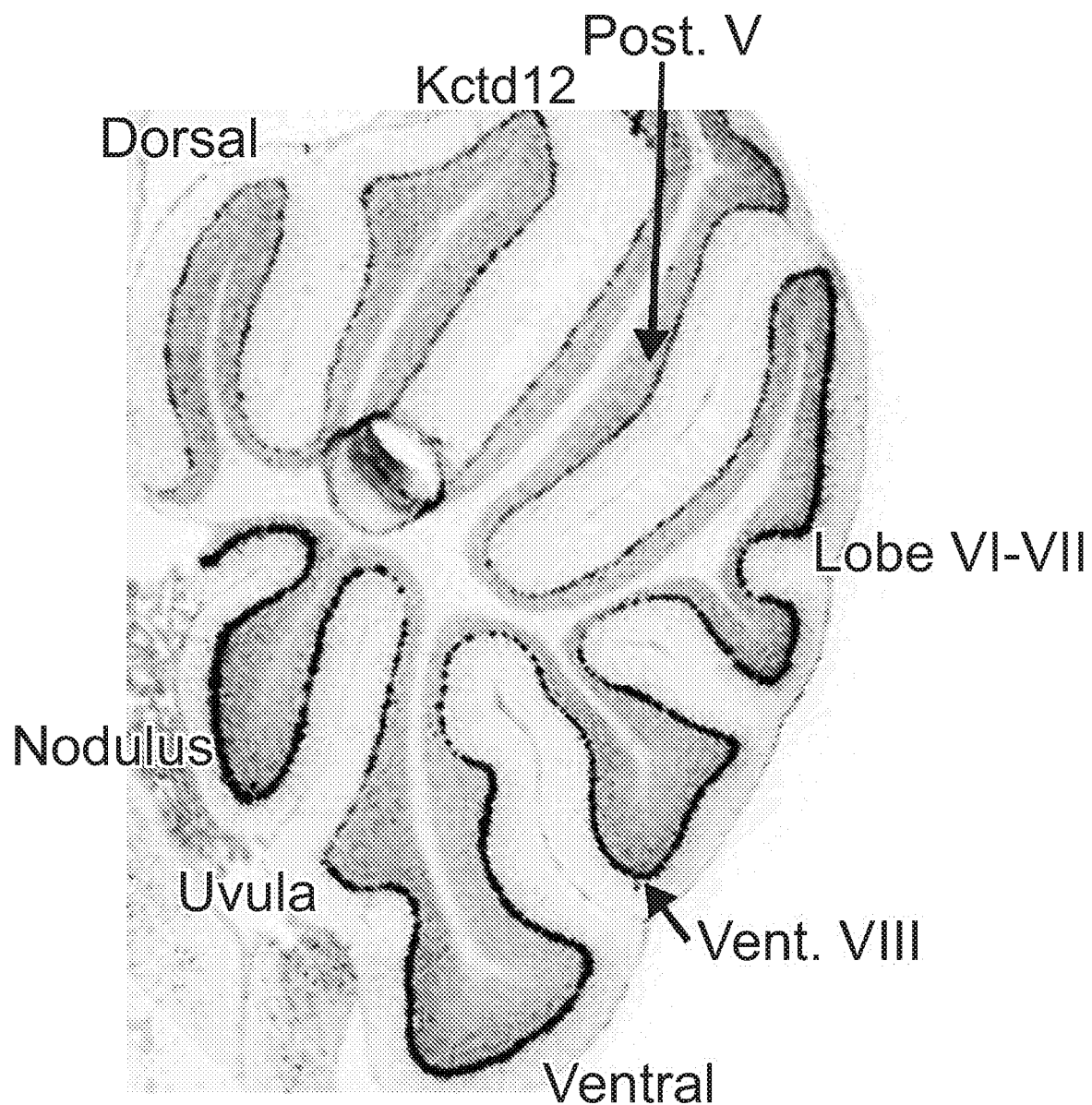
Figure 3H:
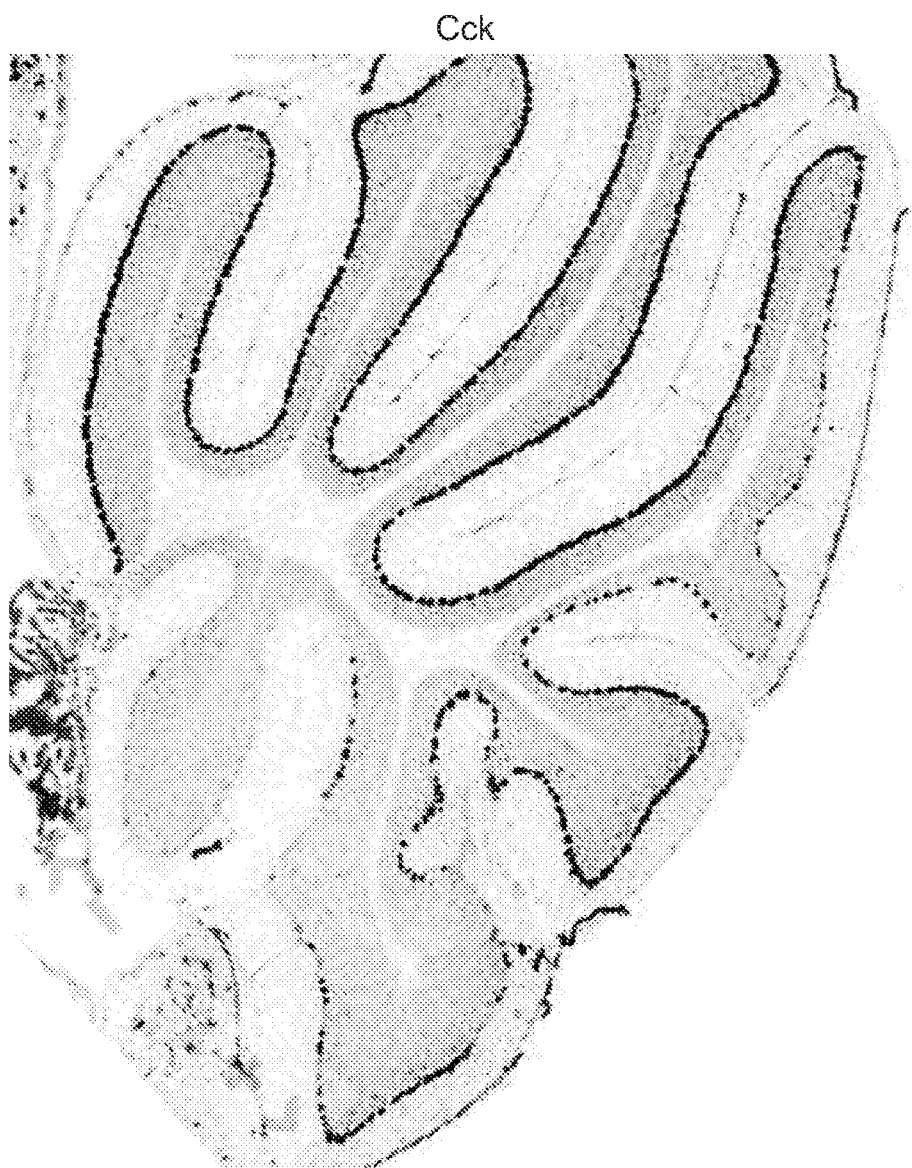
Figure 3I:
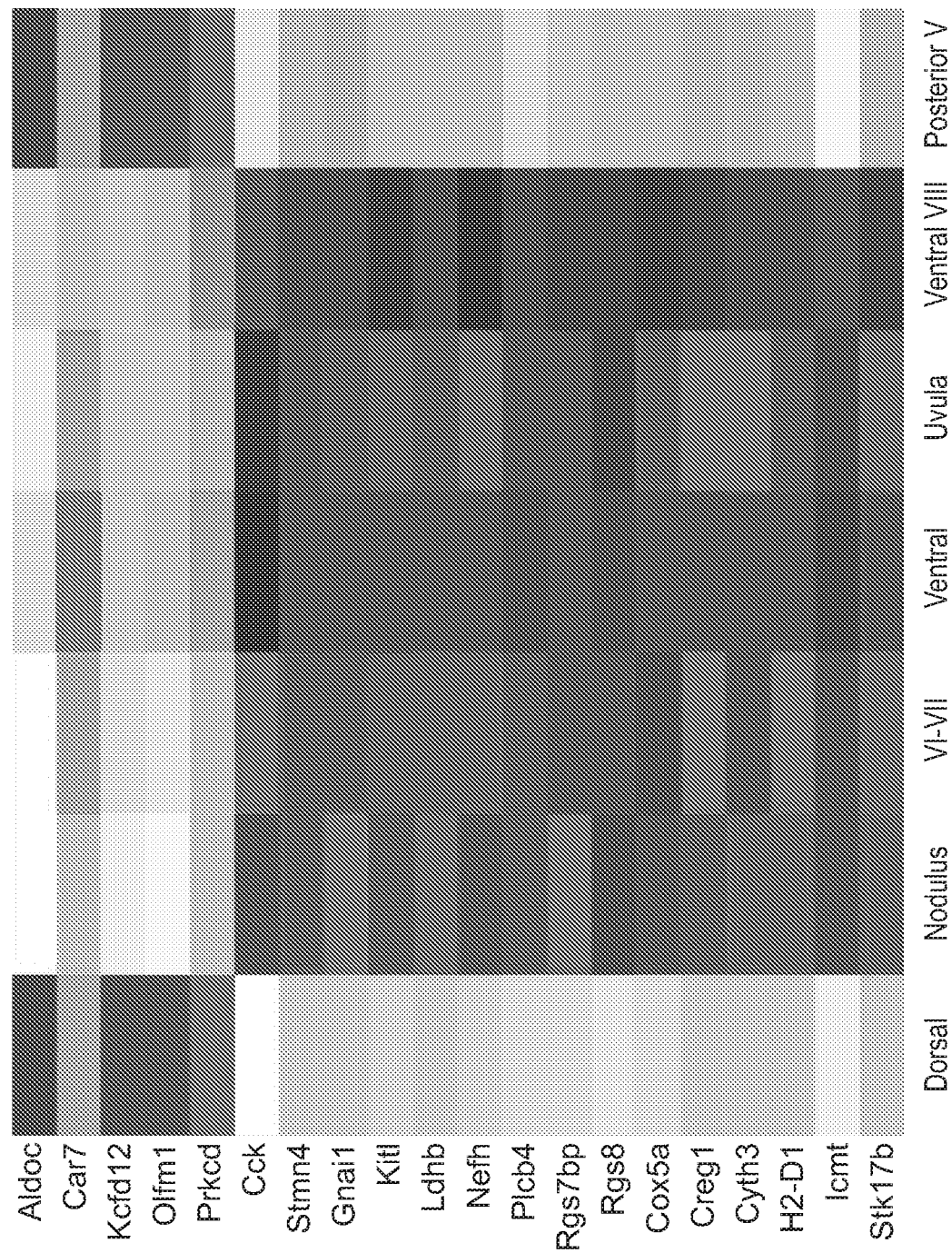
Figure 3J:
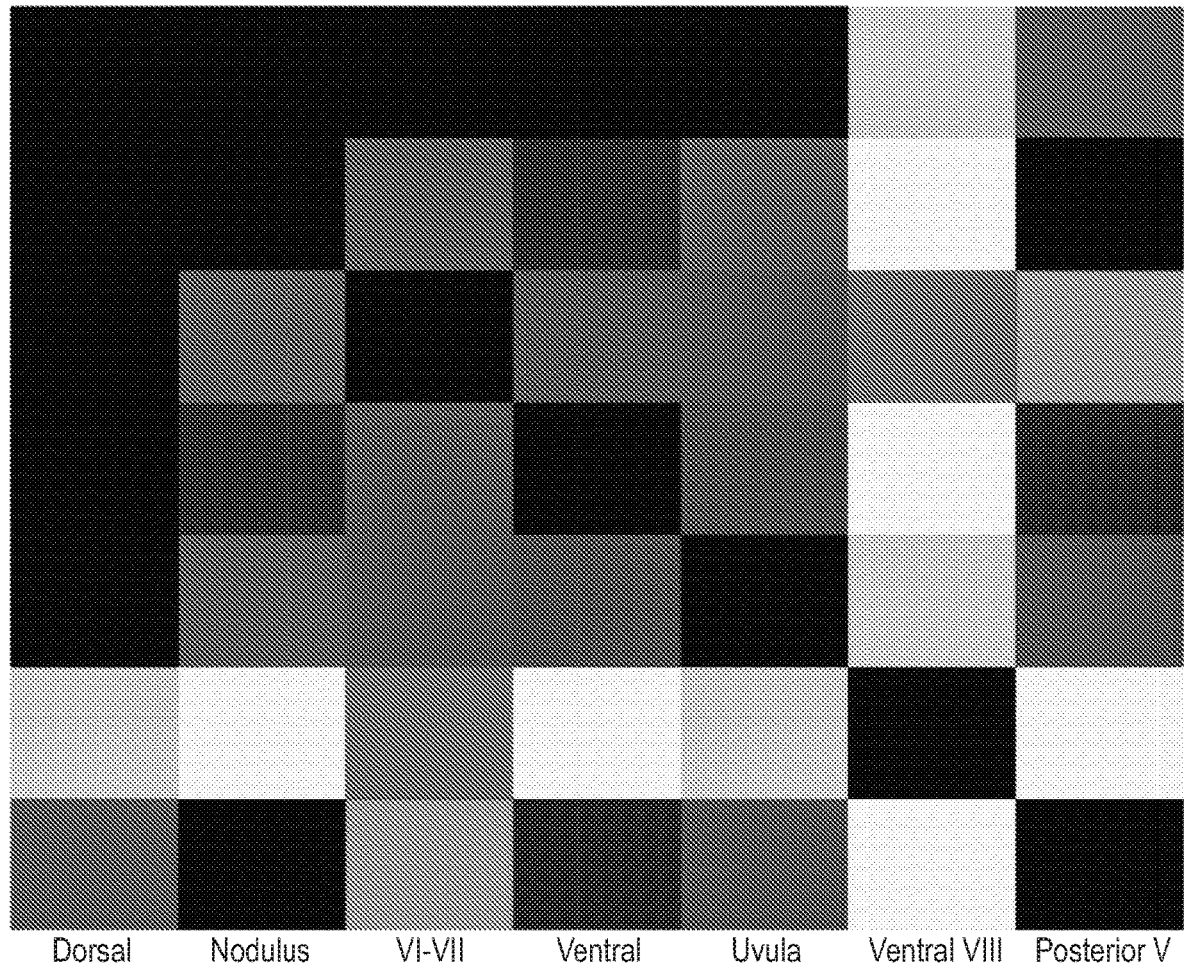

For FIG. 3I, the total intensity of the plots in FIG. 9 was summed (but without first subtracting the Pcp2/4 metagene) within the specified features on Puck 180819_12 (features shown on FIG. 8), which was chosen for analysis because it has the best representation of the anatomical features of interest. (For example, it was the only sagittal cerebellar puck with representation both of the boundary between layers VI and VII and of lobule X.) FIG. 3J shows the correlation between the columns of FIG. 3I.

Figure 4A:
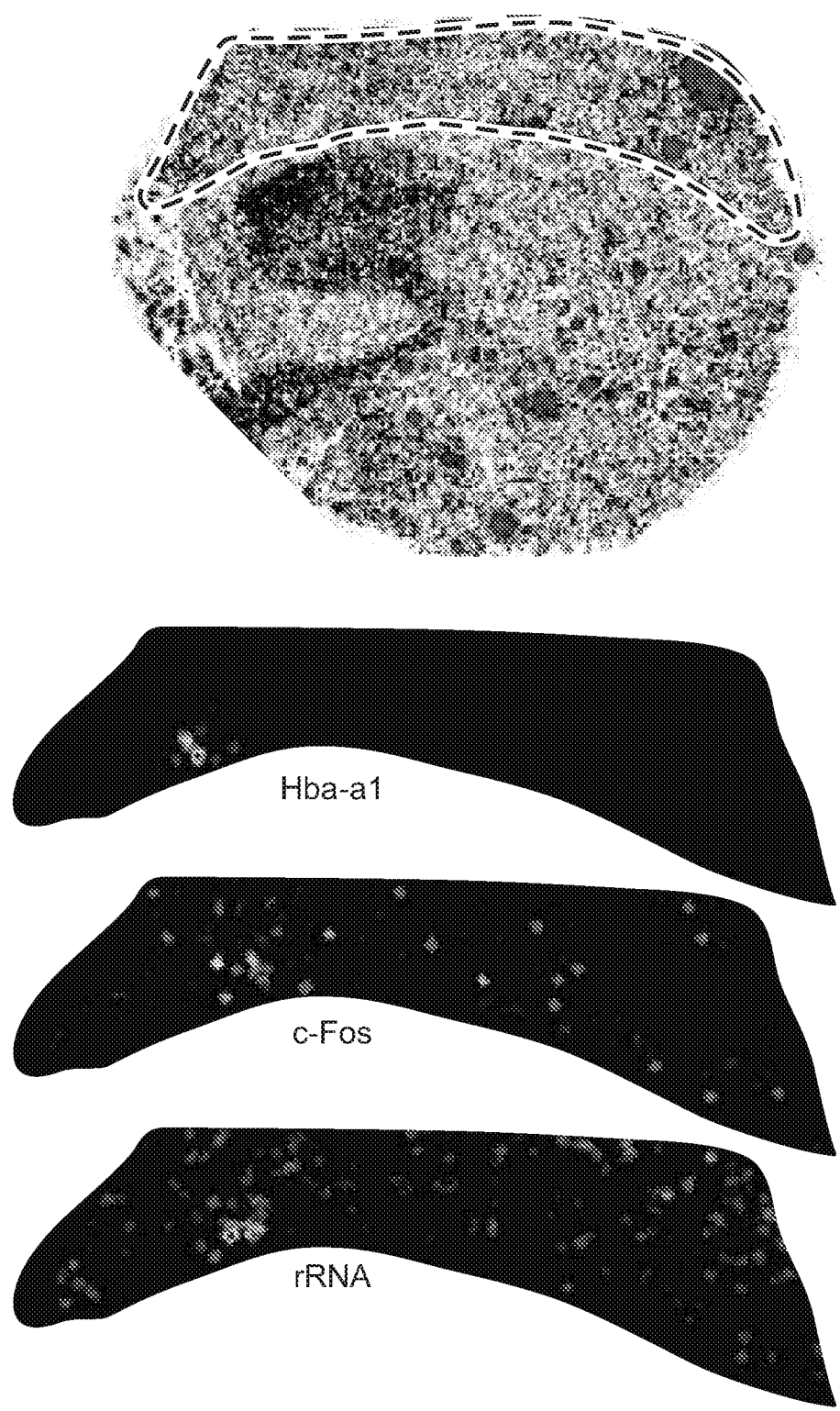
FIGS. 4A to 4K show that Slide-seq identified local transcriptional responses to injury.
Figure 4B:
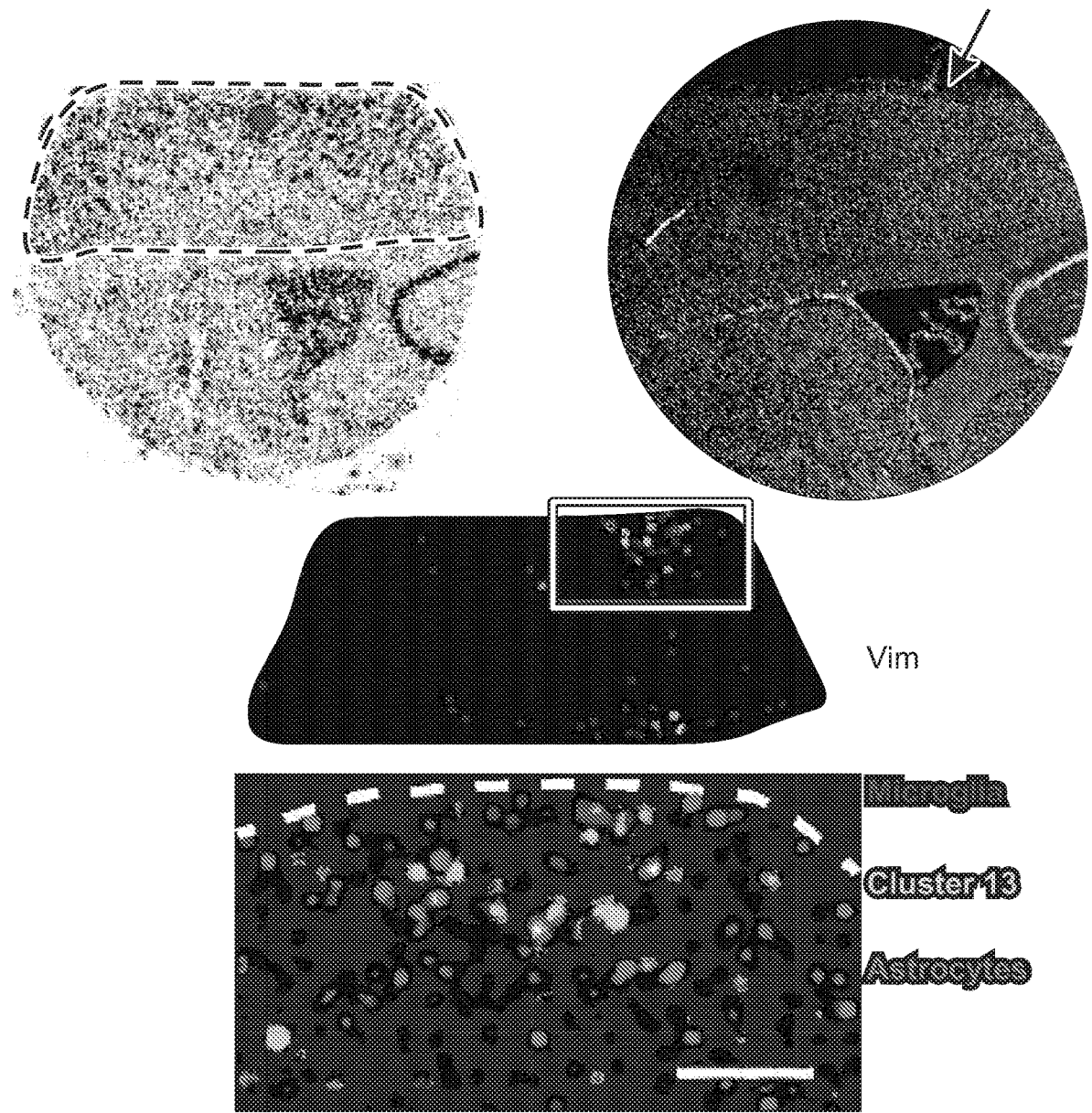
Figure 4C:
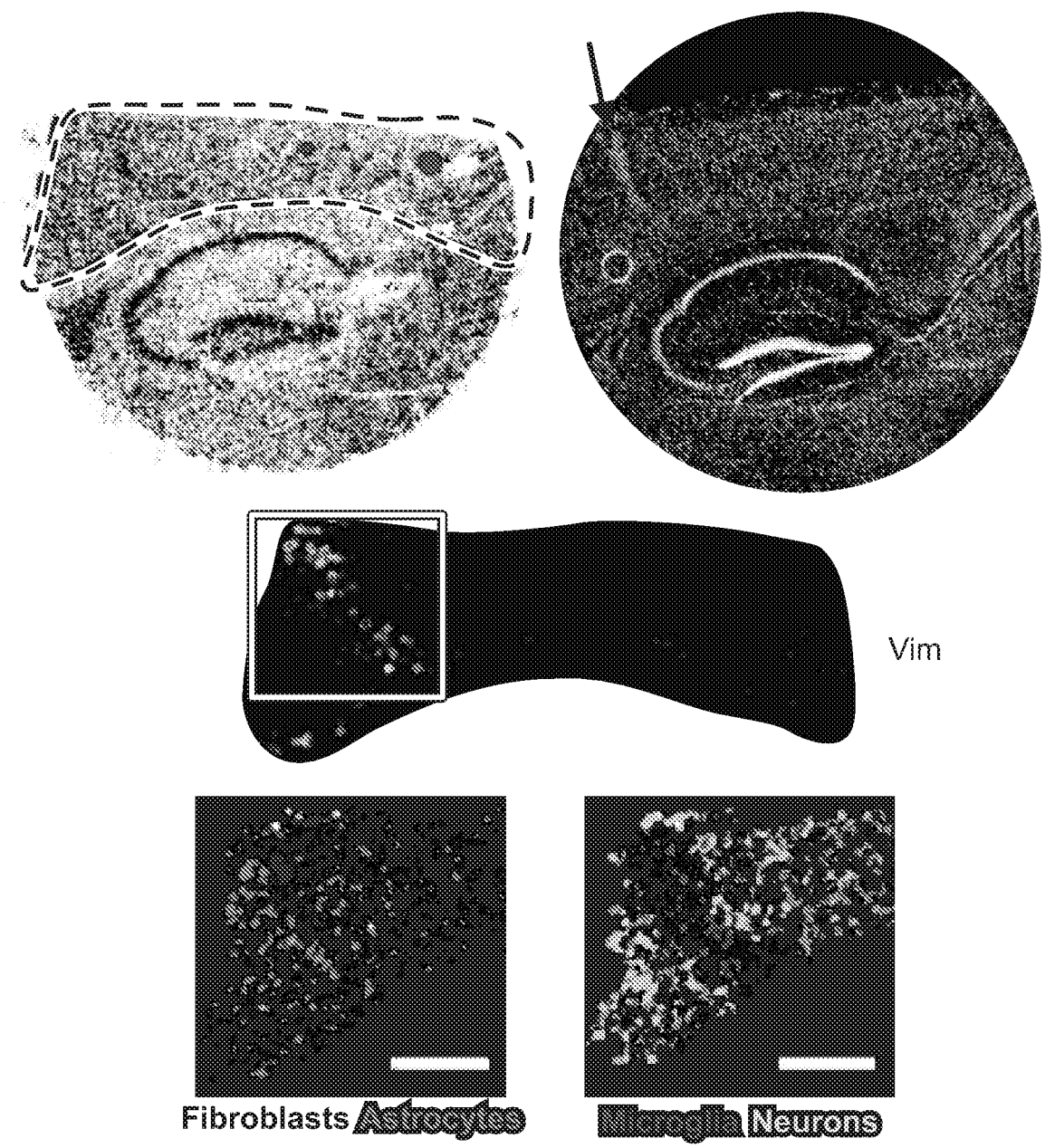
Figure 4D:
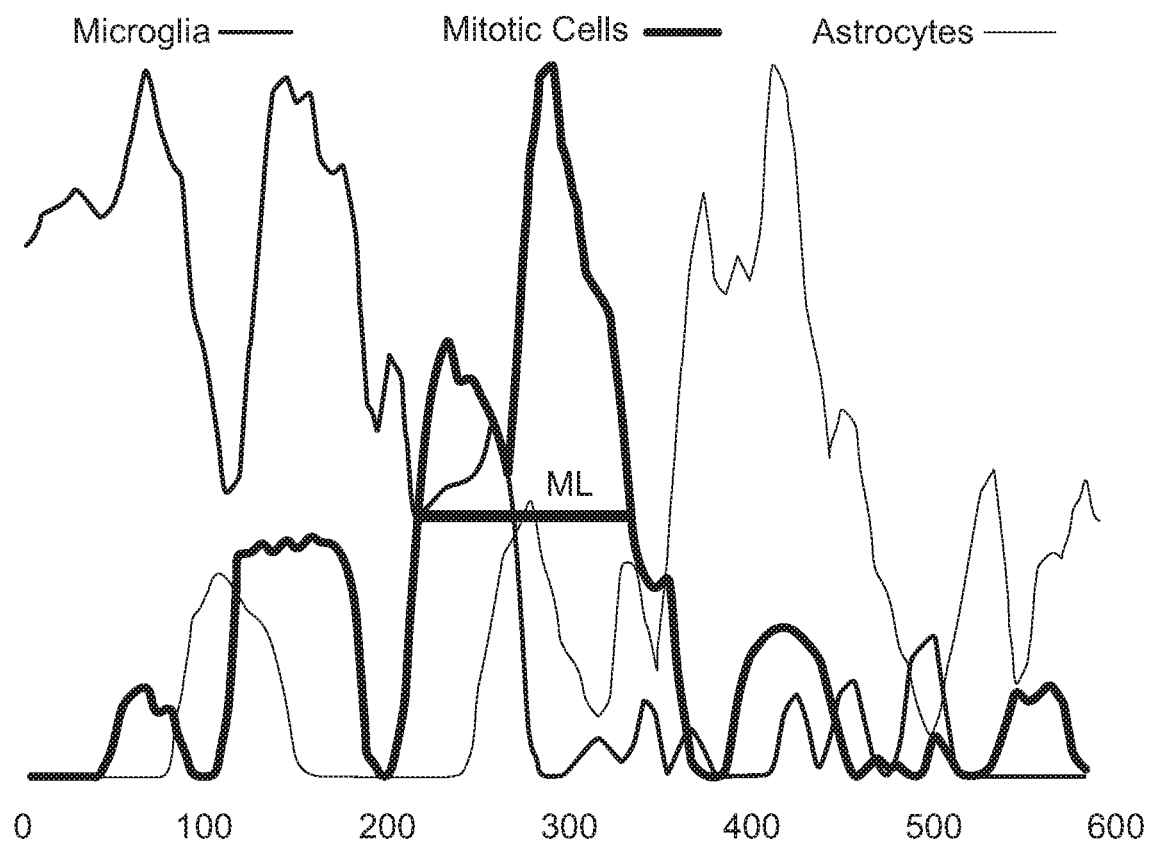
Figure 4E:
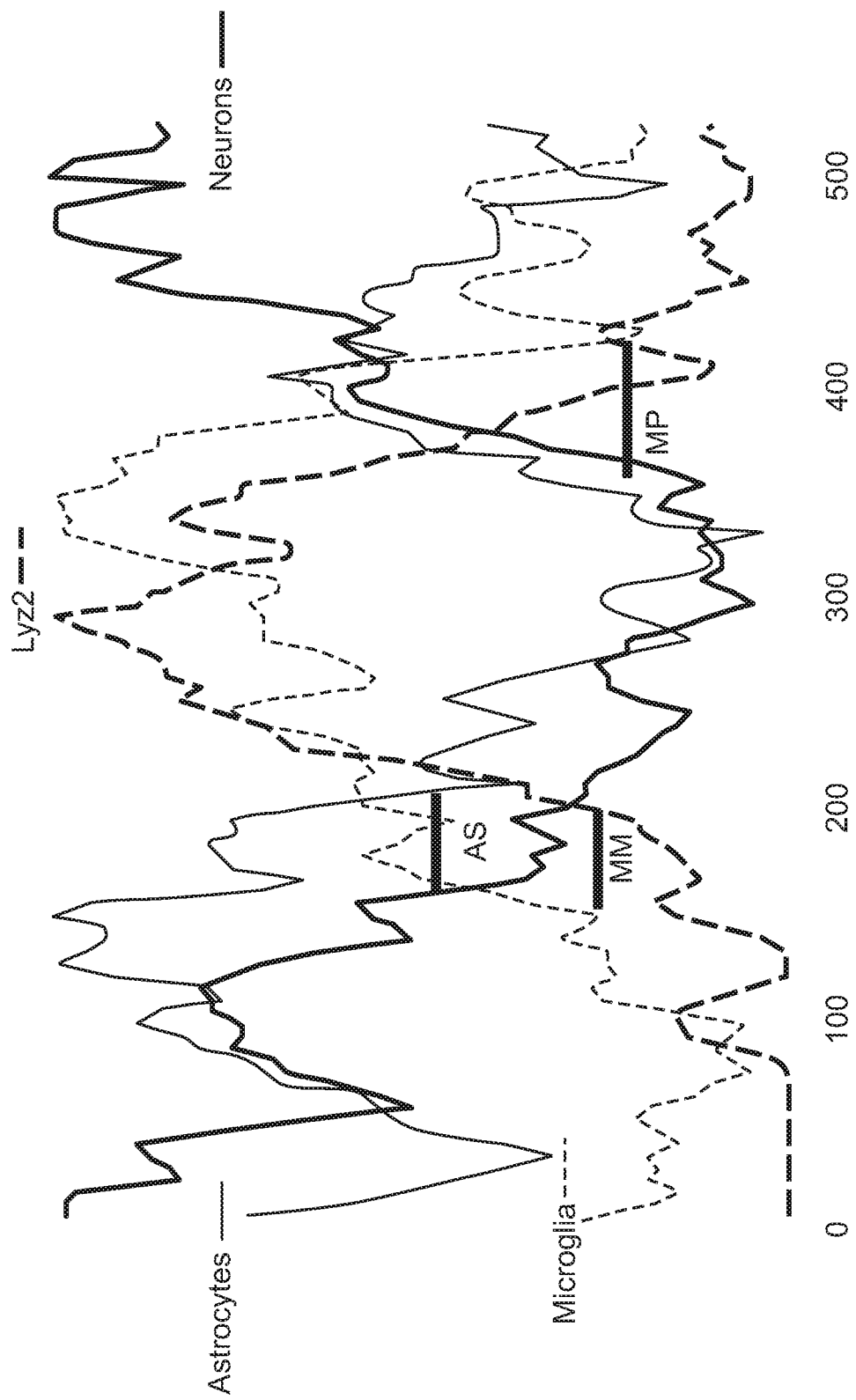

Distance Measurements for Injection Brains:

The distance measurements in FIGS. 4D and 4E were performed by plotting beads in each of cluster of interest with radius proportional to the number of transcripts per bead, with one transcript corresponding to a 25 pixel diameter and 500 corresponding to a 125 pixel diameter. This was done to ensure that beads with more transcripts were weighted more heavily when calculating the spatial profile of the cell types. Boxes were then drawn around the injection site and linecuts were taken (i.e., summed along one axis), to generate the profiles in FIGS. 4D and 4E.

For measurements of the mitosis layer thickness, two measurements from one puck (Puck_180821_3, both sides of the injection site) and one measurement from a second puck (Puck_180819_19, the bottom side of the injection site) were taken. For measurements of the astrocyte scar thickness and the microglial penetration thickness, six measurements were taken: two on each side of the scar from each of three pucks (Puck_180819_5, Puck_180819_6, and Puck_180819_7).

Figure 4F:
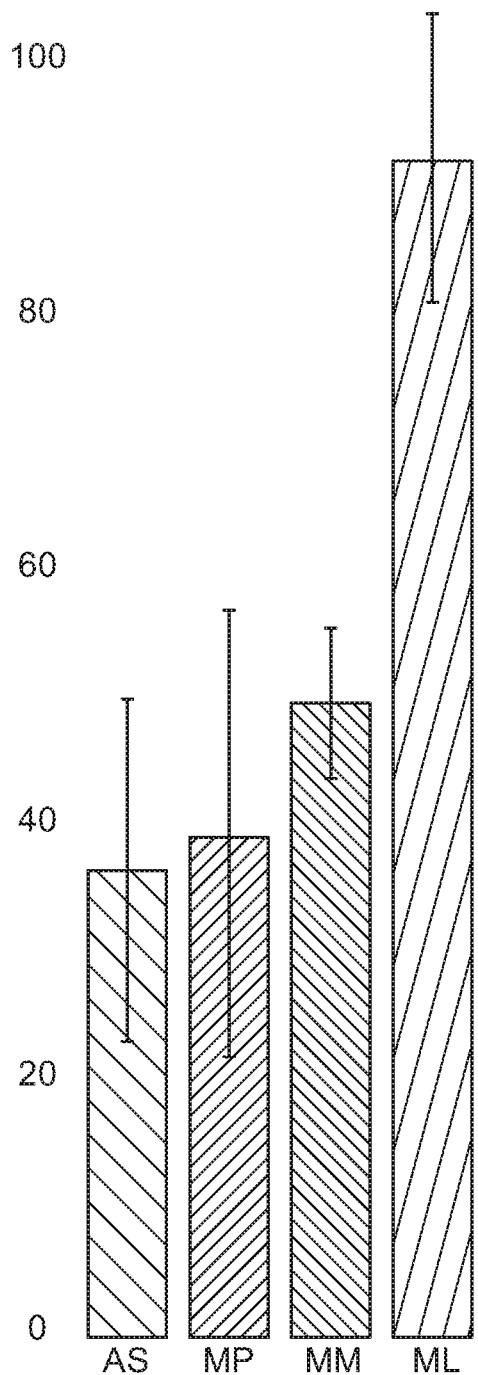
Figure 4G:
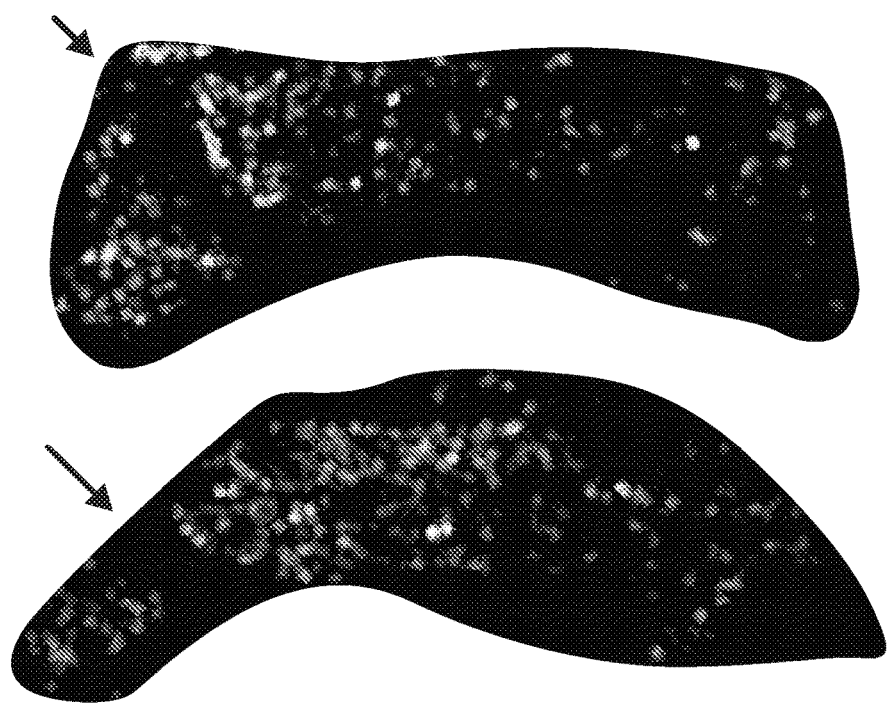

For the distance measurements in FIG. 4G, grayscale versions of the images in FIG. 4G were plotted, and linecuts similar to those taken for the measurements in FIGS. 4D and 4E were taken. Measurements from each side of the injection for puck 180819_7 were taken (FIG. 4G, bottom). Measurements from one side of the injection were additionally taken on pucks 180819_5 and 180819_6. Only one side was used from those pucks, on the grounds that the injection site was very close to the edge of the puck on one side.

Two of the three-day injection pucks, puck 180819_16 and 180819_18, were excluded from all distance measurements on the grounds that the tissue damage did not appear on the puck.

One two-week injection puck, puck 180819_8, was excluded from all distance measurements on the grounds that the tissue slice was more lateral than the other tissue slices. It showed neither enrichment of the immediate early genes around the injection site, nor a dip in astrocyte density in the middle of the scar, indicating that it was likely at the edge of the wound.

Identification of rRNA in Pucks:

During analysis of the 2-hour injection pucks, many counts were observed of the Lars2 gene correlating with hemoglobins and cFos at the injection site. Upon investigation of the Lars2 gene, we found using RepeatMasker (www.repeatmasker.org) that it has a rRNA-derived repeat in its 3' UTR, leading us to hypothesize that the counts we observed of Lars2 might in fact be misaligned rRNA reads (22). Moreover, we found that the spatial distribution of Lars2 counts across the puck is highly correlated to the counts of rRNA, supporting this hypothesis. We thus used Lars2 as a proxy for rRNA expression in FIG. 4A.

Density Plots:

For the density plot images in FIGS. 2B (black backgrounds), 3F, 4B and 4C, an image was as follows. Each point P in the 6030×6030 images was assigned an intensity equal to the sum of the intensities of all beads with centroids lying within 44-pixel square centered on P. For FIG. 2B (black backgrounds) and FIGS. 4B and 4C, each bead assigned to the indicated NMFreg cluster was assigned a unit intensity, while the intensity for each bead in FIG. 3F was taken as the total number of transcripts belonging to genes in the indicated metagene. Finally, the images were passed through Gaussian filters with a standard deviation of 12 pixels.

For the images with dark gray backgrounds in FIGS. 4A-4C and 4G-4K, each bead was represented by a square of length 70 pixels on each side, with intensity equal to the total number of transcripts belonging to the set of genes indicated in the legend. Overlapping squares summed their intensities in the overlap region. For FIGS. 4G-4K, all the images within a given panel were normalized to the same values (i.e., the same shades represent the same values in all four images).

Animal Housing:

Animals were group housed with a 12-hour light-dark schedule. All procedures involving animals at MIT were conducted in accordance with the US National Institutes of Health Guide for the Care and Use of Laboratory Animals under protocol number 1115-111-18 and approved by the Massachusetts Institute of Technology Committee on Animal Care. All procedures involving animals at the Broad Institute were conducted in accordance with the US National Institutes of Health Guide for the Care and Use of Laboratory Animals under protocol number 0120-09-16.

Traumatic Brain Injury Model:

Animals for the TBI model were anesthetized and processed according to a standard intracranial injection protocol. Specifically, mice were anesthetized using isofluorane and stereotactically restrained. Subsequently, an incision was made in the scalp and a hole was made in the skull using a dental drill. A Hamilton needle (32 gauge, 7803-04) was lowered to 2 mm below the surface of the skull, and was then promptly retracted. The wound was closed using Vetbond, and the animal was allowed to recover. Mice were treated with Buprenorphine-SR and Meloxicam for analgesia. Mice were sacrificed by cardiac perfusion 2 hours, 3 days, or 2 weeks following the injection.

Transcardial Perfusion:

Animals were anesthetized by administration of isoflurane in a gas chamber flowing 3% isoflurane for 1 minute. Anesthesia was confirmed by checking for a negative tail pinch response. Animals were moved to a dissection tray and anesthesia was prolonged via a nose cone flowing 3% isoflurane for the duration of the procedure. Transcardial perfusions were performed with ice cold pH 7.4 HEPES buffer containing 110 mM NaCl, 10 mM HEPES, 25 mM glucose, 75 mM sucrose, 7.5 mM MgCl2, and 2.5 mM KCl to remove blood from brain and other organs sampled. The appropriate organs were removed and frozen for 3 minutes in liquid nitrogen vapor and moved to −80° C. for long term storage.

Tissue Handling:

Fresh frozen tissue tissue was warmed to −20° C. in a cryostat (Leica CM3050S) for 20 minutes prior to handling. Tissue was then mounted onto a cutting block with OCT and sliced at a 5 degree cutting angle at 10 μm thickness. Both OCT embedded and non-OCT embedded samples have been used for the instant procedure and equal yields have been observed in recovery of transcripts. Pucks were then placed on the cutting stage and tissue was maneuvered onto the pucks. The tissue was then melted onto the puck by moving the puck off the stage and placing a finger on the bottom side of the glass. The puck was then removed from the cryostat and placed into a 1.5 ml eppendorf tube. The sample library was then prepared as below. The remaining tissue was redeposited at −80° C. and stored for processing at a later date.

Library Preparation:

Pucks in 1.5 mL tubes were immersed in 200 μL of hybridization buffer (6×SSC with 2 U/uL Lucigen NxGen RNAse inhibitor) for 15 minutes at room temperature to allow for binding of the RNA to the oligos on the beads. Subsequently, first strand synthesis was performed by incubating the pucks in RT solution for 1 hour at 42° C.

RT Solution:
  75 μl H2O
  40 μl Maxima 5× RT Buffer (Thermofisher, EP0751)
  40 μl 20% Ficoll PM-400 (Sigma, F4375-10G)
  20 μl 10 mM dNTPs (NEB N0477L)
  5 μl RNase Inhibitor (Lucigen 30281)
  10 μl 50 μM Template Switch Oligo (Qiagen #339414YC00076714)
  10 μl Maxima H-RTase (Thermofisher, EP0751)

200 μL of 2× tissue digestion buffer was then added directly to the RT solution and the mixture was incubated at 37 C for 40 minutes.

2× Tissue Digestion Buffer:
  200 mM Tris-Cl pH 8
  400 mM NaCl
  4% SDS
  10 mM EDTA
  32 U/mL Proteinase K (NEB P8107S)

The solution was then pipetted up and down vigorously to remove beads from the surface, and the glass substrate was removed from the tube using forceps and discarded. 200 μl of Wash Buffer was then added to the 400 μl of tissue clearing and RT solution mix and the tube was then centrifuged for 3 minutes at 3000 RCF. The supernatant was then removed, the beads were resuspended in 200 μL of Wash Buffer, and were centrifuged again. After repeating this procedure an additional 2 times, the beads were moved into a 200 μL PCR strip tube, pelleted in a minifuge, and resuspended in 200 μL of water. The beads were then pelleted and resuspended in library PCR mix and PCRed.

Wash Buffer:
  10 mM Tris pH 8.0
  1 mM EDTA
  0.01% Tween-20

Library PCR Mix:
  23 μl H20
  25 μl of 2× Kapa Hifi Hotstart ready mix (Kapa Biosystems KK2601)
  1 μl of 100 μm Truseq PCR handle primer (IDT)
  1 μl of 100 μm SMART PCR primer (IDT)

PCR Program:
  95 C 3 minutes
  4 cycles of:
    98 C 20 s
    65 C 45 s
    72 C 3 min
  9 cycles of:
    98 C 20 s
    67 C 20 s
    72 C 3 min
  Then:
    72 C 5 min
    4 C forever The PCR product was then purified by adding 30 μl of Ampure XP (Beckman Coulter A63880) beads to 50 μl of PCR product. The samples were cleaned according to manufacturer's instructions and resuspended into 10 ul of water. 1 μL of the resulting sample was run on an Agilent Bioanalyzer High sensitivity DNA chip (Agilent 5067-4626) for quantification of the library. Then, 600 pg of PCR product was taken from the PCR product and prepared into Illumina sequencing libraries through tagmentation with Nextera XT kit (Illumina FC-131-1096). Tagmentation was performed according to manufacturer's instructions and the library was amplified with primers Truseq5 and N700 series barcoded index primers. The PCR program was as follows:

72° C. for 3 minutes
95° C. for 30 seconds
12 cycles of:
   95° C. for 10 seconds
   55° C. for 30 seconds
   72° C. for 30 seconds
72° C. for 5 minutes
Hold at 10° C.

Samples were cleaned with AMPURE XP (Beckman Coulter A63880) beads in accordance with manufacturer's instructions at a 0.6× bead/sample ratio (30 μL of beads to 50 μL of sample) and resuspended in 10 μL of water. Library quantification was performed using the Bioanalyzer. Finally, the library concentration was normalized to 4 nM for sequencing. Samples were sequenced on the Illumina NovaSeq S2 flowcell with 12 samples per run (6 samples per lane) with the read structure 42 bases Read 1, 8 bases i7 index read, 50 bases Read 2. Each puck received approximately 200M-400M reads, corresponding to 3,000-5,000 reads per bead.

TABLE 1

Oligonucleotides used in this study. Note: "r" prior to base indicates RNA. "+" indicates LNA (locked nucleic acid)

| Name | Sequence |
|---|---|
| Truseq5 | AATGATACGGCGACCACCGAGATCTACACTCTTTCCCTACAC GACGCTCTTCCGATCT (SEQ ID NO: 3) |
| Smart PCR primer | AAGCAGTGGTATCAACGCAGAGT (SEQ ID NO: 4) |
| Truseq PCR handle | CTACACGACGCTCTTCCGATCT (SEQ ID NO: 5) |
| Template Switch Oligo (TSO) | AAGCTGGTATCAACGCAGAGTGAATrG+GrG (SEQ ID NO: 6) |

Example 2: Stable Association of Individually Barcode-Tagged Microbeads with a Glass Slide Provided a High-Resolution Array for Transcriptome Capture A large number of 10 μm beads that possessed unique nucleic acid barcodes were prepared via methods as described previously (e.g., as set forth in WO 2016/040476). Specifically, to generate a population of beads possessing individual barcodes that could be used for identification of an individual bead's position when arranged in a two-dimensional array as presently exemplified, polynucleotide synthesis was performed upon the surface of the beads in a pool-and-split fashion such that in each cycle of synthesis the beads were split into subsets that were subjected to different chemical reactions; and then this split-pool process was repeated in multiple cycles, to produce a combinatorially large number (approaching $4^n$) of distinct nucleic acid barcodes (FIG. 1A). Nucleotides were chemically built onto the bead material in a high-throughput manner, and the bead population that was used possessed approximately a billion ($10^9$) unique bead-specific barcodes. After on-bead oligonucleotide synthesis, a glass slide was employed as a solid support for generation of an array of barcoded beads. To provide a capture material-coated surface for the bead array, the glass slide was initially coated with liquid electrical tape (applied as a liquid, the liquid tape dried to a vinyl polymer).

Barcoded beads as described above were applied to the capture material-coated slide, generating an array of beads in a dry condition (excess, non-captured beads were removed from the slide, thereby producing a single layer of captured beads). Because individually barcoded beads were deposited upon the capture material-coated surface in no pre-defined order, in situ sequencing of the bead array while captured upon the slide was performed, using the previously described SOLiD™ method (a sequencing-by-ligation technique that can be performed in situ upon a solid support— refer, e.g., to Voelkerding et al, Clinical Chem., 55-641-658, 2009; U.S. Pat. Nos. 5,912,148; 6,130,073, which are incorporated herein by reference in their entireties), thereby associating a bead's spatial barcode sequence with the two-dimensional location of that bead within the two-dimensional, slide-captured bead array (FIG. 1A).

The oligonucleotide-coated microbeads were thus attached to a glass slide surface as a two-dimensional solid support, and bead-attached oligonucleotide sequences were obtained within the spatial barcode sequence region for purpose of registering the respective locations of microbeads assorted throughout the array (in an exemplified bead-attached oligonucleotide sequence, each oligonucleotide respectively includes: a site of attachment (e.g., a cleavable site of bead attachment); a handle sequence (optionally, a universal handle sequence); a spatial barcode that is unique (or sufficiently unique) to each bead (as described above and as previously as noted); a unique molecular identifier (UMI); and 30 dT bases, which served as the capture region for the polyadenylated tails of mRNAs (referred to frequently in the literature as "oligo dT")). This high-resolution bead array was then used for transcriptome capture from sample tissue, which was prepared as described in the below Example and elsewhere herein.

Figure 1B:
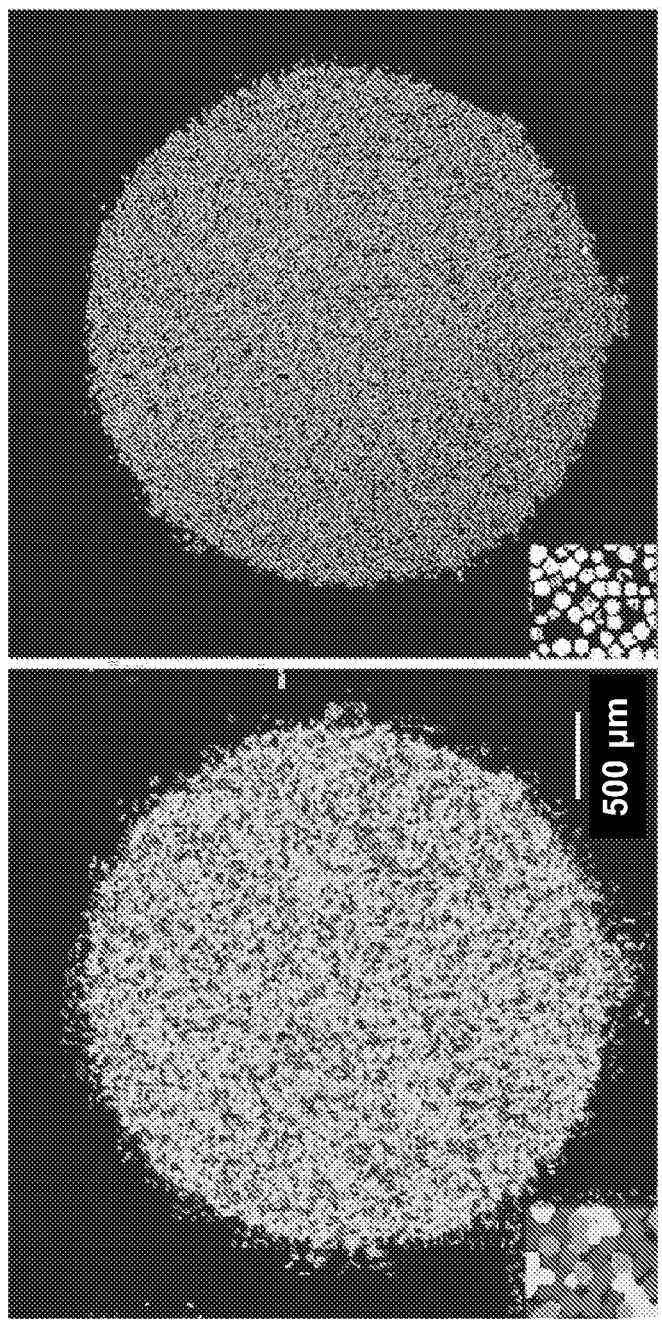
Figure 5A:
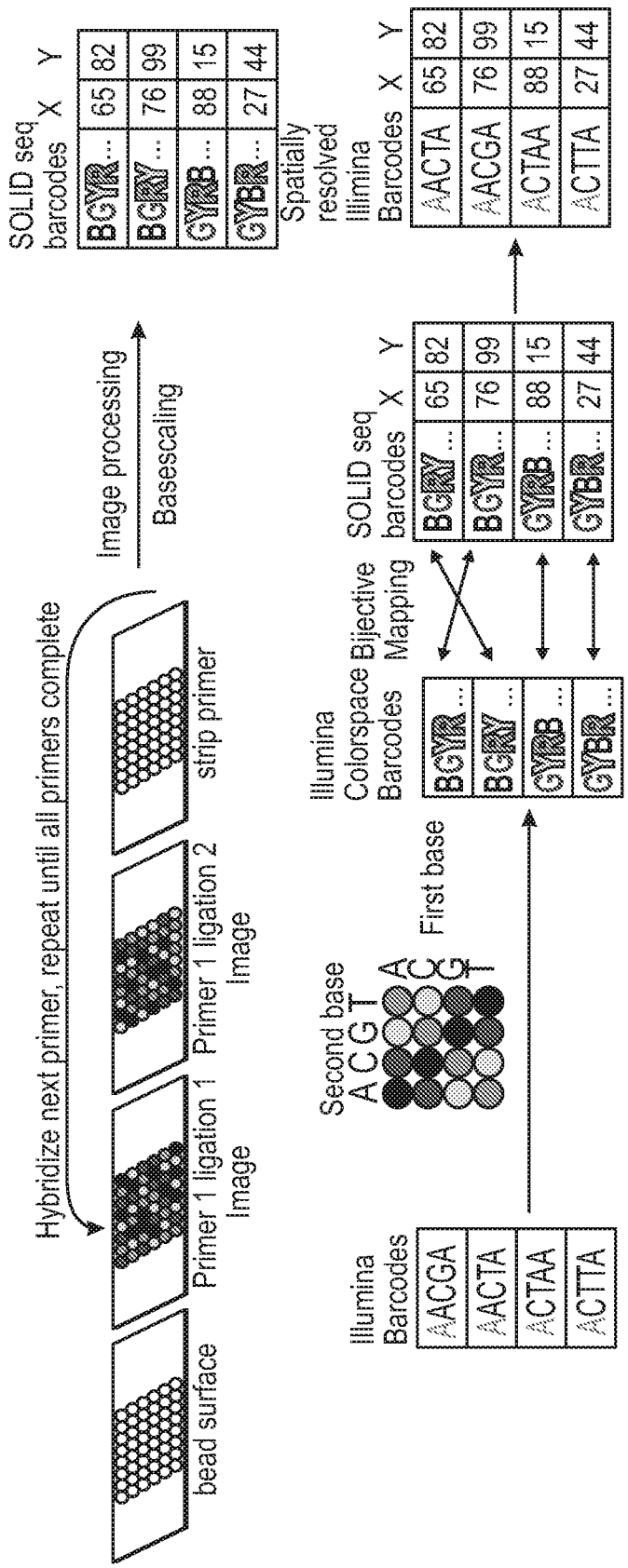
FIGS. 5A to 5D show a process and characteristics of the beads produced for use in the Slide-seq approach of the instant disclosure.
Figure 5B:
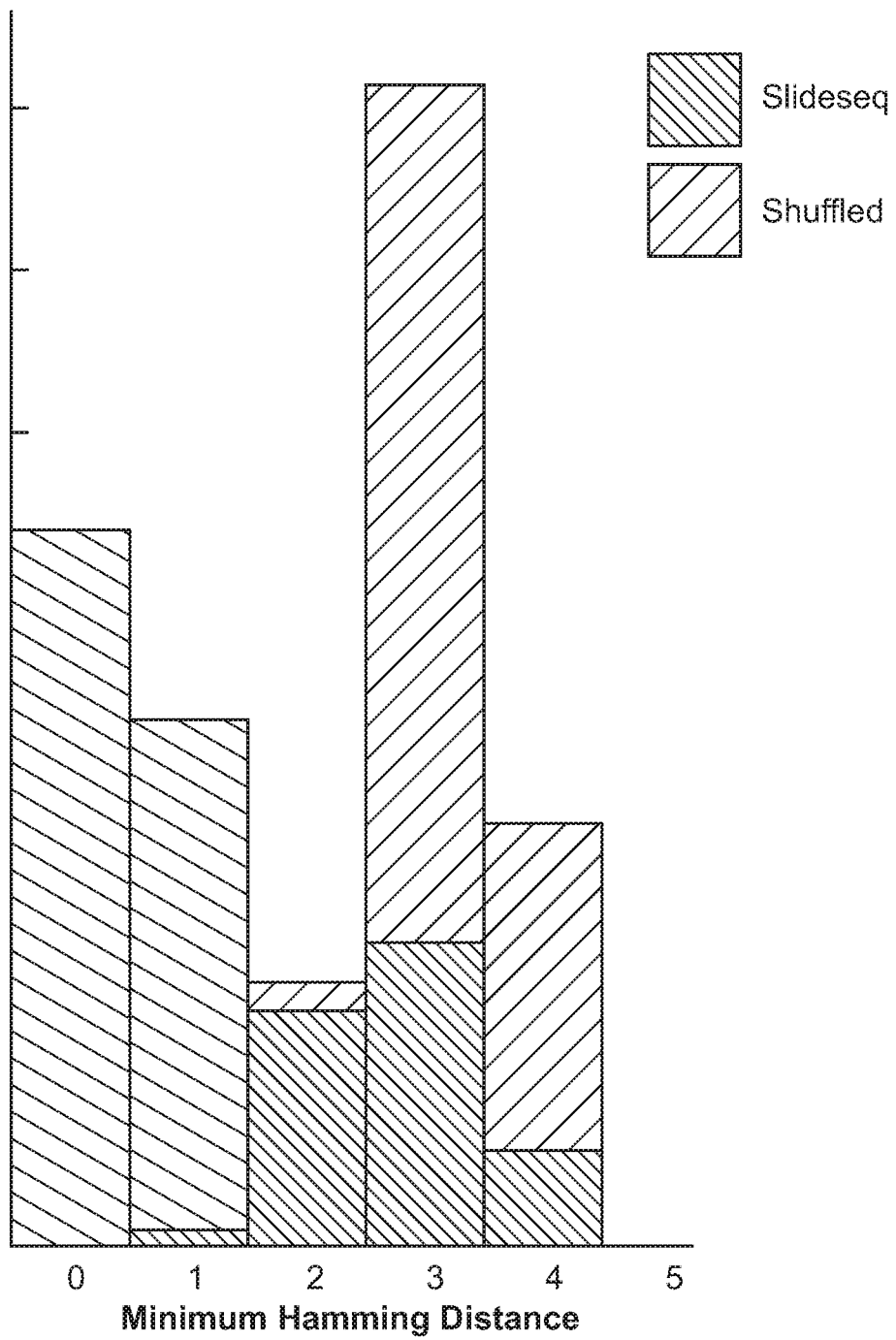
Figure 5C:
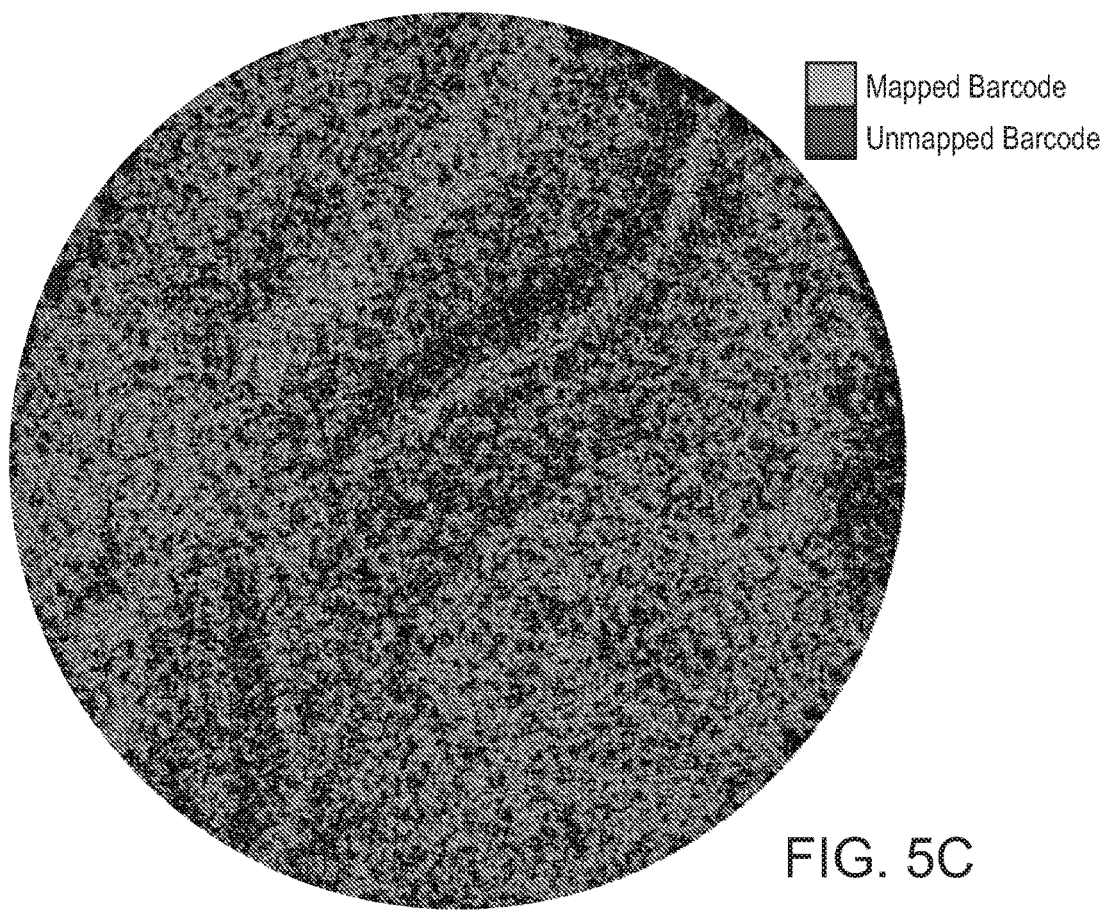
Figure 5D:
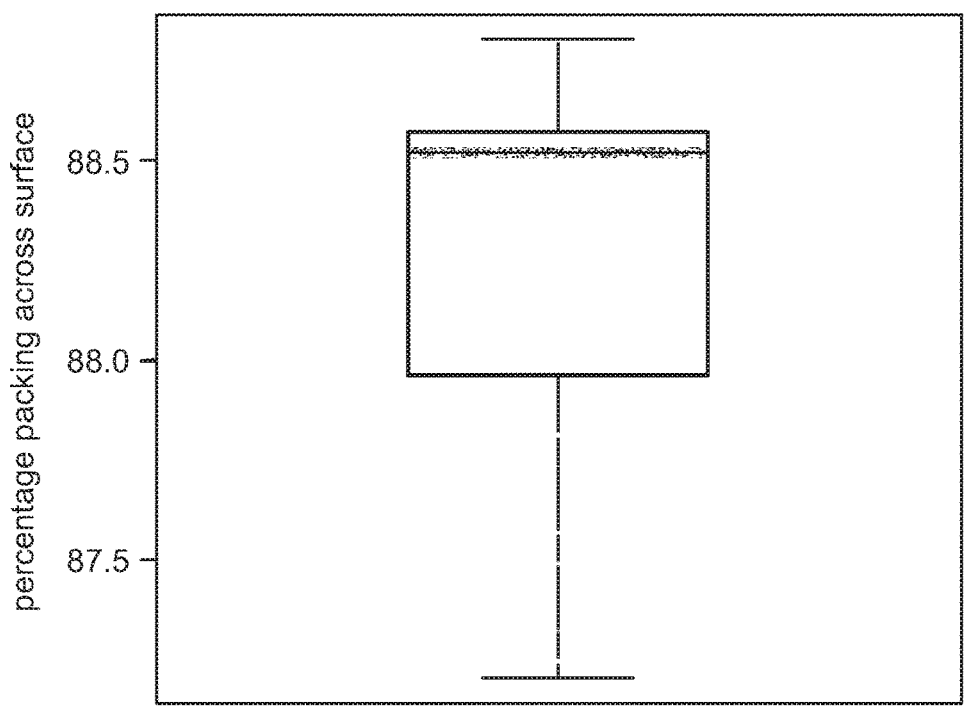

To develop Slide-seq, it was first examined whether barcodes could be arrayed randomly on a surface at high spatial resolution and their locations determined post-hoc. Split-pool synthesis barcoded oligonucleotide microparticles ('beads', 10 μm diameter), similar to those used by the Drop-seq approach to scRNA-seq (see, e.g., WO 2016/040476), were deposited onto a rubber-coated glass coverslip by evaporation, resulting in a packed bead surface which was termed a "puck" (FIGS. 5A to 5D, 88% packing). It was identified that the bead barcode sequences on the surface could be uniquely determined via in situ sequencing using the SOLiD sequencing-by-ligation chemistry (FIGS. 1B and 5A).

Figure 1C:
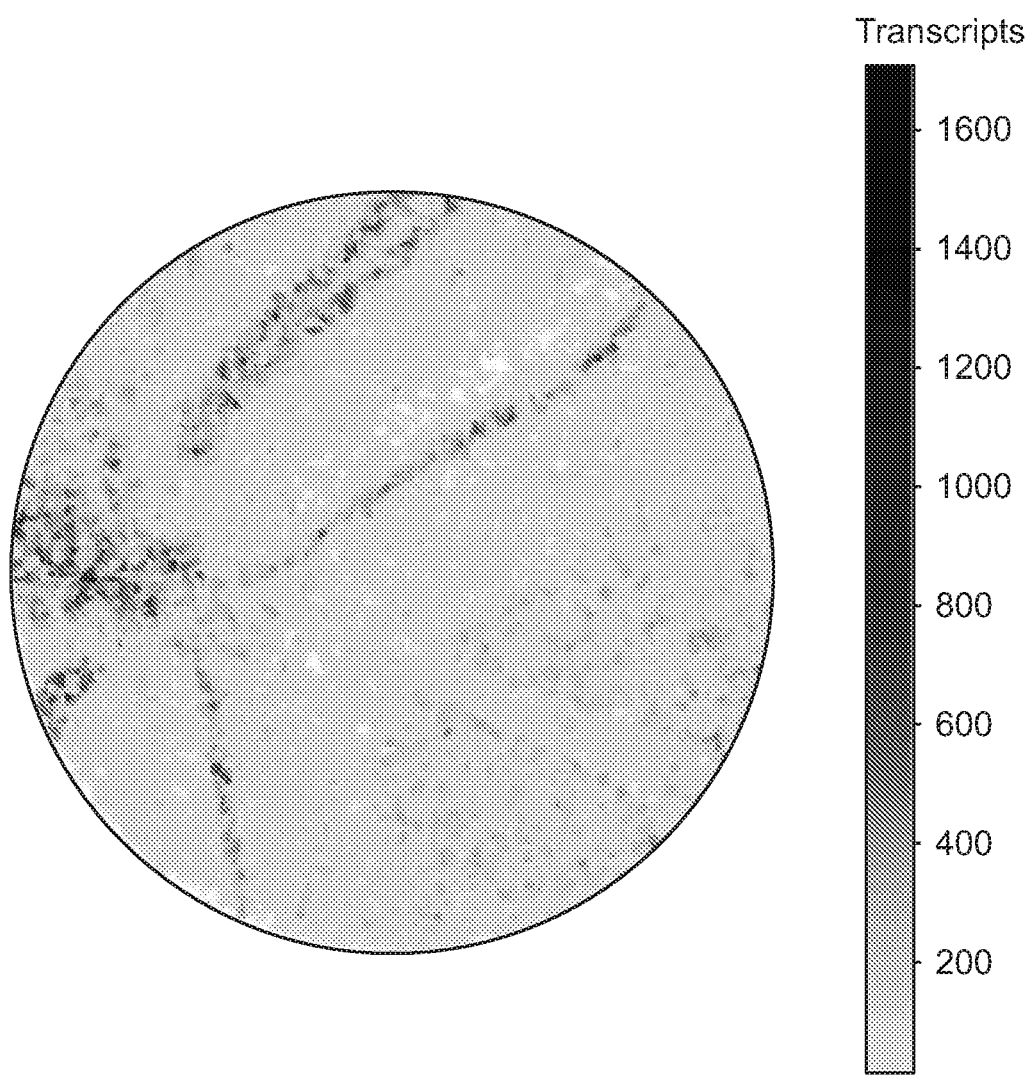
Figure 1D:
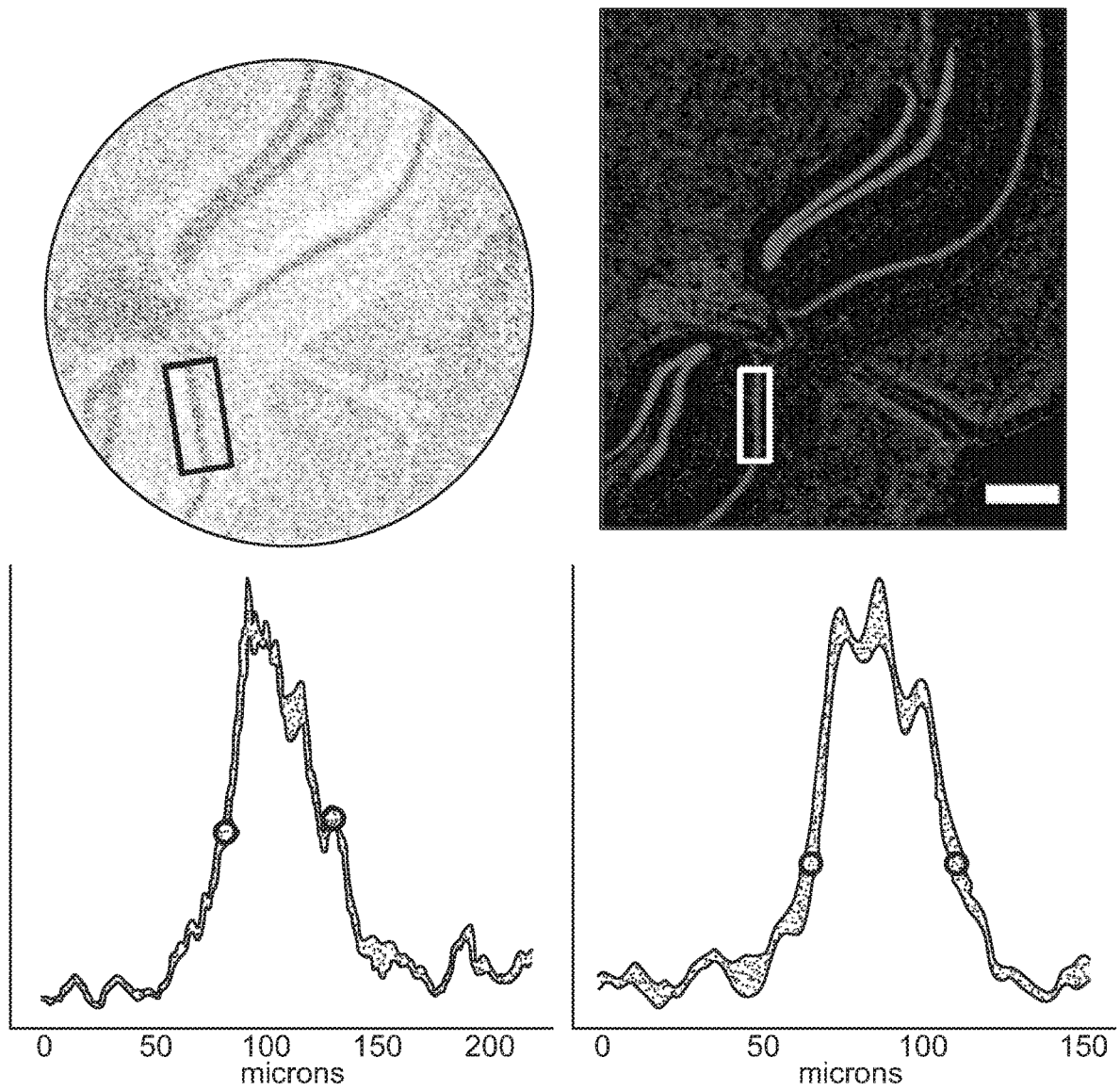
Figure 1E:
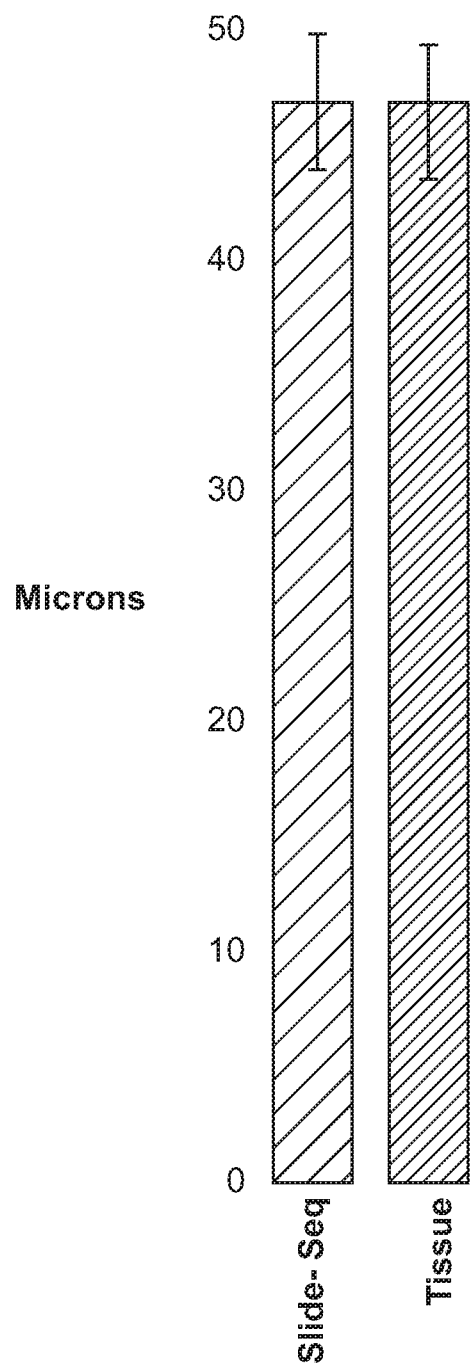
Figure 1F:
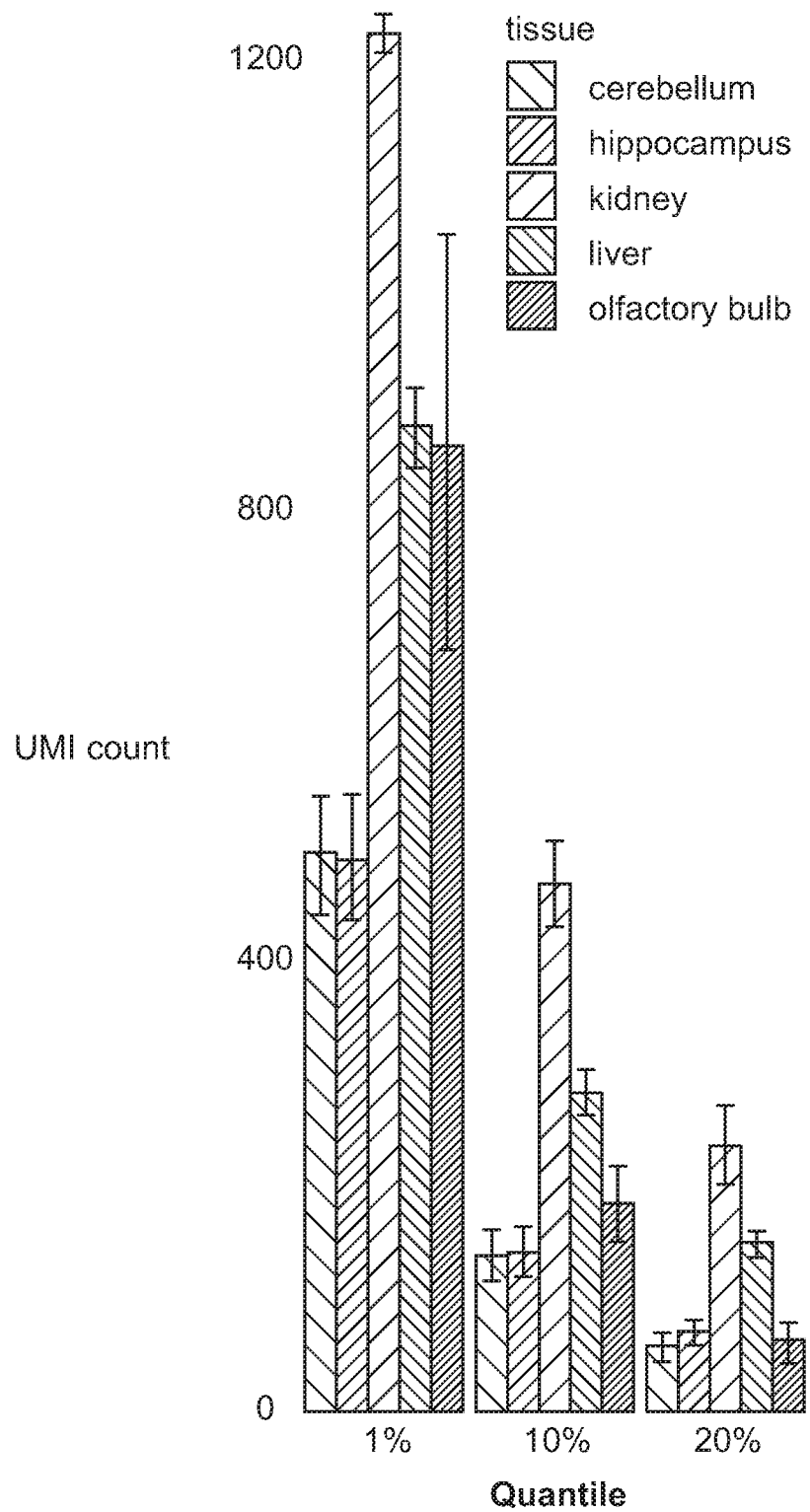

Example 3: A Glass Slide-Associated Barcode-Tagged Microbead Array Captured Transcriptomes with Robust Spatial Resolution To determine if the surface could capture RNA with high resolution, a protocol was developed wherein frozen tissue sections (~10 μm) were transferred onto the bead surface via cryosectioning (7). This process efficiently transferred RNA from the tissue to the surface, and subsequent processing of beads via standard single-cell library preparation pipelines generated 3'-end digital expression libraries. Performing this process on mouse hippocampal tissue slices, the distribution of transcripts across the puck was found to have recapitulated the distribution of cell bodies observed in the tissue (FIG. 1C). By comparing the width of CA1 observed in Slide-seq hippocampal data to that width observed in an adjacent, DAPI-stained tissue section (FIG. 1D), it was estimated that the length-scale of lateral diffusion of transcripts during hybridization was less than the width of an individual bead (FIG. 1E), which indicated that RNA was transferred from the tissue to the beads with high spatial resolution. Moreover, efficient capture was observed across a wide range of tissues, including brain, kidney, and liver (FIG. 1F).

Figure 2A:
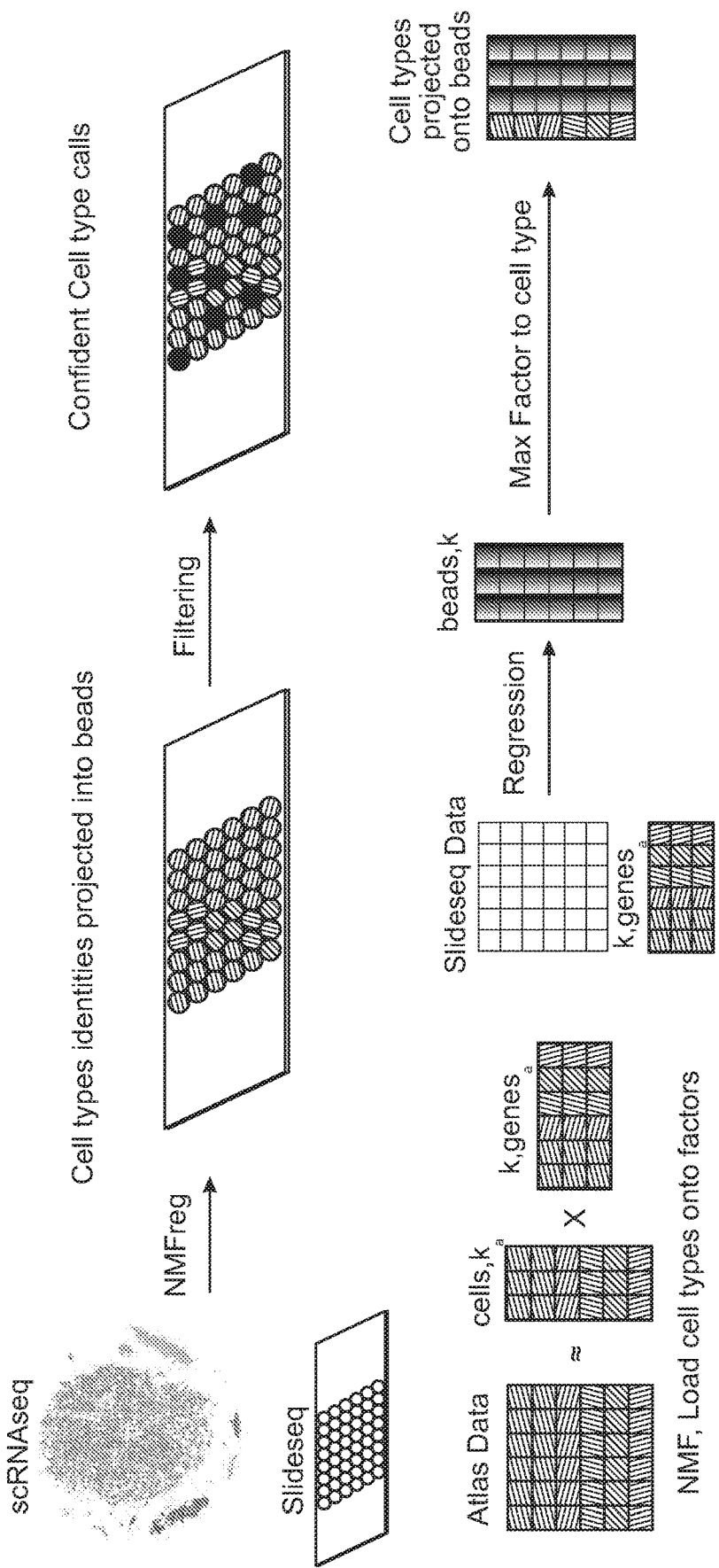
FIGS. 2A to 2F demonstrate localization of cell types using Slide-seq.
Figure 2B:
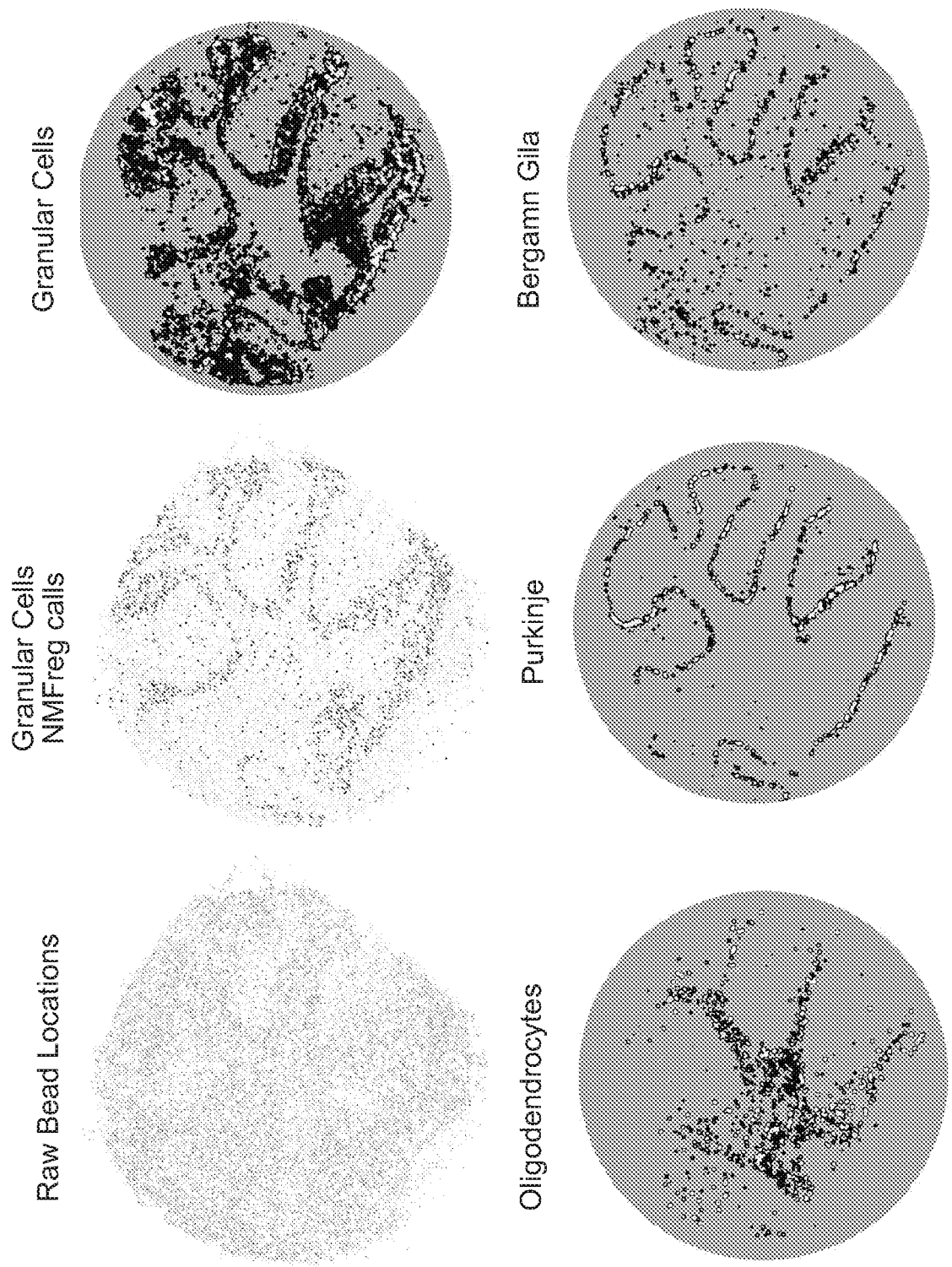
Figure 2C:
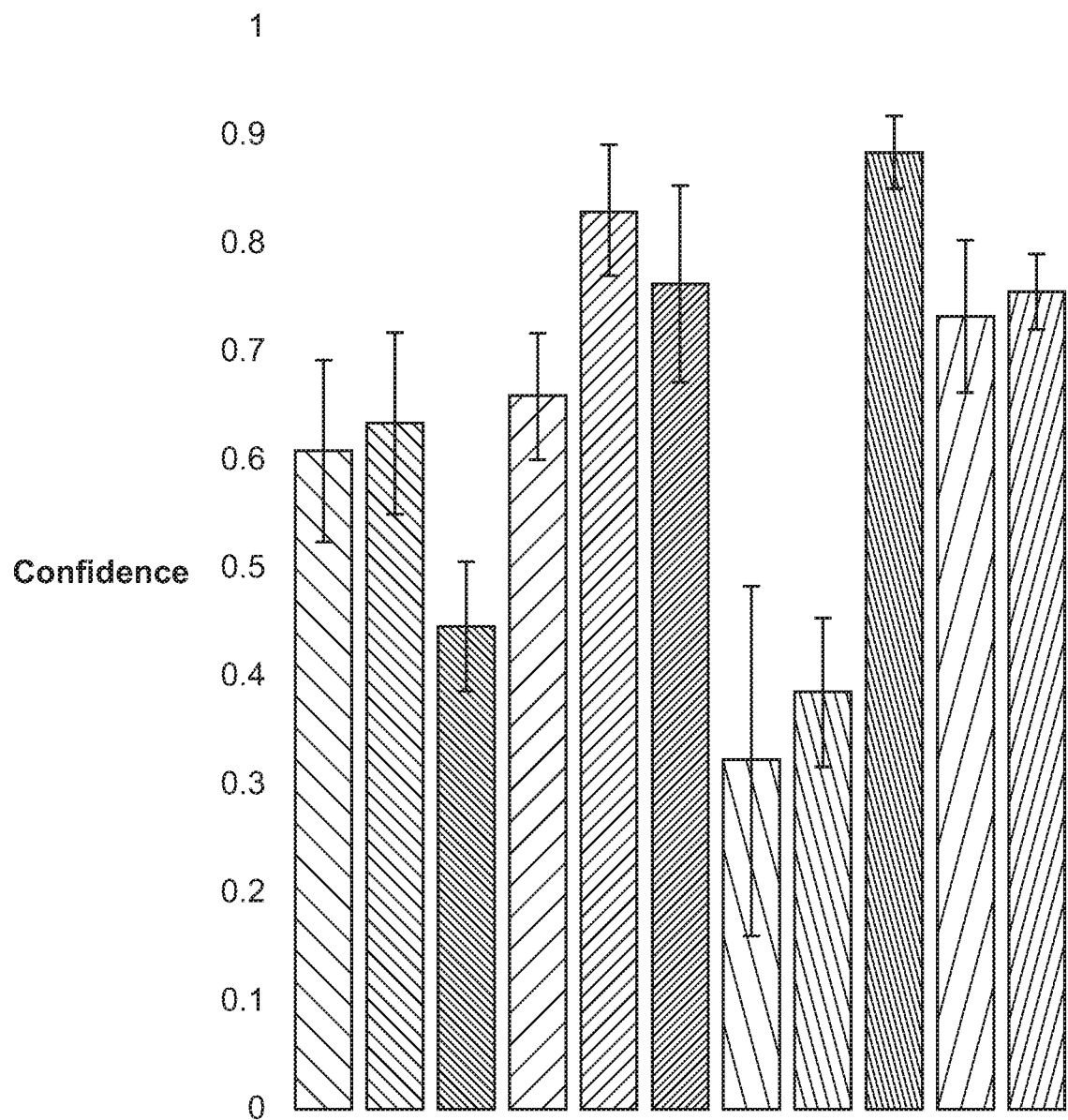
Figure 2D:
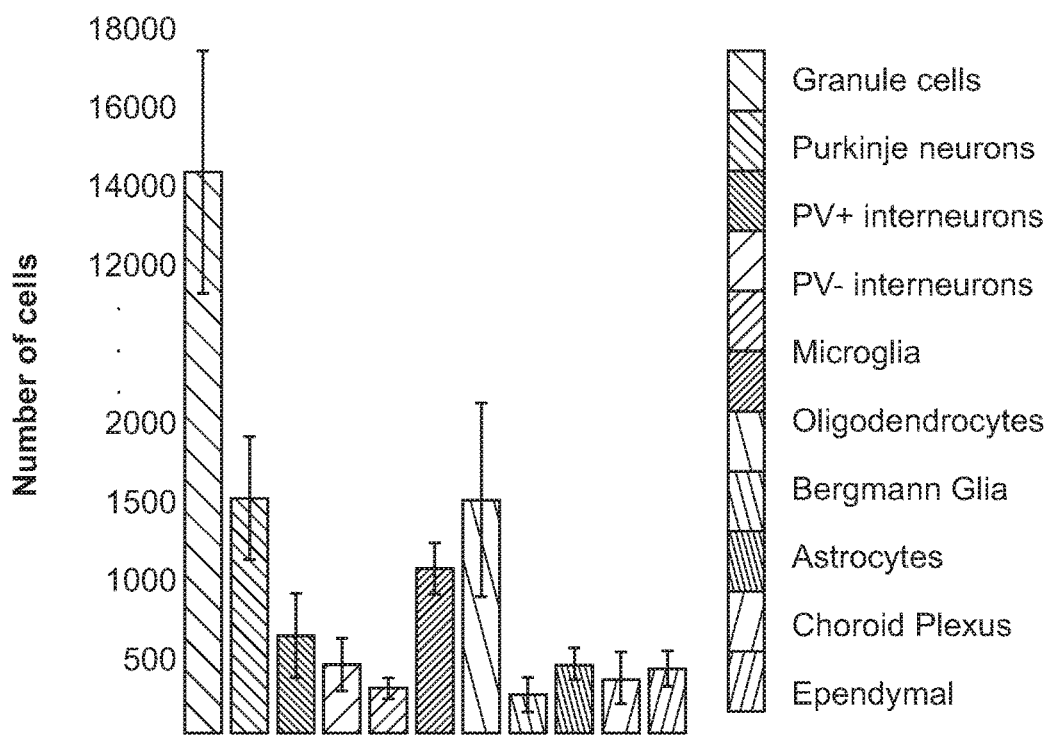
Figure 2E:
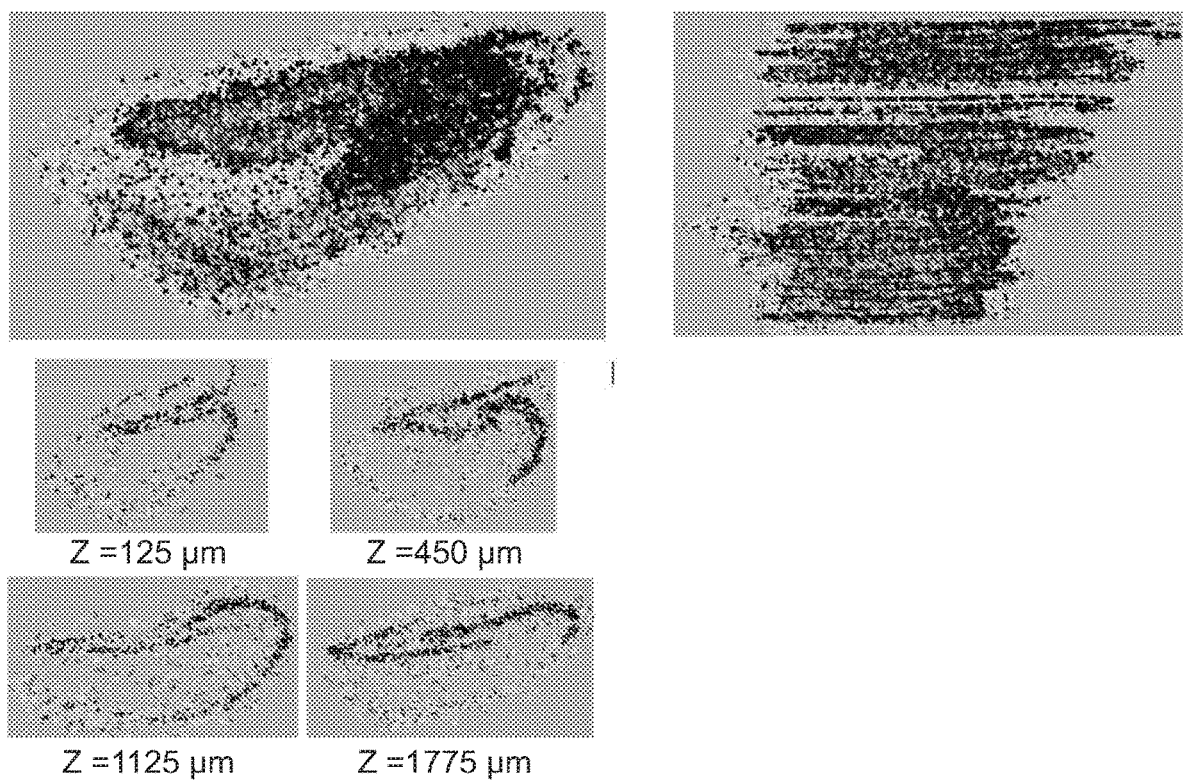

To determine whether cell types from scRNA-seq could be faithfully mapped onto spatially localized Slide-seq data, a protocol termed NMF Regression (NMFReg) was developed, for projecting expression vectors from Slide-seq beads onto the linear subspace spanned by factors obtained from NMF of single-cell atlas data (FIG. 2A). Application of NMFreg to cerebellar Slide-seq data recapitulated the spatial distributions of classical cell-types, such as granule cells, Purkinje cells, and Oligodendrocytes (FIG. 2B). By comparing the loading on the maximum factor following projection to the distribution of factors in NMFReg, it was possible to identify beads that could be confidently assigned to a single cell-type. On average, 61.4%±5.1% of beads processed by NMFreg could be confidently assigned (mean±std, N=7 cerebellar pucks). This varied by cell type, with 88.8%±3.2% of beads called as choroid being called confidently (mean±std, N=7 pucks), while 32.4%±16.1% of beads called as Bergmann glia were called confidently (FIG. 2C). Moreover, the high spatial resolution of the method was found to be key for assigning beads to cell types with high confidence: upon artificially reducing the resolution of the method, the lower resolution images failed to confidently map cell types in regions that were heterogenous in cell types present, whereas homogenous regions such as the granular layer of the cerebellum maintained identifiability (FIGS. 6A-6F). Importantly, the representation of cell types in Slide-seq more accurately represented the natural distribution of cell types than single-cell sequencing. This was due to the sampling of tissue in native contexts allowing for better representation of rare cell types: whereas Purkinje neurons make up only 0.7% of cerebellar single-cell atlas data, they made up 7.8%±1.3% (mean±std, N=7 pucks) of a cerebellar puck, in line with expectation from histological studies (FIG. 2D).

Figure 2F:
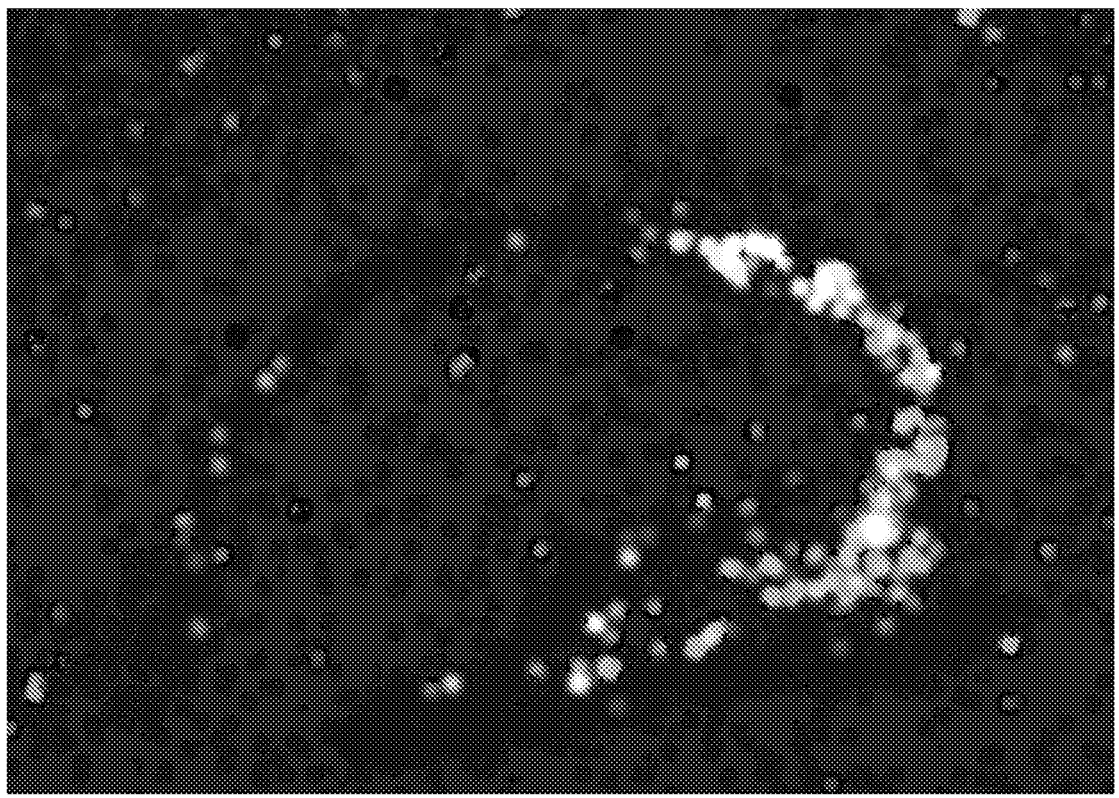

The Slide-seq protocol was identified to be straightforward to execute, and pucks could be produced at high-throughput. To demonstrate the scalability of Slide-seq, it was applied to 70 tissue slices from a single dorsal mouse hippocampus, covering a volume of 39 cubic millimeters, with roughly 10 μm resolution in the dorsal-ventral and anterior-posterior axes, and ~20 μm resolution in medial-lateral axis. This region contained an estimated ~1 million beads that could be confidently assigned to single cell types. Pucks were computationally co-registered along the medial-lateral axis, allowing for visualization of gene expression in the hippocampus at high resolution in three dimensions (FIG. 2F). Metagenes comprised of markers for CA2 and for the hippocampal hilum were plotted on hippocampal pucks, and it was identified that they were highly expressed and specific for the expected regions (FIG. 2F), which confirmed the ability of Slide-seq to localize both common cell-types and more subtle cellular subtypes. The entire experimental processing for these 70 pucks (excluding the time and equipment required to make the pucks) required roughly 40 person-hours, and only standard experimental apparatus associated with cryosectioning and next generation sequencing. Thus, Slide-seq was readily scalable to the generation of three-dimensional atlases of spatial gene expression.

One key advantage that the Slide-seq approach of the instant disclosure has provided by allowing for spatial RNA sequencing with near-single-cell resolution is the ability to identify genes that are expressed in rare, spatially localized cell populations. The instant approach has particular power when it has been combined with the NMFReg algorithm herein, which has enabled the systematic identification of spatially localized cellular subpopulations, and spatial patterns of gene expression within known cell types. A non-parametric, kernel-free algorithm was developed to identify genes with spatially non-random distribution across the puck, where "random" was defined with reference to a null model in which transcripts were redistributed among beads while preserving the total number of transcripts per bead (FIGS. 7A-7E). A cluster of PV interneurons were identified in one corner of a coronal cerebellum puck that were marked by the little-studied gene Opioid Growth Factor Receptor Like 1 (Ogfrl1) (FIG. 3A), which was determined herein to be a highly specific marker for interneurons in the molecular and fusiform layers of the dorsal cochlear nucleus (FIG. 3B), also marked by Prkcd and Atp2b1. Without wishing to be bound by theory, this population was likely the cartwheel cells of the dorsal cochlear nucleus, which have been described previously as excited by the parallel fibers of the cochlear nucleus and have been believed to be involved in the generation of feedforward inhibition (8, 9). The existence of a specific genetic marker for this cell population is expected to enable controlling of the cell population genetically. The instant algorithm also identified Rasgrf1 as having significant nonrandom spatial distribution within the granule cell layer of the cerebellum (FIG. 3C), a pattern previously identified using ISH data (10) (FIG. 3D), thus validating the approach. Remarkably, however, a search for other genes with similar spatial distribution revealed no genes that were either correlated or uncorrelated with Rasgrf1, which indicated that if there were other genes with similar expression patterns to Rasgrf1, they were expressed at such low levels as to be undetectable by the Slide-seq process of the instant disclosure.

Figure 8:
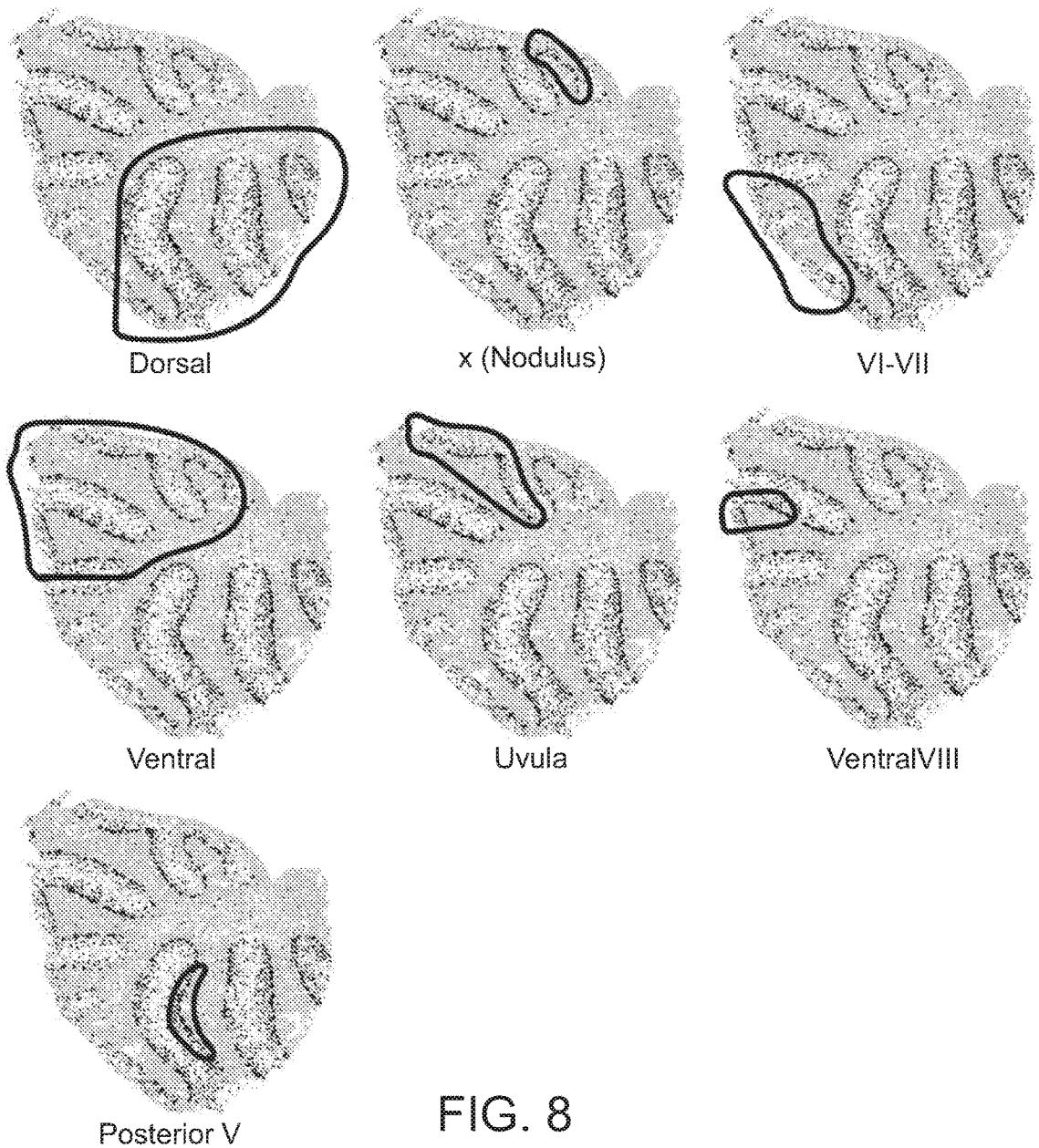
FIG. 8 shows images of regions chosen for analysis in FIGS. 3I and 3J. Note that the region chosen as lobule X (nodulus) and the uvula are more properly the anterior nodulus and anterior uvula, respectively. These regions were chosen because they appeared by inspection to have the most interesting variation between metagenes.

Whether the discovery of patterns of spatial gene expression in Slide-seq could be greatly assisted using patterns of correlation discovered in less sparse single-cell sequencing data was then examined. The cerebellum has been described as marked by parasagittal bands of gene expression in the Purkinje layer which are known to correlate both with the origins of afferents and targets of efferents (11). Several genes have been found to have similar or complementary parasagittal expression (12-15), but a systematic classification of banded gene patterns has been heretofore lacking. The significant gene calling algorithm of the instant disclosure was applied to the beads marked by NMFreg as Purkinje cells in the cerebellum, and this approach successfully identified Aldoc, a canonical marker for cerebellar banding, as well as Cck, Plcb4, Nefh, and several other genes. Applying a spatial correlation detection algorithm (7) to these genes led to the identification of a total of 31 genes, which were found to cluster into two sets, one marked by Aldoc and one marked by Cck (FIG. 3E). These sets included several genes that were previously known to be involved in cerebellar patterning, as well as many genes not previously associated with cerebellar banding patterns, including Olfm1 in the Aldoc cluster and Creg1, Cox5a, and Itgb1bp1 in the Cck cluster. Metagenes were formed for each of the 31 genes consisting of all genes with a correlation greater than 0.3 in single-cell Purkinje data (FIG. 8). In the sections that were examined, the Aldoc and Cck metagenes thus plotted revealed a clear pattern, with the Aldoc metagene concentrated in the ventral cerebellum, including the nodulus (lobule X) and the region between lobules VI and VII, and the Cck metagene concentrated dorsally, and excluded from those regions (FIG. 3F), patterns that were recapitulated in ISH data of similar sections (FIGS. 3G and 3H).

Figure 3K:
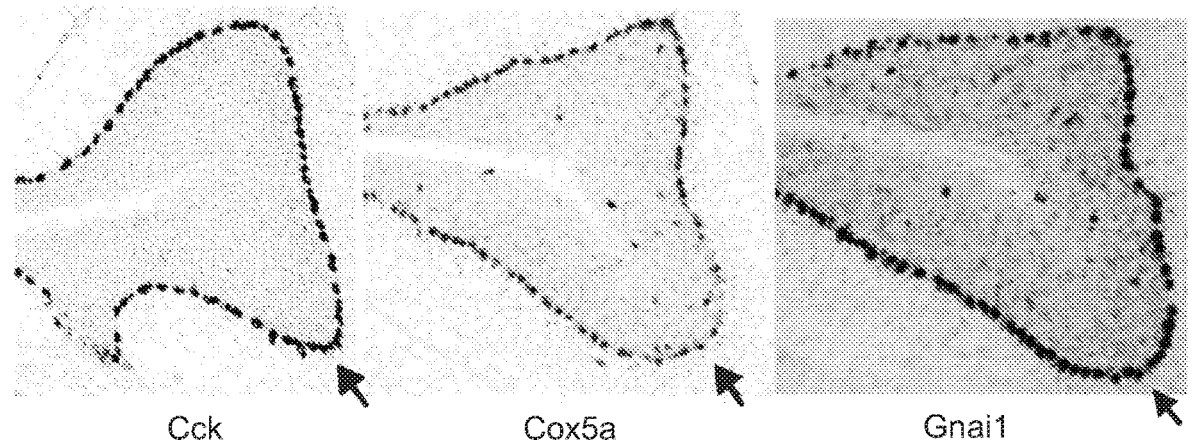
Figure 3L:
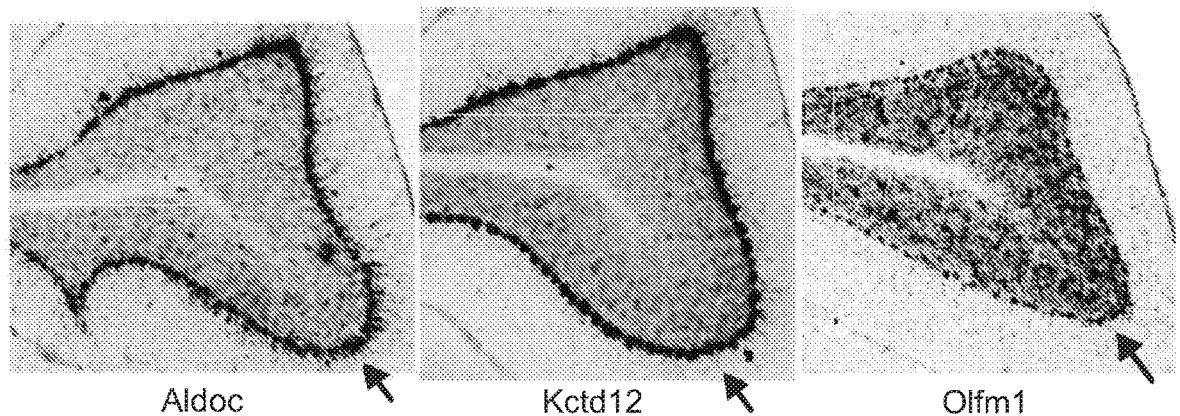

To investigate whether the Aldoc and Cck patterns could describe all of the variation in gene expression we observed across the cerebellum, a cerebellar puck was divided into 7 morphologically-defined regions (shown in FIGS. 3G and 8) and the expression of all 31 of the spatially localized metagenes above was quantified in all 7 regions (FIG. 3I). The correlation between metagene expression was then calculated in different subregions. Although all the other regions that were examined correlated significantly with either the bulk dorsal or bulk ventral expression, surprisingly, gene expression in the ventral horn of lobule VIII did not correlate with expression in any other region at the $p<0.001$ level (corresponding to Bonferonni-corrected $p<0.05$) (FIG. 3J). Examination of genes in the Allen ISH database supported this hypothesis: Cck was strongly expressed in lobule VIII in similar sections, but Cox5a (in the Cck cluster) was apparently downregulated on the ventral side of lobule VIII, whereas Gnai1 (also in the Cck cluster) was apparently upregulated there (FIG. 3K). Likewise, Aldoc and Kctd12 were expressed strongly in lobule VIII in similar sections, but Olfm1, which is in the Aldoc cluster, was excluded (FIG. 3L). This likely points to a unique pattern of expression for lobule VIII, which would distinguish it from the predominant Aldoc/Cck banding pattern of the cerebellum. Thus, the Slide-seq approach of the instant disclosure enabled the discovery of regions of tissue with differential gene expression that did not otherwise emerge from anatomical or single-cell sequencing analysis.

Finally, to illustrate the utility of Slide-seq for studying biological responses to pathology, the approach was applied to a model of traumatic brain injury. Cortical injuries were induced using an intracranial injection protocol with no liquid injection, and mice were sacrificed 2 hours, 3 days, or 2 weeks following injection. The injection site was visualized in Slide-seq data by the presence of hemoglobin transcripts (for 2 hours, FIG. 4A), or transcripts of Vim, Gfap, and Ctsd (for 3 days and 2 weeks), and the regions of the puck thus identified matched the location of the injection site as determined by histology (FIGS. 4B and 4C). Using the overlap algorithm developed for the sagittal cerebellum analysis, all genes that correlated spatially with those transcripts were identified. At the 2 hour timepoint, the only gene identified in this way was Fos, although it was also found that rRNA correlated significantly with the hemoglobin genes (FIG. 4A). Because rRNA was not correlated with hemoglobins on other, non-injury pucks (FIGS. 10A to 10D), and because its correlation to the injury site markers disappeared by the 2 week timepoint, it was likely that upregulation of ribosomal RNA transcription constitutes a previously unidentified aspect of the immediate response to acute CNS injury, analogous to the rapid transcription of rRNA in the spinal cord following motoneuron injury (16).

At the 3-day timepoint, in contrast to the 2 hour timepoint, many genes were observed at the injection site marking a robust astrocytic and immune response. Running NMFreg on the injection pucks, a structured distribution of injury-associated cell types was observed around the injection site at both the 3-day and 2-week timepoints. At the 3-day timepoint, beads assigned to the microglia/macrophage cluster were observed as localized to the lesion, surrounded immediately by a distinct layer of cells expressing mitosis-associated factors, followed by a layer of astrocytes (FIG. 4D), which suggested that mitosis occurred primarily in contact with the lesion itself. In contrast, at the 2 week timepoint, beads assigned to the microglia/macrophage cluster were observed filling the lesion, a layer of astrocytes around the lesion was also observed but was depleted in the middle, and finally neurons around the lesion were observed, offset some from the beginning of the astrocyte layer, which indicated that mitotic lesion associated events had ceased by two weeks (FIG. 4E). Measuring the thickness of these features (FIG. 4F), the thickness of this mitotic layer was found at 3 days to be 92.4 μm±11.3 μm (mean±sterr, N=3), which indicated the presence of several cell widths of mitotic cells. By contrast, the astrocytic scar layer, defined as the distance between the half-maximum of the astrocyte layer and the half-maximum of the neuron layer, was 36.6 μm±13.4 μm (mean±sterr, N=6), which indicated that only one or two cell widths were present between the lesion and the nearest neurons. Finally, penetration of beads assigned to the microglia/macrophage through the astrocytic scar and into neuron-rich regions was observed. Measuring this penetration, it was found to be 39 μm±17.8 μm (mean±sterr, N=6), which was statistically indistinguishable from the thickness of the scar. Finally, it was examined whether macrophages were localized differently from microglia. Counts of the Lyz2 gene, which was highly expressed on the puck and very specific for macrophages, were plotted and the distance between the half-maximum of the Lyz2 distribution and the half-maximum of the microglia distribution was observed to be 49.7 μm±5.9 μm (mean±sterr, N=6), which indicated that although microglia inhabited both the astrocytic layer of the scar and the lesion location itself, macrophages only inhabited the lesion. Thus, the Slide-seq approach of the instant disclosure enabled precise dissection of the spatial relationships between different cell-types, with resolution on the order of individual cells.

Figure 4H:
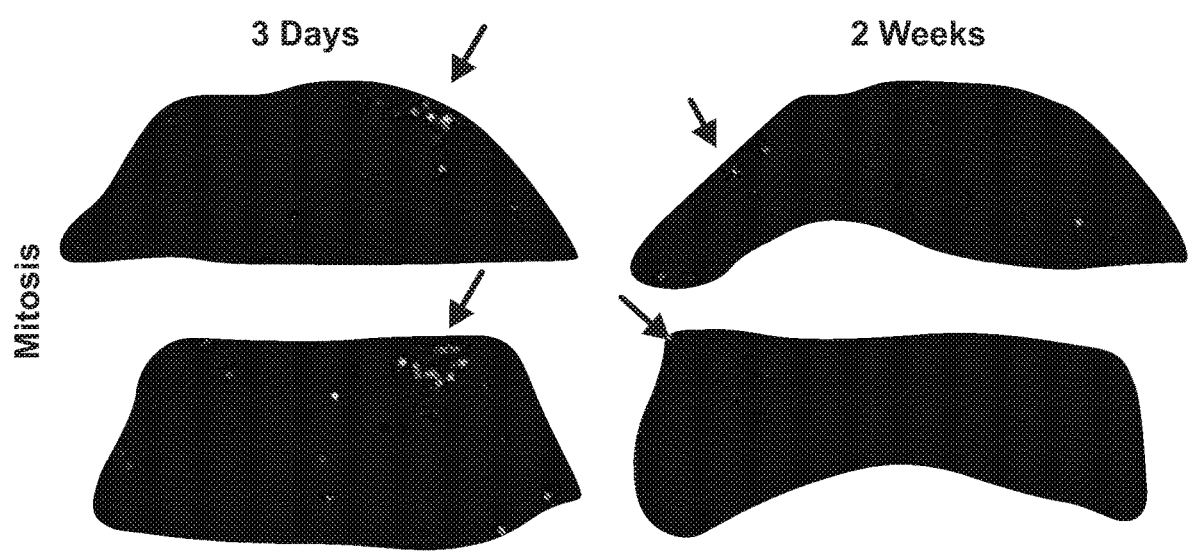
Figure 4I:
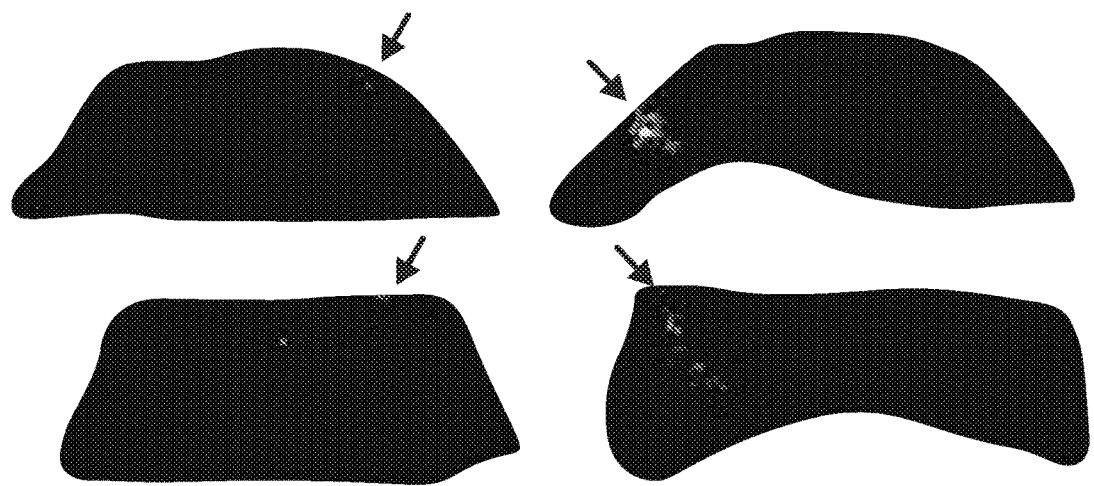
Figure 4J:
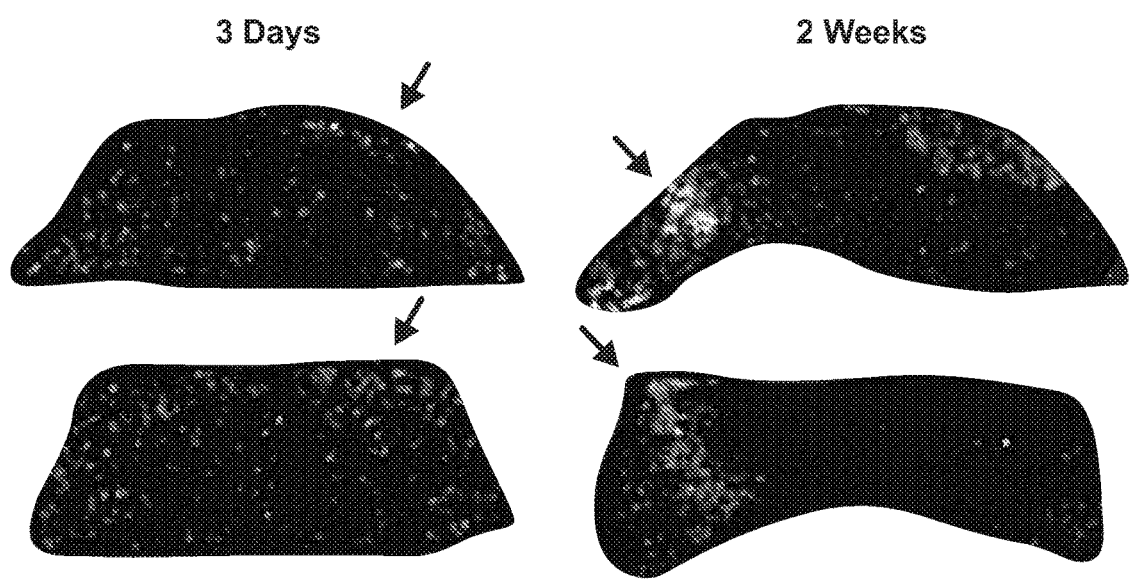
Figure 4K:
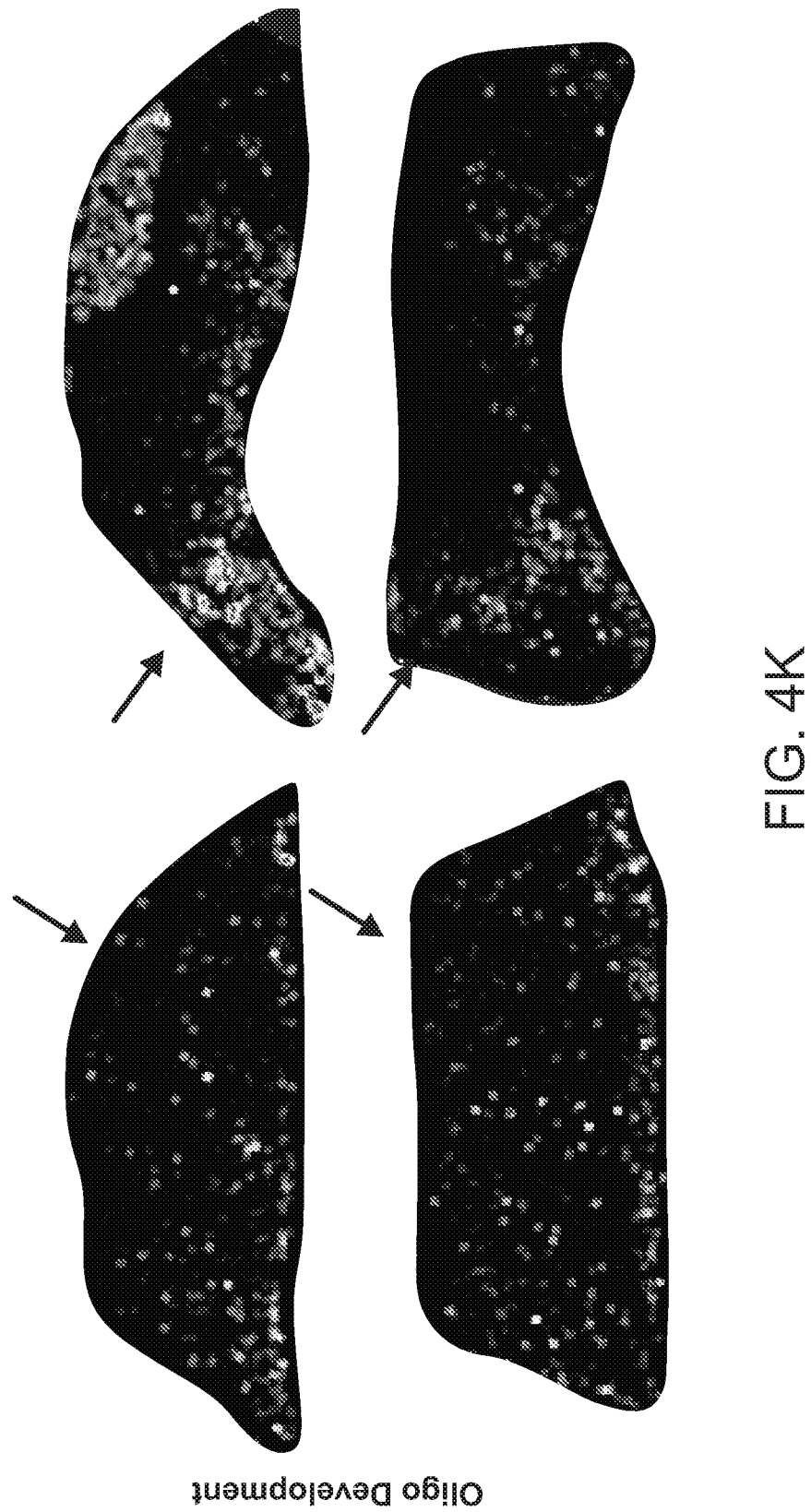
Figure 11:
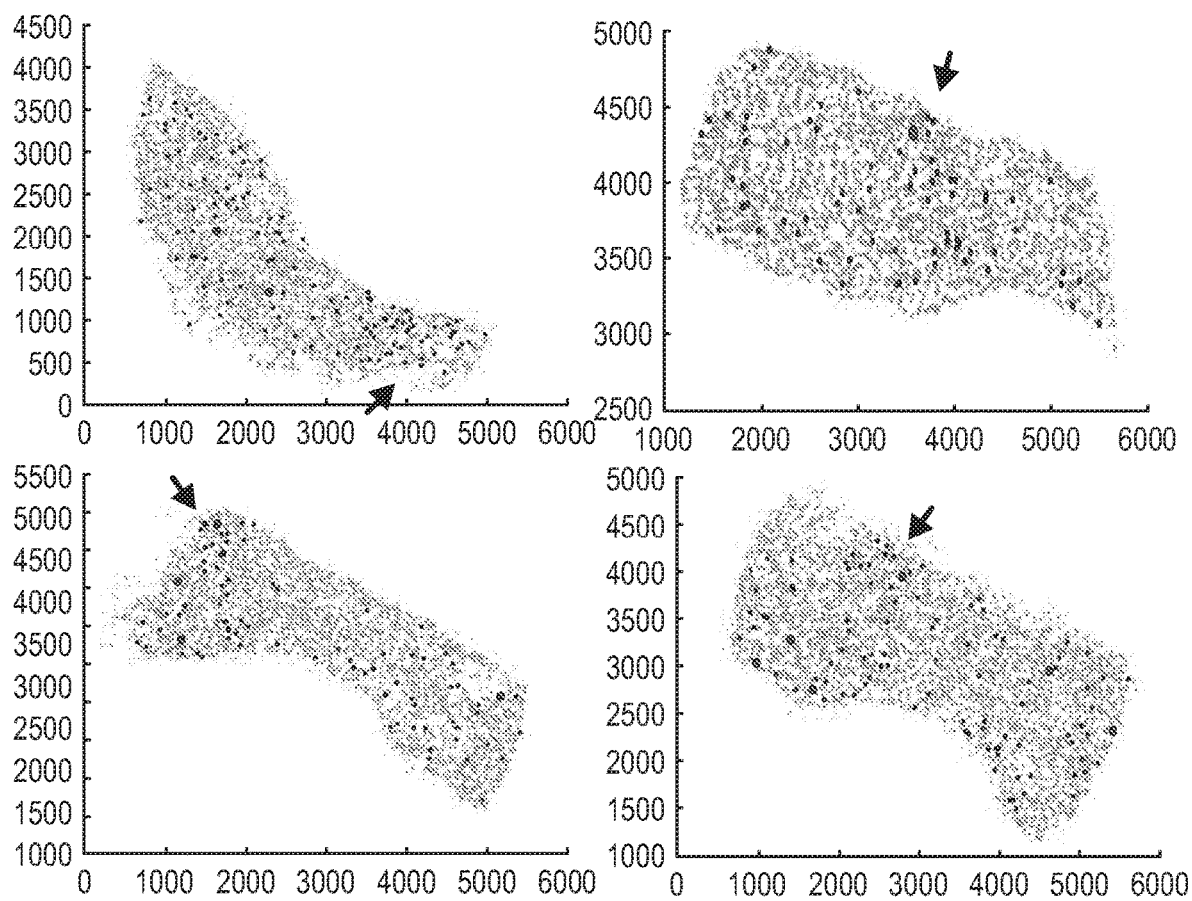
FIG. 11 shows beads expressing Sox4 and Sox10, shown in dark gray for ten pucks from the 2 week injection timepoint. The radius of dark gray beads is proportional to the total counts of Sox4 and Sox10 observed. The injection site is indicated with an arrow.

To investigate other changes in gene expression between the 3-day and 2-week timepoints, the overlap analysis was performed to identify genes correlating with Vim, Gfap, and Ctsd at the 3 day timepoint and the 2 week timepoint. 843 such genes were thereby identified at the 2-week timepoint, and only 293 were identified at the 3 day timepoint. To identify transcriptional programs that were differentially engaged at each of the two timepoints, gene ontology (GO) analysis was applied to the set of 685 genes correlated at 2 weeks and not 3 days, and to the set of 135 genes correlated at the 3 day timepoint and not the 2 week timepoint. Remarkably, the only GO annotations significant in the latter set of 135 genes were those relating to chromatid segregation, mitosis, and cell division, including Nes, Top2a, Cenpe, Cenpf, Prc1, Birc5, Smc4, and Tuba1c. Plotting these genes confirmed that although these factors localized to the injury site 3 days after injection, the localization disappeared after 2 weeks (FIG. 4H). Instead, several GO annotations were observed that were significant in the former set of 685 genes relating to the immune response, such as antigen presentation on MHC type I (FIG. 4I), as well as programs relating to cell development, such as gliogenesis (FIG. 4J) and oligodendrocyte development (FIG. 4K). The degree to which Ng2 glia differentiate into oligodendrocytes following a focal gray matter injury has been a point of controversy (17), however, it was confirmed herein that both Sox4 and Sox10 localized to the region surrounding the injury, which indicated the presence of immature oligodendrocytes (FIG. 11). Thus, cell proliferation occurred on the order of days following injury, with the period between 3 days and 2 weeks identified as critical for fate determination of newly born cells following traumatic brain injury.

It was then examined whether there might be other changes in gene expression in the surrounding tissue that were not immediately localized to the injection site. Remarkably several immediate early genes, including c-Fos, Arc, Npas4, and JunB, were identified as upregulated in a large region around the injection site at both the 3-day and the 2-week timepoints (18-20). Running the overlap analysis on these genes at the 2-week timepoint unexpectedly revealed a number of other genes that also seemed to localize near the wound, including Egr1 (a neuronal gene), Egr4 (a neuronal gene), Lmo4 (a neuronal gene), Nr4a1 (a neuronal gene), Slc16a13 (a glial gene, expressed strongly in fibroblasts), Rgs4 (a neuronal gene), Grin2b (a neuronal gene), and C1ql3 (a neuronal gene). By contrast, the only gene significantly correlated with these IEGs at the 2-hour timepoint was Snap25, which was likely a false positive. A metagene was then formed out of the resulting 12 genes, and a clear localization of the metagene to the region around the wound was observed (FIG. 4G). This increase in gene expression decreased with distance away from the injection site and reached its half maximum 0.722 mm±0.191 mm away from the injection site (mean±sterr, N=4 measurements). The specificity of some of these genes (such as Npas4 (21)) for neuronal expression prompted the conclusion that acute intracranial injury led to alterations in the pattern of gene expression and likely activity in nearby neurons for weeks following the injury.

Thus, the Slide-seq approach of the instant disclosure has enabled the spatial analysis of gene expression in frozen tissue with high spatial resolution and easy scalability to large tissue volumes. Combined with single cell atlas data the instant disclosure has been able to identify the positions of cell types in tissue, and to identify novel patterns of gene expression and the responses to perturbations within those cell populations. Slide-seq can thus be used to facilitate the identification of rare cell types and novel, spatially restricted patterns of gene expression that are difficult to isolate in single-cell sequencing.

Example 4: "Puck-In-A-Tube" Array Processing

The current example provides an additional option for array processing. In this example, glass coverslips containing the arrays were cut into small pieces and placed into 1.5 mL tubes for processing. The approach was termed "puck-in-a-tube," and it provided a surprisingly substantial improvement to the instant processes, as it allowed for higher throughput and easier processing of the "pucks" of the instant disclosure.

Example 5: Bead Deposit into Microfabricated Well Arrays

The current example provides an additional option for array design. In this example, beads were deposited into microfabricated well arrays, rather than adhered onto the surface. Well arrays of the correct size were made such that each well could hold exactly one bead. Beads were then deposited into the wells by evaporation in a centrifuge, exactly in the same way that pucks were formed on the liquid tape surface, as described above. However, rather than washing with water afterwards, as was performed above when forming the liquid tape surface, a brush was used to remove all of the beads that were not in wells. Many different methods for loading beads into the hexagonal array were attempted, such as by evaporation, and the instantly described method was identified to work by far the best. Tissue was then deposited onto the well array and centrifuged, so that the tissue was forced into the wells with the beads. A digestion buffer was then added, which lysed the tissue, causing the RNA of the cells of the tissue to transfer onto the beads in the wells. Reverse transcription was then performed on the well contents, and beads were then removed from the wells by sonication (or in an alternative embodiment, the cDNA can be cleaved by UV light). As for the above Examples, several methods were attempted in the instant example, and the methods now recited were identified as the best.

Example 6: Photocleavable Attachment of Beads to Solid Support

The current example provides an additional option for collecting the cDNA of the above-referenced Examples from beads. Beads as described above are attached reversibly to the liquid tape-coated surface of the above Examples. In the current example, photocleavable beads are employed, where the cDNA can be released from the beads using UV light. Photocleavable attachment of beads to solid support (and UV-mediated release from solid support) is thereby provided.

Example 7: Bead Binding of Specific Transcripts (Non-Poly(A) Primers)

The current example provides an option for binding of specific transcripts, rather than non-specific binding of all poly(A)-presenting transcripts. In this example, the beads have primers against specific transcripts, thereby providing specificity to transcript isolation process.

Design and use of probes capable of binding specific transcripts allows for performance of targeted sequencing via use of the Slide-seq platform of the instant disclosure, e.g., by modifying the beads of the Slide-seq array with targeted capture sequences. Such targeted capture sequences bind and enrich for specific sequences from the transcriptome, for example, T Cell receptor sequences, low expressing transcripts such as transcription factors, as well as synthetic transcripts such as guide-RNAs.

Example 8: Reusable Barcode Array

The current example provides a version of the instant compositions and methods in which the barcoded array is reusable. In this method, cDNA is generated and then the second strand can be synthesized. The second strand (carrying the barcode location) can then be released from the array, and the cDNA can be cleaved using a restriction enzyme (e.g., NmeAIII or MmeI) to reveal the poly(A) tail on the array again, allowing the array to be reused. A reusable barcode array embodiment is thereby provided.

Example 9: Transcript-Specific Amplification

The current example provides a version of the instant compositions and methods in which only some transcripts are amplified from the bead array. Similar to the specific transcript capture approach of Example 7 above, such specific transcript amplification allows for specific genes to be interrogated with fewer reads on the sequencer.

In a further embodiment, libraries can be generated off the beads multiple times, by multiple amplification steps. This approach is particularly useful for generating untargeted and targeted libraries from the same beads. Various additional options for library generation are thereby provided.

Example 10: Arrays of Barcoded Oligonucleotide Clusters

The current example provides an additional format of the instant disclosure in which the array, rather than consisting of barcoded beads, instead consists of barcoded clusters of oligonucleotides on a surface. Such an array can optionally be generated in an Illumina® sequencer, by flowing barcoded oligonucleotides into the sequencer, allowing the sequencer to amplify the oligonucleotides by bridge amplification, sequencing the barcodes in the sequencer, and then cleaving the oligonucleotides with a restriction enzyme to generate a poly(A) tail. An array comprising of barcoded clusters of oligonucleotides on a surface is thereby provided.

Example 11: Long Read Sequencing

The current example provides a version of the instant compositions and methods in which the libraries are prepared for sequencing on a long-read sequencing instrument, such as a Pacific Biosciences (PacBio®) Single Molecule, Real Time (SMRT)-seq instrument. A process adapted for longer sequence read lengths is thereby provided.

Example 12: Inverted Tissue-Puck System

The current example provides an additional option for tissue-puck contact in which rather than cutting sections of tissue and melting the sections directly onto a puck, pieces of tissue already adhered to a glass slide are transferred to a puck by pressing the puck and glass slide together. An inverted orientation approach is thereby provided.

Example 13: Puck Transfer while Retaining Spatial Positioning

The current example provides a further option in which the puck is physically transferred from one surface to another, for example by casting a gel on top of the puck, allowing the beads to be picked up off the surface without altering their positions relative to each other. An option for transferring a puck while retaining spatial positioning is thereby provided.

Example 14: Expanded Uses for Slide-seq Arrays

The current example provides further options for Slide-seq array design and use. In particular, in some embodiments described herein, Slide-seq arrays are used for capture of oligo nucleotides from cells and tissues, e.g., from: 1. oligonucleotide-conjugated antibodies and/or 2. hybridization probes for RNA/DNA.

Where hybridization probes for RNA/DNA are employed, such hybridization probes can have homology to sequences of the transcriptome or genome of the queried cell/tissue, or they could have unique sequence barcodes (e.g., unique molecular identifiers or UMIs) which optionally represent the identity of probes against: 1. proteins; 2. exons; 3. transcripts; 4. Single Nucleotide Polymorphisms (SNPs); and/or 5. genomic regions. Such probes can also include unique molecular identifiers (UMIs) which enable digital counting by sequencing of hybridized molecules.

The hybridization probes can be released from the array or tissue by art-recognized methods, specific examples of which include, but are not limited to: 1. via photolabile or photocleavable groups; 2. via T7 RNA polymerase transcription; 3. via enzymatic cleavage, for example RNAseH cleavage of bound RNA, or RNAse cleavage of an RNA base in the probe; and/or 4. via chemical cleavage: for example, disulfide cleavage.

Thus, the instant approach can be used for generation of a high-resolution image that accurately depicts the spatial distribution of expression for any bead-captured RNA of the transcriptome of a tissue sample.

The current compositions and methods can be used to understand the spatial organization of tissues in health and disease, with exemplary applications including: 1) Use for atlasing efforts to understand the diversity of cell types and their interactions in tissues and organs. 2) Use for studying how cell types change in tissue in response to perturbation and disease. 3) Use for studying post-mortem or clinical samples, and in particular, use to relate histopathological findings in diseased tissue to specific gene expression changes in specific cell types.

Application of the current compositions and methods to investigate gene expression patterns in tissues, potentially as a diagnostic tool, or as a tool for developing diagnostic assays, or pathological staging, for diseases (e.g., the instant approach can be used to profile many cancer sections (optionally alongside normal control sections), to reveal a spatial expression signature predictive of disease course and/or treatment response) is also expressly contemplated.

REFERENCES

1. A. Saunders et al., Molecular Diversity and Specializations among the Cells of the Adult Mouse Brain. Cell. 174, 1015-1030.e16 (2018).
2. S. Shah, E. Lubeck, W. Zhou, L. Cai, seqFISH Accurately Detects Transcripts in Single Cells and Reveals Robust Spatial Organization in the Hippocampus. Neuron. 94, 752-758.e1 (2017).
3. K. H. Chen, A. N. Boettiger, J. R. Moffitt, S. Wang, X. Zhuang, Spatially resolved, highly multiplexed RNA profiling in single cells. Science. 348 (2015).
4. E. Z. Macosko et al., Highly parallel genome-wide expression profiling of individual cells using nanoliter droplets. Cell. 161, 1202-1214 (2015).
5. A. M. Klein et al., Droplet barcoding for single-cell transcriptomics applied to embryonic stem cells. Cell. 161, 1187-1201 (2015).
6. P. L. Stahl et al., Visualization and analysis of gene expression in tissue sections by spatial transcriptomics. Science. 353, 78-82 (2016).

7. Materials and methods are available as supplementary materials online.
8. L. O. Trussell, D. Oertel, (Springer, Cham, 2018; link.springer.com/10.1007/978-3-319-71798-2_4), pp. 73-99.
9. M. T. Roberts, L. O. Trussell, Molecular Layer Inhibitory Interneurons Provide Feedforward and Lateral Inhibition in the Dorsal Cochlear Nucleus. J. Neurophysiol. 104, 2462-2473 (2010).
10. E. S. Lein et al., Genome-wide atlas of gene expression in the adult mouse brain. Nature. 445, 168-176 (2007).
11. C. Gravel, R. Hawkes, Parasagittal organization of the rat cerebellar cortex: Direct comparison of purkinje cell compartments and the organization of the spinocerebellar projection. J. Comp. Neurol. 291, 79-102 (1990).
12. A. Demilly, S. L. Reeber, S. A. Gebre, R. V. Sillitoe, Neurofilament Heavy Chain Expression Reveals a Unique Parasagittal Stripe Topography in the Mouse Cerebellum. The Cerebellum. 10, 409-421 (2011).
13. N. H. Barmack, Z. Qian, J. Yoshimura, Regional and cellular distribution of protein kinase C in rat cerebellar Purkinje cells. J. Comp. Neurol. 427, 235-54 (2000).
14. G. Brochu, L. Maler, R. Hawkes, Zebrin II: A polypeptide antigen expressed selectively by purkinje cells reveals compartments in rat and fish cerebellum. J. Comp. Neurol. 291, 538-552 (1990).
15. J. R. Sarna, H. Marzban, M. Watanabe, R. Hawkes, Complementary stripes of phospholipase Cβ3 and Cβ4 expression by Purkinje cell subsets in the mouse cerebellum. J. Comp. Neurol. 496, 303-313 (2006).
16. P. D. Storer, K. J. Jones, Ribosomal RNA transcriptional activation and processing in hamster rubrospinal motoneurons: Effects of axotomy and testosterone treatment. J. Comp. Neurol. 458, 326-333 (2003).
17. K. L. Adams, V. Gallo, The diversity and disparity of the glial scar. Nat. Neurosci. (2017), doi:10.1038/s41593-017-0033-9.
18. A. M. Kenney, J. D. Kocsis, Peripheral axotomy induces long-term c-Jun amino-terminal kinase-1 activation and activator protein-1 binding activity by c-Jun and junD in adult rat dorsal root ganglia In vivo. J. Neurosci. 18, 1318-28 (1998).
19. G. A. Robinson, Immediate early gene expression in axotomized and regenerating retinal ganglion cells of the adult rat. Mol. Brain Res. 24, 43-54 (1994).
20. J. Honkaniemi, S. M. Sagar, I. Pyykönen, K. J. Hicks, F. R. Sharp, Focal brain injury induces multiple immediate early genes encoding zinc finger transcription factors. Mol. Brain Res. 28, 157-163 (1995).
21. Y. Lin et al., Activity-dependent regulation of inhibitory synapse development by Npas4. Nature. 455, 1198-1204 (2008).
22. Q. Kong, M. P. Stockinger, Y. Chang, H. Tashiro, C. L. G. Lin, The presence of rRNA sequences in polyadenylated RNA and its potential functions. Biotechnol. J. 3, 1041-1046 (2008).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for obtaining spatially-resolvable macromolecule abundance data from a tissue sample, the method comprising:
   (i) using split-and-pool synthesis to generate a population of beads, wherein each bead of the population of beads has at least 1000 attached oligonucleotides, and wherein each of the at least 1000 attached oligonucleotides of each bead comprises:
      (a) a macromolecule-specific capture sequence, and
      (b) a bead identification sequence that is common to all at least 1000 oligonucleotides on each bead,
      wherein the bead identification sequence that is common to all at least 1000 oligonucleotides on each bead is either:
         a bead identification sequence that is unique to each bead within the population of beads, or
         a bead identification sequence that is a member of a population of bead identification sequences that is sufficiently degenerate to the population of beads that a majority of beads within the population of beads each possesses a unique bead identification sequence;
   (ii) contacting a capture material-coated solid support with the population of beads, wherein the capture material is a liquid electrical tape or a liquid dried to form a vinyl polymer, thereby capturing a subpopulation of the population of beads upon the solid support;
   (iii) identifying the bead identification sequence and an associated two-dimensional position on the solid support of each individual bead of the subpopulation of beads attached to the solid support;
   (iv) contacting the subpopulation of beads captured upon the solid support with the tissue sample; and
   (v) obtaining the sequences of a population of macromolecules bound to the each of the oligonucleotides and an associated bead identification sequence for each macromolecule sequenced, thereby obtaining spatially-resolvable macromolecule abundance data from the tissue sample.

2. The method of claim 1, wherein the beads of the population of beads have a diameter of 1-100 µm.

3. The method of claim 1, wherein the beads of the population of beads have a diameter of about 10 µm.

4. The method of claim 1, wherein the macromolecule is selected from the group consisting of RNA, DNA and protein.

5. The method of claim 1, wherein the macromolecule-specific capture sequence comprises a poly-dT tail of sufficient length to allow for capture of poly-A-tailed RNAs via hybridization.

6. The method of claim 1, wherein the macromolecule-specific capture sequence comprises a gene-specific or transcript-specific sequence.

7. The method of claim 4, wherein the DNA is selected from the group consisting of a genomic DNA and a DNA oligonucleotide comprising a barcode sequence.

8. The method of claim 7, wherein the DNA oligonucleotide comprising a barcode sequence is attached to a protein.

9. The method of claim 8, wherein the protein is an antibody.

10. The method of claim 1, wherein the macromolecule-specific capture sequence is a component of a loaded transposase.

11. The method of claim 1, wherein the tissue sample is fixed.

12. The method of claim 1, wherein the beads comprise porous polystyrene, porous polymethacrylate, and/or polyacrylamide.

13. The method of claim 1, wherein the step of (iii) identifying the bead identification sequence and associated two-dimensional position on the solid support of each individual bead of the subpopulation of beads attached to the solid support comprises performance of a sequencing-by-ligation technique.

14. The method of claim 5, wherein step (v) comprises performing reverse transcription upon captured poly-A-tailed RNAs immediately after hybridizing said poly-A-tailed RNAs to the beads and before performing a digestion step.

15. The method of claim 14, wherein the hybridizing is performed in a 6×SSC buffer supplemented with a detergent.

16. A method for making an array of beads attached to a solid support, the method comprising:
(i) performing split-and-pool synthesis upon a population of beads to generate a population of beads in which each bead of the population of beads has at least 1000 attached oligonucleotides, and wherein each of the at least 1000 attached oligonucleotides of each bead comprises:
  (a) a macromolecule-specific capture sequence, and
  (b) a bead identification sequence that is common to all at least 1000 oligonucleotides attached to each bead, wherein the bead identification sequence that is common to all at least 1000 oligonucleotides attached to each bead is either:
    a bead identification sequence that is unique to each bead within the population of beads, or
    a bead identification sequence that is a member of a population of bead identification sequences that is sufficiently degenerate to the population of beads that a majority of beads within the population of beads each possesses a unique bead identification sequence; and
(ii) contacting a capture material-coated solid support with the population of beads in which each bead of the population of beads has at least 1000 attached oligonucleotides, wherein the capture material is a liquid electrical tape or a liquid dried to form a vinyl polymer, thereby capturing a subpopulation of the population of beads upon the solid support and making an array of beads attached to the solid support.

17. A method for obtaining spatially-resolvable macromolecule abundance data from a tissue sample, the method comprising:
(i) using split-and-pool synthesis to generate a population of beads, wherein each bead of the population of beads has at least 1000 attached oligonucleotides capable of macromolecule capture, and wherein each of the at least 1000 attached oligonucleotides capable of macromolecule capture of each bead comprises:
  (a) a macromolecule-specific capture sequence, and
  (b) a bead identification sequence that is common to all at least 1000 oligonucleotides capable of macromolecule capture on each bead, wherein the bead identification sequence that is common to all at least 1000 oligonucleotides capable of macromolecule capture on each bead is a bead identification sequence that is a member of a population of bead identification sequences that is sufficiently degenerate to the population of beads that a majority of beads within the population of beads each possesses a unique bead identification sequence;
(ii) contacting a capture material-coated slide with the population of beads, wherein the capture material is a liquid electrical tape or a liquid dried to form a vinyl polymer, thereby capturing a subpopulation of the population of beads upon the slide;
(iii) identifying the bead identification sequence and an associated two-dimensional position on the slide of each individual bead of the subpopulation of beads attached to the slide;
(iv) contacting the subpopulation of beads captured upon the slide with the tissue sample; and
(v) obtaining the sequences of a population of macromolecules bound to the each of the oligonucleotides and an associated bead identification sequence for each macromolecule sequenced, thereby obtaining spatially-resolvable macromolecule abundance data from the tissue sample.

\* \* \* \* \*